(12) United States Patent
Posner et al.

(10) Patent No.: US 7,973,024 B2
(45) Date of Patent: Jul. 5, 2011

(54) 24-SULFOXIMINE VITAMIN $D_3$ COMPOUNDS

(75) Inventors: Gary Posner, Baltimore, MD (US); Mehmet Kahraman, Baltimore, MD (US); Uttam Saha, Toronto (CA)

(73) Assignee: Cyctochroma Inc., Markham (CA)

( * ) Notice: Subject to any disclaimer, the term of this patent is extended or adjusted under 35 U.S.C. 154(b) by 893 days.

(21) Appl. No.: 11/442,148

(22) Filed: May 30, 2006

(65) Prior Publication Data

US 2006/0217353 A1    Sep. 28, 2006

Related U.S. Application Data

(62) Division of application No. 10/460,656, filed on Jun. 13, 2003, now Pat. No. 7,101,865.

(60) Provisional application No. 60/387,904, filed on Jun. 13, 2002.

(51) Int. Cl.
*A61K 31/593* (2006.01)
(52) U.S. Cl. .................................................. 514/167
(58) Field of Classification Search ................... 514/167
See application file for complete search history.

(56) References Cited

U.S. PATENT DOCUMENTS

| | | | |
|---|---|---|---|
| 4,481,198 | A | 11/1984 | DeLuca et al. |
| 6,043,386 | A | 3/2000 | Posner et al. |
| 6,380,408 | B1 | 4/2002 | Posner et al. |

FOREIGN PATENT DOCUMENTS

| | | |
|---|---|---|
| EP | 0386793 | 12/1990 |
| WO | WO 9115475 | 10/1991 |
| WO | WO 9410139 | 5/1994 |
| WO | WO 9414766 | 7/1994 |
| WO | WO 0059513 | 10/2000 |

OTHER PUBLICATIONS

Schroder E. et al., "Arzneimittelchemie passage", Arzneimittelchemie Grundlagen Nerven, 1976, pp. 30-33, XP002186820.
Greising, D. M. et al., "A-Ring Analogues of 1,25-$(OH)_2D_3$ With Low Affinity for the Vitamin D Receptor Modulate Chondrocytes via Membrane Effects That Are Dependent on Cell Maturation," Journal of Cellular Physiology, 1997, pp. 357-367, vol. 171.
Hartman, R. W. et al., "Synthesis and Evaluation of Novel Steroidal Oxime Inhibitors of P450 17 (17α-Hydroxlase/C17-20-Lyase) and 5α-Reductase Types 1 and 2," Journal of Medical Chemistry, 2000, pp. 4266-4277, vol. 43, No. 22.
Kensler, T. W. et al., "Conceptually new deltanoids (vitamin D analogs) inhibit multistage skin tumorigenesis," Carcinogenesis, 2000, pp. 1341-1345, vol. 21, No. 7.
Posner, G. H. et al., "Sterocontrolled Synthesis of a Trihydroxylated A Ring as an Immediate Precursor to 1α,2α,25-Trihydroxyvitamin $D_3$," J. Org. Chem., 1991, pp. 4339-4341, vol. 56.
Posner, G. H. et al., "New Vitamin $D_3$ Derivatives with Unexpected Antiproliferative Activity: 1-(Hydroxymethyl)-25-hydroxyvitamin $D_3$ Homologs," J. Med. Chem., 1992, pp. 3280-3287, vol. 35.

Dai, H et al., "Synthetic Approaches to Vitamin D," Synthesis, 1994, pp. 1383-1397.
Posner, G. H. et al., "Sterocontrolled Total Synthesis of Calcitriol Derivatives: 1,25-Dihydroxy-2-(4'- hydroxybutyl)vitamin $D_3$ Analogs of an Osteoporosis Drug," J. Org. Chem., 1994, pp. 7855-7861, vol. 59.
Posner, G. H. et al., "1α,25-Dihydroxyvitamin $D_3$ Hybrid Analogs with Structural Changes at Both the A-Ring and the C,D-Ring Sidechain. 11," Bioorganic & Medicinal Chemistry Letters, 1995, pp. 2163-2168, vol. 5, No. 18.
Posner, G. H. et al., "1α,25-Dihydroxyvitamin $D_3$ Hybrid Analogs with Structural Changes at Both the A-Ring and the C,D-Ring Sidechain," Bioorganic & Medicinal Chemistry Letters, 1994, pp. 2919-2924, vol. 4, No. 24.
Posner, G.H. et al., "1α,25-Dihydroxyvitamin $D_3$ Analogs Featuring Aromatic and Heteroaromatic Rings: Design, Synthesis and Preliminary Biological Testing," J. Med. Chem., 1995, pp. 4529-4537, vol. 38.
Posner, G. H., "New vitamin D analogues," Nephrol. Dial. Transplant., 1996, pp. 32-36, vol. 11, Suppl. 3.
Peleg, S. et al., "A 20-Epi Side Chain Restores Growth-Regulatory and Transcriptional Activities of an A Ring-Modified Hybrid Analog of 1α,25-Dihydroxyvitamin $D_3$ Without Increasing Its Affinity to the Vitamin D Receptor," Journal of Cellular Biochemistry, 1996, pp. 149-161, vol. 63.
Posner, G. H. et al., "Antiproliferative Hybrid Analogs of the Hormone 1α,25-Dihydroxyvitamin $D_3$,: Design, Synthesis, and Preliminary Biological Evaluation," J. Org. Chem., 1997, pp. 3299-3314, vol. 62.
Posner, G. H. et al., "Noncalcemic, Antiproliferative, Transcriptionally Active, 24-Fluorinated Hybrid Analogues of the Hormone 1α,25-Dihydroxyvitamin D, Synthesis and Preliminary Biological Evaluation," Journal of Medicinal Chemistry, 1998. pp. 3008-3014 vol. 41 No. 16.
Peleg, S. et al., "Differential Use of Transcription Activation Function 2 Domain of the Vitamin D Receptor by 1,25-Dihydroxyvitamin D, and It's A Ring-Modified Analogs," Molecular Endocrinology, 1998, pp. 525-535, vol. 12, No. 4.
Posner, G. H. et al., "Vitamin D Endocrine System Structural, Biological, Genetic and Clinical Aspects," Proceedings of Eleventh Workshop on Vitamin D, Nashville, Tennessee, May 27-Jun. 1, 2000, pp. 3-10, Norman A. W et al. Eds. Printing and Reprographics University of California, Riverside, USA.
Posner, G. H. et al., "A Non-Calcemic Sulfone Version of the Vitamin D, Analogue Seocalcitol (EB 1089): Chemical Synthesis, Biological Evaluation and Potency Enhancement of the Anticancer Drug Adramycin," Bioorganic & Medicinal Chemistry 2001, pp. 2365-2371, vol. 9.

(Continued)

*Primary Examiner* — Barbara P Badio
(74) *Attorney, Agent, or Firm* — Marshall, Gerstein & Borun LLP

(57) ABSTRACT

The present invention provides novel sulfoximine compounds, compositions comprising these compounds and methods of using these compounds as inhibitors of CYP24. In particular, the compounds of the invention are useful for treating diseases which benefit from a modulation of the levels of 1α,25-dihydroxy vitamin $D_3$, for example, cell-proliferative disorders.

26 Claims, 19 Drawing Sheets

OTHER PUBLICATIONS

Hofer, H. et al., "Biological Effects of 1α-Hydroxy-and 1β-(Hydroxymethyl)-Vitamin D Compounds Relevant for Potential Colorectal Cancer Therapy," The Journal of Pharmacology and Experimental Therapeutics, 1999, pp. 450-455, vol. 291, No. 2.

Boyan, B. D. et al., "1,25-$(OH)_2D_3$, modulates growth plate chondrocytes via membrane receptor-meiated protein kinase C by a mechanism that involves changes in phospholipid metabolism and the action of arachidonic acid and $PGE_2$," Steroids, 1999, pp. 129-136, vol. 64.

Posner, G. H. et al., "2,2-Disubstituted Analogues of the Natural Hormone 1α,25-Dihydroxyvitamin $D_3$: Chemistry and Biology," Bioorganic & Medicinal Chemistry, 2002, pp. 2353-2365, vol. 10.

Hatcher, M. A. et al., "[3,3]-Sigmatropic rearrangements: short, stereo controlled syntheses of functionalized vitamin $D_3$ side-chain units," Tetrahedron letters, 2002, pp. 5009-5012, vol. 43.

Guyton, K. Z. et al., "Vitamin D and Vitamin D Analogs as Cancer Chemopreventive Agents," Nutrition Reviews, 2003, pp. 1-12, vol. 61, No. 7.

Hilpert, H. et al., "Novel versatile approach to an enantiopure 19-*nor* des-C,D vitamin $D_3$ derivative," Tetrahedron, 2001, pp. 681-694, vol. 57.

Posner, G. H. et al., "2-Fluoroalkyl A-Ring Analogs of 1,25-Dihydroxyvitamin $D_3$-Sterocontrolled Total Synthesis via Intramolecular and Intermolecular Diels-Alder Cycloadditions. Preliminary Biological Testing," J. Org. Chem., 1995, pp. 4617-4628, vol. 60.

Peleg, S. et al., "Vitamin D Analogs as Modulators of Vitamin D Receptor Action," Current Topics in Medicinal Chemistry, 2003, pp. 1-20, vol. 3.

Guyton, K. Z. et al., "Cancer Chemoprevention Using Natural Vitamin D and Synthetic Analogs," Annu. Rev. Pharmacol. Toxicol., 2001, pp. 421-442, vol. 41.

Posner, G. H. et al., "Conceptually New Sulfone Analogues of the Hormone 1α,25-Dihydroxyvitamin $D_3$: Synthesis and Preliminary Biological Evaluation," Journal of Medicinal Chemistry, 1999, pp. 3425-3435, vol. 42, No. 18.

Posner, G. H. et al., "Conceptually New 20-epi-22-Oxa Sulfone Analogues of the Hormone 1α, 25-Dihydroxyvitamin $D_3$: Synthesis and Biological Evaluation," Journal of Medicinal Chemistry, 2000, pp. 3581-3586, vol. 43, No. 19.

Posner, G. H. et al., "Conceptually New Low-Calcemic Oxime Analogues of the Hormone 1α,25-Dihydroxyvitamin $D_3$: Synthesis and Biological Testing," J. Med. Chem., 2002, pp. 1723-1730, vol. 45.

Crawford, K. R., "Design, Synthesis, and Preliminary Biological Evaluation of Analogs of 1α,25-Dihydroxyvitamin $D_3$: Modifications to the A-Ring and C,D-Ring Side Chain," Ph.D. Thesis, Johns Hopkins University, 2001, pp. 13-56 and 51-55.

Wang, Q., "Part I: Noncalcemic, Antiproliferative, Transcriptionally Active Hybrid Analogs of the Hormone 1α,25-Dihydroxyvitamin $D_3$: Design, Synthesis, and Preliminary Biological Evaluation," Ph.D. Thesis, Johns Hopkins University, 2000, pp. 39-57.

Shuster et al., "Selective Inhibition of Vitamin D Hydroxylases in Human Keratinocytes," Steroids, 2001, pp. 409-422, vol. 66.

Haider, S., et al., "Synthesis and Evaluation of Steroidal Hydroxamic Acids as Inhibitiors of P450 17 (17 α-Hydroxylase/C17-20-Lyase)," Arch. Pharm. Pharm. Med. Chem., 2001, pp. 138-140, vol. 334.

Beer et al. Am J Clin Oncol 27(5):535-541 (2004).

Beer et al., J Clin Oncol 21(1):123-128 (2003).

Bouillon et al., Endocrine Reviews 16(2):200-257 (1995).

Cheng and Coyne, Therapeutics and Clinical Risk Management 2(3):297-301 (2006).

Colston et al., British Journal of Cancer 76(8):1017-1020 (1997).

Fujioka et al., J Urol 160(1):247-251 (1998).

Huerta et al. Cancer Res 62:741-746 (2002).

Iseki et al., Int. J. Cancer 81:730-733 (1999).

Jones et al., Anticancer Research 26:2589-2596 (2006).

Kusudo et al. Biochemical and Biophysical Research Communications 309:885-892 (2003).

Kusudo et al., Biochemical and Biophysical Research Communications 321:774-782 (2004).

Masood et al., Blood 96(9):3188-3194 (2000).

Masuda et al., Biochimca ey Biophysica Acta 1761:221-234 (2006).

Morris et al., Cancer 100(9):1868-1875 (2004).

Prudencio et al. Journal of the National Cancer Institute 93(10):745-753 (2001).

Rao et al. Cancer Research 64:2143-2147 (2004).

Sakaki et al., Biochemical Pharmacolog 65:1957-1965 (2003).

Shankar et al., Archives of Biochemistry and Biophysics 387(2):297-306 (2001).

Trump et al. Cancer 106(10):2136-212 (2006).

Trydal et al., Cancer Res 48:2458-2461 (1988).

Zhou et al., Cancer Epidemiol Biomarkers Prev. 14(10):2303-2309 (2005).

24-SULFOXIMINE VITAMIN $D_3$ COMPOUNDS

This is a divisional of prior co-pending U.S. application Ser. No. 10/460,656, filed Jun. 13, 2003 (now U.S. Pat. No. 7,101,865, issued Sep. 5, 2006), which claims the benefit of U.S. Provisional Application No. 60/387,904, filed Jun. 13, 2002.

This invention was made with government support under NIH Grant Number CA44530. The government has certain rights in the invention.

FIELD OF THE INVENTION

The present invention relates to novel 24-sulfoximine vitamin $D_3$ compounds that show selective inhibition of the enzyme CYP24, to pharmaceutical and diagnostic compositions containing them and to their medical use, particularly in the treatment and/or prevention of cancer, dermatological disorders, bone disorders, parathyroid disorders, wound healing, osteoporosis and autoimmune disorders.

BACKGROUND OF THE INVENTION

The vitamin D metabolic pathway is part of a vital endocrine system that is highly regulated at certain stages and produces metabolites that control the secretion of the parathyroid gland hormones (Beckman, M., and DeLuca, H. (1997) *Methods in Enzymol.* 282, 200-223; Jones, G., Strugnell, S., and DeLuca, H. (1998) *Physiol. Rev.* 78, 1193-1231). 1α,25-Dihydroxy vitamin $D_3$, also known as calcitriol (see below), a hormone produced in the vitamin D pathway, regulates phosphate and calcium levels in the blood which in turn control bone mass, the state of bones, and affects cellular differentiation in the skin and the immune system (Armbrecht, H. J., Okuda, K., Wongsurawat, N., Nemani, R., Chen, M., and Boltz, M. (1992) *J. Steroid Biochem. Molec. Biol.* 43, 1073-1081). In the vitamin D pathway, cytochrome P450s are enzymes that introduce functional groups by hydroxylation, usually at positions 1, 25, and 24, of vitamin $D_3$ (Beckman; M; and DeLuca, H. (1997) *Methods in Enzymol.* 282, 200-223).

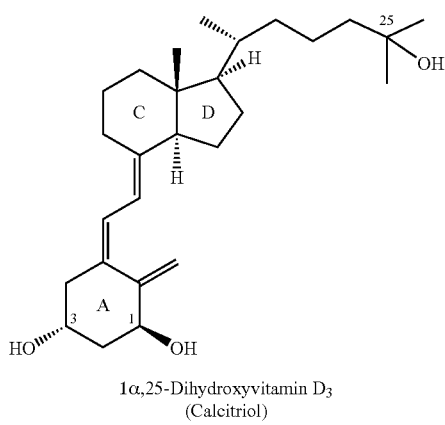

1α,25-Dihydroxyvitamin $D_3$
(Calcitriol)

1α,25-Dihydroxy vitamin $D_3$ is converted to 1α,24,25-trihydroxy-$D_3$ by a mitochondrial P450 known as CYP24 (Bell, N. H., (1998) *J Bone Miner. Res.* 13, 350-35211). CYP24 is induced by 1α,25-dihydroxy-$D_3$ and is found in the kidney as well as other vitamin D target tissues such as the parathyroid cells, keratinocytes, osteoblasts, and enteroctyes (Jones, G., Strugnell, S., and DeLuca, H. (1998) *Physiol. Rev.* 78, 1193-1231).

The biological effects of 1α,25-dihydroxy vitamin $D_3$ (calcitriol) and its synthetic analogs are mediated by the nuclear vitamin D receptor (VDR). Calcitriol has an important role in the antiproliferative and growth regulatory effects on normal and neoplastic cells (for e.g. prostate cancer cells). VDR ligands have potential widespread clinical application, however in many cases, hypercalcemia develops as a side effect which prevents sustained systemic administration. Inhibiting the catabolism of calcitriol and its analogs is expected to lengthen the biological lifetime of these compounds and thus to allow smaller amounts of them to be used for effective human chemotherapy. Such smaller dosing will avoid, or at least minimize, the hypercalcemic toxicity associated with medicinal use of these compounds. Further inhibition of the catabolism of 1α,25-dihydroxy vitamin $D_3$ increases the endogenous levels of this hormone, which will also have beneficial therapeutic effects.

There is a need for compounds that modulate the activity of CYP24, and therefore the levels of 1α,25-dihydroxy vitamin $D_3$ and analogs thereof:

SUMMARY OF THE INVENTION

It has been found that certain 24-sulfoximine vitamin $D_3$ compounds show selective inhibition of the enzyme CYP24.

The present invention therefore provides compounds of Formula I, and pharmaceutically acceptable acid addition salts, hydrates, solvates and prodrugs thereof:

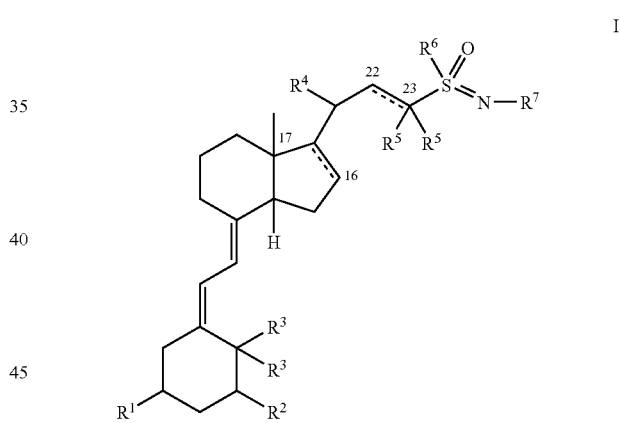

wherein
$R^1$ is selected from the group consisting of OH, $OC_{1-4}$alkyl, and halo;
$R^2$ is selected from the group consisting of H, OH, $OC_{1-4}$alkyl, and halo;
each $R^3$ are either both H or together form $=CH_2$;
$R^4$ is $C_{1-4}$alkyl;
⋯⋯ represents a single or a double bond;
each $R^5$ can be the same or different and is selected from the group consisting of hydrogen, halo and $C_{1-4}$alkyl or each $R^5$ can be taken together to form a $C_{3-6}$cycloalkyl ring;
$R^6$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo;
$R^7$ is selected from the group consisting of H, $C_{1-6}$alkyl and $C(O)R^8$; and $R^8$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo, provided that when there is a double bond between C22 and C23, there is only one $R^5$ group attached to C23 and $R^5$ is selected from the group consisting of hydrogen, halo and $C_{1-4}$alkyl.

According to another aspect of the present invention, there is provided a pharmaceutical composition comprising a compound of the invention and a pharmaceutically acceptable carrier or diluent.

By selectively modulating CYP24, the enzyme that metabolizes $1\alpha,25$-dihydroxy vitamin $D_3$, the levels of $1\alpha,25$-dihydroxy vitamin $D_3$ (either endogenous or administered as part of a chemotherapeutic regimen), or an analog of $1\alpha,25$-dihydroxy vitamin $D_3$, will also be modulated. Diseases that benefit from a modulation of the levels of $1\alpha,25$-dihydroxy vitamin $D_3$ can therefore be treated using a modulator of CYP24. Further, by inhibiting the catabolism of $1\alpha,25$-dihydroxy vitamin $D_3$, the compounds of the invention will increase the endogenous levels of this hormone, which will result in similar beneficial therapeutic effects. By acting preferentially on CYP24, side effects caused by interaction with other enzymes and receptors will be reduced. Accordingly, the present invention provides a method for treating diseases which benefit from a modulation of the levels of $1\alpha,25$-dihydroxy vitamin $D_3$, or an analog of $1\alpha,25$-dihydroxy vitamin $D_3$, comprising administering an effective amount of a compound of the invention to a cell or animal in need thereof. The invention also includes the use of a compound of the invention to treat diseases which benefit from a modulation of the levels of $1\alpha,25$-dihydroxy vitamin $D_3$, or an analog of $1\alpha,25$-dihydroxy vitamin $D_3$. Further, the invention includes a use of a compound of the invention to prepare a medicament to treat diseases which benefit from a modulation of the levels of $1\alpha,25$-dihydroxy vitamin $D_3$, or an analog of $1\alpha,25$-dihydroxy vitamin $D_3$.

Inhibition of CYP24 will inhibit the catabolism of $1\alpha,25$-dihydroxy vitamin $D_3$, or its analogs, which will lengthen the biological lifetime of these compounds and thus allow smaller amounts of them to be used for effective disease treatment. Such smaller dosing will avoid, or at least minimize, the hypercalcemic toxicity associated with medicinal use of $1\alpha,25$-dihydroxy vitamin $D_3$ and its analogs. Therefore, in an embodiment, the present invention provides a method for treating diseases which benefit from inhibiting the catabolism of $1\alpha,25$-dihydroxy vitamin $D_3$, or an analog of $1\alpha,25$-dihydroxy vitamin $D_3$, comprising administering an effective amount of a compound of the invention to a cell or animal in need thereof. The invention also includes the use of a compound of the invention to treat diseases which benefit from inhibiting the catabolism of $1\alpha,25$-dihydroxy vitamin $D_3$, or an analog of $1\alpha,25$-dihydroxy vitamin $D_3$. Further, the invention includes a use of a compound of the invention to prepare a medicament to treat diseases which benefit from inhibiting the catabolism of $1\alpha,25$-dihydroxy vitamin $D_3$, or an analog of $1\alpha,25$-dihydroxy vitamin $D_3$.

Diseases which will benefit from a modulation in the levels of $1\alpha,25$-dihydroxy vitamin $D_3$ or its analogs, include, but are not limited to:
  (i) in the parathyroid—hyper- and hypo-parathyroidism, Osudohypo-parathyroidism, Secondary hyperparathyroidism;
  (ii) in the pancreas—diabetes;
  (iii) in the thyroid—medullary carcinoma;
  (iv) in the skin—psoriasis; wound healing;
  (v) in the lung—sarcoidosis and tuberculosis;
  (vi) in the kidney—chronic renal disease, hypophosphatemic VDRR, vitamin D dependent rickets;
  (vii) in the bone—anticonvulsant treatment, fibrogenisis imperfecta ossium, osteitits fibrosa cystica, osteomalacia, osteoporosis, osteopenia, osteosclerosis, renal osteodytrophy, rickets;
  (viii) in the intestine—glucocorticoid antagonism, idopathic hypercalcemia, malabsorption syndrome, steatorrhea, tropical sprue; and
  (ix) autoimmune disorders.

In embodiments of the invention, the disease that benefits from a modulation in the levels of $1\alpha,25$-dihydroxy vitamin $D_3$, or an analog of $1\alpha,25$-dihydroxy vitamin $D_3$, are selected from cancer, dermatological disorders (for example psoriasis), parathyroid disorders (for example hyperparathyroidism and secondary hyperparathyroidism), bone disorders (for example osteoporosis) and autoimmune disorders.

In accordance with a further aspect of the present invention, the disease that benefits from a modulation in the levels of $1\alpha,25$-dihydroxy vitamin $D_3$, or an analog of $1\alpha,25$-dihydroxy vitamin $D_3$, is a cell proliferative disorder. Accordingly, there is provided a method for modulating cell proliferation (preferably inhibiting cell proliferation) and/or for promoting cell differentiation, comprising administering an effective amount of a compound of the invention to a cell or animal in need thereof. The invention also includes a use of a compound of the invention to modulate cell proliferation (preferably to inhibit cell proliferation) and/or to promote cell differentiation. The invention further includes a use of a compound of the invention to prepare a medicament to modulate cell proliferation (preferably to inhibit cell proliferation) and/or to promote cell differentiation.

In another embodiment of the present invention, the disease that benefits from a modulation in the levels of $1\alpha,25$-dihydroxy vitamin $D_3$, or an analog of $1\alpha,25$-dihydroxy vitamin $D_3$, is cancer, Accordingly, the present invention provides a method of treating cancer comprising administering an effective amount of a compound of the invention to a cell or animal in need thereof. The invention also includes a use of a compound of the invention to treat cancer. The invention further includes a use of a compound of the invention to prepare a medicament to treat cancer. In embodiments of the invention, the cancer is selected from the group consisting of breast cancer, lung cancer, prostate cancer, colon and colorectal cancer, kidney cancer, head and neck cancer, pancreatic cancer, skin cancer, Kaposi's sarcoma and leukemia.

In another aspect, the invention provides a method of modulating CYP24 activity in a cell by administering an effective amount of a compound of the invention. In a further aspect, the invention provides a method of inhibiting CYP24 activity in a cell by administering an effective amount of a compound of the invention. The present invention also provides a use of a compound of the invention to modulate, preferably to inhibit, CYP24 activity. The present invention further provides a use of a compound of the invention to prepare a medicament to modulate CYP24 activity, preferably to inhibit CYP24 activity.

The compounds of the invention can be used alone or in combination with other agents that modulate CYP24 activity, or in combination with other types of treatment (which may or may not modulate CYP24) for diseases that benefit from a modulation in the levels of $1\alpha,25$-dihydroxy vitamin $D_3$, or an analog thereof, and/or an inhibition of the catabolism of $1\alpha,25$-dihydroxy vitamin $D_3$, or an analog thereof. Preferably the compounds of the invention are administered in combination with 1α,25-dihydroxy vitamin D₃ (calcitriol), an analog of 1α,25-dihydroxy vitamin D₃ or other vitamin D receptor agonists. Inhibiting catabolism of vitamin D receptor agonists such as 1α,25-dihydroxy vitamin D₃, or analogs thereof, will lengthen the biological lifetime or efficacy of these therapies and thus to allow smaller amounts of the drug to be used for effective human chemotherapy; such smaller dosing will avoid, or at least to minimize, the hypercalcemic toxicity associated with medicinal use of these compounds. The present invention therefore provides a method of increasing the efficacy of a vitamin D receptor agonist, preferably 1α,25-dihydroxy vitamin D₃, or an analog thereof, comprising co-administering an effective amount of a compound of the invention and an effective amount of the vitamin D receptor agonist, preferably 1α,25-dihydroxy vitamin D₃, or an analog thereof. Further the invention includes the use of a compound of the invention to increase the efficacy of a vitamin D receptor agonist, preferably 1α,25-dihydroxy vitamin D₃, or an analog thereof, and a use of a compound of the invention to prepare a medicament to increase the efficacy of a vitamin D receptor agonist, preferably 1α,25-dihydroxy vitamin D₃, or an analog thereof.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Definitions

Figure 1:
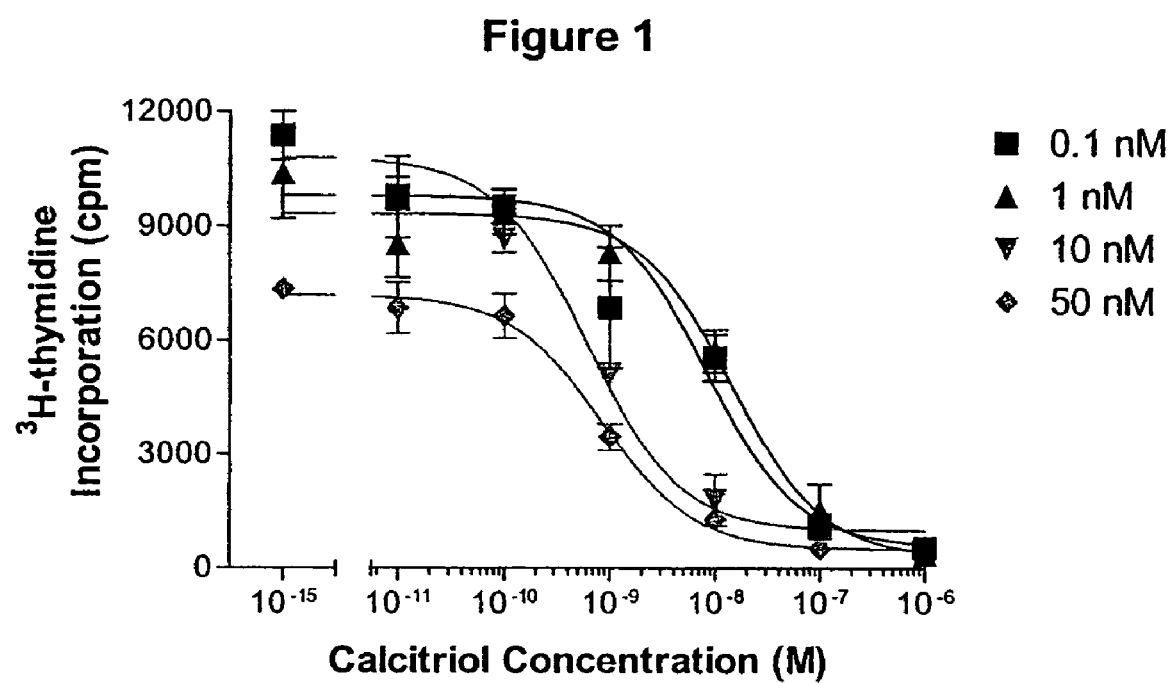
FIG. 1 is a graph showing that compound I(g) and calcitriol act to inhibit the proliferation of MCF-7 cells. MCF-7 cells were treated with specified concentrations of calcitriol and compound I(g) for three days. Cells were then incubated with [³H]-thymidine for 6 h at 37° C. in a humidified atmosphere containing 5% $CO_2$. Plates were harvested and radioactivity measured. Dose response curves for 0.1 nM I(g) (■), 1 nM I(g) (▲), 10 nM I(g) (▼) and 50 nM I(g) (♦) are shown.

The term "$C_{1-4}$alkyl" as used herein means straight and/or branched chain alkyl groups containing from one to four carbon atoms and includes methyl, ethyl, propyl, isopropyl, t-butyl and the like.

The term "$C_{1-4}$alkoxy" as used herein means straight and/or branched chain alkoxy groups containing from one to four carbon atoms and includes methoxy, ethoxy, propyloxy, isopropyloxy, t-butoxy and the like.

The term "cycloalkyl" as used herein means an unsubstituted or substituted saturated cyclic ring containing from three to six carbon atoms and includes cyclopropyl, cyclobutyl, cyclopentyl and cyclohexyl.

The term "aryl" as used herein means unsubstituted or substituted mono- or bicyclic aromatic groups containing from 6 to 14 carbon atoms and includes phenyl and naphthyl and the like.

The term "heteroaryl" as used herein means unsubstituted or substituted mono- or bicyclic heteroaromatic groups containing from 5 to 14 carbon atoms, of which 1-3 atoms may be a heteroatom selected from the group consisting of S, O and N, and includes furanyl, thienyl, pyrrolo, pyridyl, indolo, benzofuranyl and the like.

The term "halo" as used herein means halogen and includes chloro, flouro, bromo and iodo.

As to any of the above groups that contain one or more substituents, it is understood, of course, that such groups do not contain any substitution or substitution patterns which are sterically impractical and/or synthetically non-feasible.

The term "pharmaceutically acceptable" as used herein means to be compatible with the treatment of animals, in particular humans.

The term "pharmaceutically acceptable acid addition salt" as used herein means any non-toxic organic or inorganic salt of any base compound of the invention, or of any of its intermediates. For example, the compounds of the invention may form an acid addition salt at the imine nitrogen (for preparation of such salts see Brandt, J.; Gais, H-J. *Tetrahedron; Asymmetry,* 1997, 8, 909 and Shiner, C. S.; Berks, A. H. *J. Org. Chem.* 1988, 53, 5542, Appel, R.; Fehlaber, H.; Hanssgen, D.; Schollhorn, R. *Chem, Ber.* 1966, 99, 3108, Akasara, T.; Furukawa, N.; Oae, S. *Phosphorus and Sulfur* 1985, 21, 277, Johnson, C. R Janiga, E. R. Haake, M. *J. Am. Chem. Soc.* 1968, 90, 3890 and Johnson, C. R. Janiga, E. R. *J. Am. Chem. Soc.* 1973, 95, 7692). Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the invention, for laboratory use, or for subsequent conversion to a pharmaceutically acceptable acid addition salt.

The term "solvate" as used herein means a compound of the invention wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "compound(s) of the invention" as used herein means compound(s) of Formula I, and acid addition salts, hydrates, solvates and prodrugs thereof.

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that modulates CYP24 activity, an effective amount of an agent is, for example, an amount sufficient to achieve such a modulation in CYP24 activity as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "modulate" as used herein includes the inhibition or suppression of a function or activity (such as CYP24 activity) as well as the enhancement of a function or activity.

To "inhibit" or "suppress" or "reduce" a function or activity, such as CYP24 activity, is to reduce the function or activity when compared to otherwise same conditions except for a condition or parameter of interest, or alternatively, as compared to another conditions.

The term "animal" as used herein includes all members of the animal kingdom including human. The animal is preferably a human.

The term "a cell" as used herein includes a plurality of cells. Administering a compound to a cell includes in vivo, ex vivo and in vitro treatment.

The term "cancer" as used herein includes all forms of cancer or neoplastic disease.

The term "1α,3β-stereochemistry" as used herein refers to the relative configuration of the groups, $R^1$ and $R^2$, in which $R^2$ is above the plane of the page, and the $R^1$ is below the plane of the page. The term "1β,3α-stereochemistry" as used herein refers to the relative configuration of the groups, $R^1$ and $R^2$, in which $R^1$ is above the plane of the page, and the $R^2$ is below the plane of the page.

II. Compounds of the Invention

Novel compounds showing selective inhibition of the enzyme CYP24 have been prepared. As such, the compounds of the invention are useful for modulating CYP24 activity and to treat diseases or disorders which benefit from such a modulation.

Accordingly, the present invention provides compounds of Formula I, and pharmaceutically acceptable acid addition salts, hydrates, solvates and prodrugs thereof:

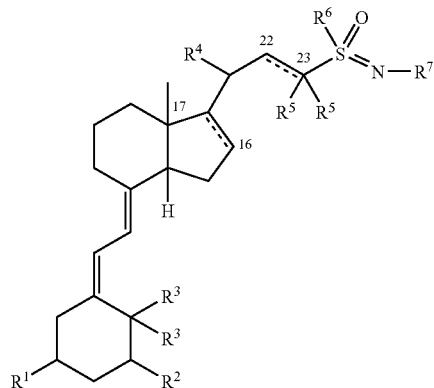

wherein
$R^1$ is selected from the group consisting of OH, $OC_{1-4}$alkyl, and halo;
$R^2$ is selected from the group consisting of H, OH, $OC_{1-4}$alkyl, and halo;
each $R^3$ are either both H or together form $=CH_2$;
$R^4$ is $C_{1-4}$alkyl;
----- represents a single or a double bond;
each $R^5$ can be the same or different and is selected from the group consisting of hydrogen, halo and $C_{1-4}$alkyl or each $R^5$ can be taken together to form a $C_{3-6}$cycloalkyl ring;
$R^6$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo;
$R^7$ is selected from the group consisting of H, $C_{1-6}$alkyl and $C(O)R^8$; and
$R^8$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo,
provided that when there is a double bond between C22 and C23, there is only one $R^5$ group attached to C23 and $R^5$ is selected from the group consisting of hydrogen, halo and $C_{1-4}$alkyl.

The compounds of Formula I include those in which $R^1$ is selected from the group consisting of OH, $OC_{1-4}$alkyl, and halo and $R^2$ is selected from the group consisting of H, OH, $OC_{1-4}$alkyl, and halo. In embodiments of the present invention, $R^1$ is selected from the group consisting of OH, $OCH_3$ and fluoro and $R^2$ is selected from the group consisting of H, OH, $OCH_3$ and fluoro. In further embodiments of the present invention, $R^1$ is OH and $R^2$ is selected from the group consisting of H and OH. In still further embodiments, $R^1$ and $R^2$ are both OH.

The present invention includes compounds of Formula I wherein each $R^3$ are either both H or together form $=CH_2$. In embodiments of the invention, $R^3$ is $=CH_2$. n further embodiments of the present invention, both $R^3$ are H.

The present invention includes compounds of Formula I wherein $R^4$ is $C_{1-4}$alkyl. In embodiments of the invention, $R^4$ is $CH_3$.

The present invention includes compounds of the Formula I wherein each $R^5$ can be the same or different and is selected from the group consisting of hydrogen, halo and $C_{1-4}$alkyl or each $R^5$ can be taken together to form a $C_{3-6}$cycloalkyl ring. In embodiments of the invention, each $R^5$ is selected from the group consisting of F, $C_{1-4}$alkyl group and H or each $R^5$ can be taken together to form a $C_{3-6}$cycloalkyl ring. In further embodiments, each $R^5$ group is selected from the group consisting of F, $CH_3$ and H or each $R^5$ group is taken together to form a $C_{3-4}$cycloalkyl ring. In still further embodiments, both $R^5$ are either both H, $CH_3$ or F or each $R^5$ group is taken together to form a cyclopropyl ring. In even further embodiments of the invention, both $R^5$ are H.

The present invention includes compounds of the Formula I wherein $R^6$ selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo. In embodiments of the present invention $R^6$ is selected from the group consisting of $C_{1-4}$alkyl, $C_{3-5}$cycloalkyl, aryl and heteroaryl, wherein each of $C_{1-4}$alkyl, $C_{3-5}$cycloalkyl, aryl and heteroaryl are either unsubstituted or substituted with 1-3 substituents independently selected from the group consisting of $C_{1-4}$alkyl, $OC_{1-4}$alkyl, $CF_3$, $NO_2$ and halo. In still further embodiments of the present invention, $R^6$ is selected from the group consisting of $C_{1-4}$alkyl, $C_{3-5}$cycloalkyl, aryl and heteroaryl, wherein each of $C_{1-4}$alkyl, $C_{3-5}$cycloalkyl, aryl and heteroaryl are either unsubstituted or substituted with 1-2 substituents independently selected from the group consisting of $C_{1-4}$alkyl, $OC_{1-4}$alkyl, $CF_3$, $NO_2$ and halo. In further embodiments, $R^6$ is selected from the group consisting of $C_{1-4}$alkyl and aryl, wherein aryl is either unsubstituted or substituted with 1-2 substituents independently selected from the group consisting of $C_{1-4}$alkyl, $OC_{1-4}$alkyl, $CF_3$, $NO_2$ and halo. In further embodiments, $R^6$ is selected from the group consisting of $C_{1-4}$alkyl and phenyl, wherein phenyl is either unsubstituted or substituted with 1-2 substituents independently selected from the group consisting of $C_{1-4}$alkyl, $OC_{1-4}$alkyl, $CF_3$, $NO_2$ and halo. In still further embodiments, $R^6$ is a phenyl group either unsubstituted or substituted with 1-2 substituents independently selected from the group consisting of $CH_3$, $OCH_3$, $NO_2$, F and Cl. Further embodiments include compounds of Formula I wherein $R^6$ is an unsubstituted phenyl or phenyl substituted with 1 substituent independently selected from the group consisting of $CH_3$, $OCH_3$, $NO_2$, F and Cl. It is also an embodiment of the present invention that $R^6$ is t-butyl The present invention includes compounds of Formula I wherein $R^7$ is selected from the group consisting of H, $C_{1-6}$alkyl and $C(O)R^8$. In embodiments of the present invention, $R^7$ is H or $C_{1-4}$alkyl. In further embodiments, $R^7$ is H or $CH_3$. In still further embodiments of the present invention $R^7$ is H. In other embodiments of the present invention, $R^7$ is $C(O)R^8$.

The present invention includes compounds of Formula I wherein $R^7$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo. In embodiments of the invention, $R^8$ is selected from the group consisting of $C_{1-4}$alkyl, $C_{3-5}$cycloalkyl, aryl-$C_{1-2}$alkyl, aryl and heteroaryl, wherein each of $C_{1-4}$alkyl, $C_{3-5}$cycloalkyl, aryl and heteroaryl are either unsubstituted or substituted with 1-3 substituents independently selected from the group consisting of $C_{1-4}$alkyl, $OC_{1-4}$alkyl, $CF_3$, $NO_2$ and halo. In further embodiments of the present invention, $R^8$ is selected from the group consisting of $C_{1-4}$alkyl, $C_{3-5}$cycloalkyl, $PhCH_2$ and phenyl, wherein each of $C_{1-4}$alkyl, $C_{3-5}$cycloalkyl, $PhCH_2$ and phenyl are either unsubstituted or substituted with 1-2 substituents independently selected from the group consisting of $C_{1-4}$alkyl, $OC_{1-4}$alkyl, $CF_3$, $NO_2$, F and Cl. In still further embodiments of the present invention, $R^8$ is selected from the group consisting of $C_{1-4}$alkyl, $PhCH_2$ and phenyl, wherein each of $C_{1-4}$alkyl, $PhCH_2$ and phenyl are either unsubstituted or substituted with 1 substituent independently selected from the group consisting of $C_{1-4}$alkyl, $OC_{1-4}$alkyl, $CF_3$, $NO_2$, F and Cl. In even further embodiments, $R^8$ is selected from the group consisting of methyl, t-butyl, $PhCH_2$ and phenyl.

The present invention includes compounds of Formula I, wherein ===== represents a single or a double bond. It is an embodiment of the invention that the bond between C22 and C23 is a single bond. It is a further embodiment that the bond between C16 and C17 is a single bond. In a still further embodiment both the bond between C22 and C23 and the bond between C16 and C17 are single bonds.

In an embodiment of the present invention, when the bond between C16 and C17 is a double bond, $R^6$ is $C_{1-6}$alkyl and $R^7$ is selected from the group consisting of H and $C_{1-6}$alkyl.

All of the compounds of Formula I have more than one asymmetric centre. Where the compounds according to the invention possess more than one asymmetric centre, they may exist as diastereomers. It is to be understood that all such isomers and mixtures thereof in any proportion are encompassed within the scope of the present invention. The stereochemistry of the A, C and D rings and at the C20 position of the compounds of the invention is preferably that of natural 1α,25-dihydroxy vitamin $D_3$. The stereochemistry at the sulfoximine sulfur atom may be either R or S. Therefore the present invention provides compounds of Formula I, and pharmaceutically acceptable acid addition salts, hydrates, solvates and prodrugs thereof, having the following relative stereochemistry:

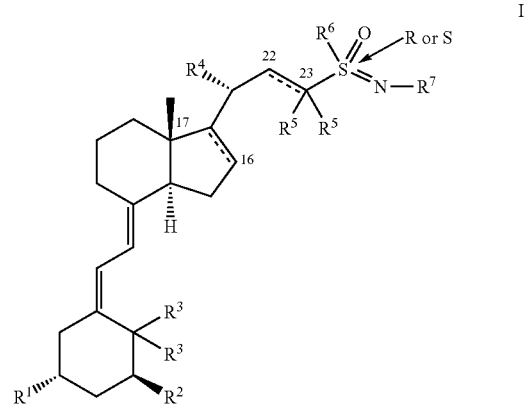

wherein $R^1$-$R^8$ and ===== are as defined above.

In a further embodiment of the present invention, the bond between C16 and C17 is a single bond and the compound of Formula I has the following relative stereochemistry:

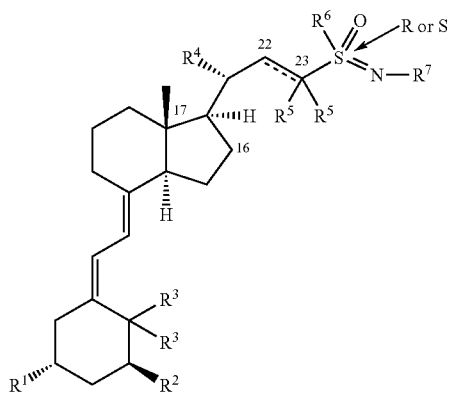

wherein $R^1$-$R^8$ and ----- are as defined above.

In a further embodiment of the present invention, when the bond between C22 and C23 is a double bond and the bond between C16 and C17 is a single bond, the compound of Formula I has the following relative stereochemistry:

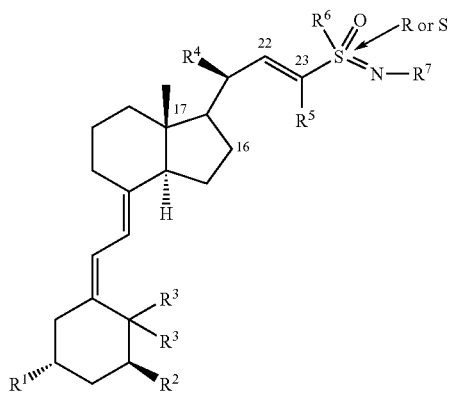

wherein $R^1$-$R^8$ and ----- are as defined above.

It is to be understood that, while the relative stereochemistry of the compounds of Formula I is preferably as shown above, such compounds of Formula I may also contain certain amounts (e.g. less than 20%, preferably less than 10%, more preferably less than 5%) of compounds of Formula I having alternate stereochemistry. For example, a compound of Formula I having the 1α,3β-stereochemistry of natural 1α,25-Dihydorxy Vitamin $D_3$, shown above, may contain less then 20%, preferably less then 10%, more preferably less then 5%, of a compound of Formula I having the unnatural 1β,3α-stereochemistry.

In specific embodiments of the present invention, the compounds of the invention include:

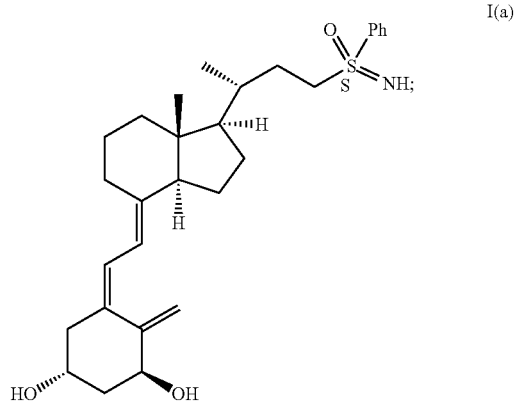

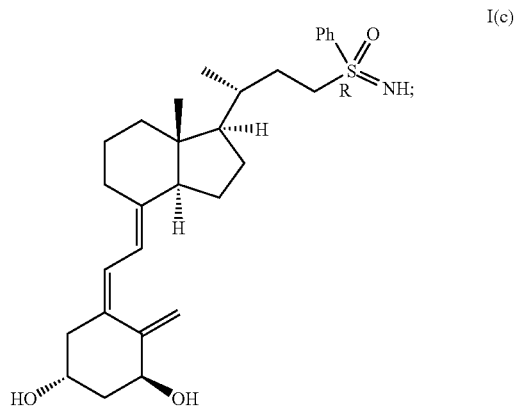

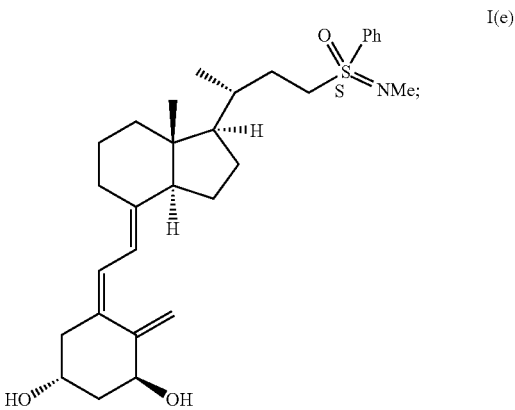

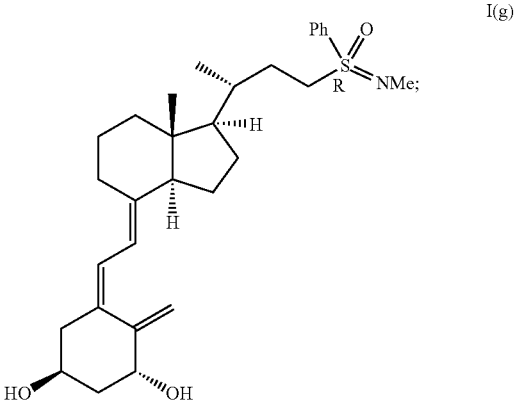

-continued
I(i)
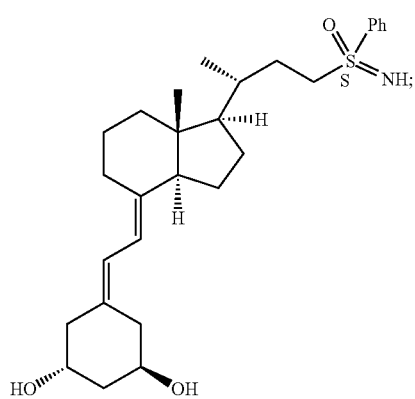
I(j)
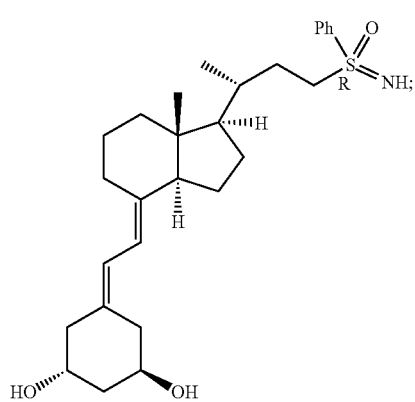
I(k)
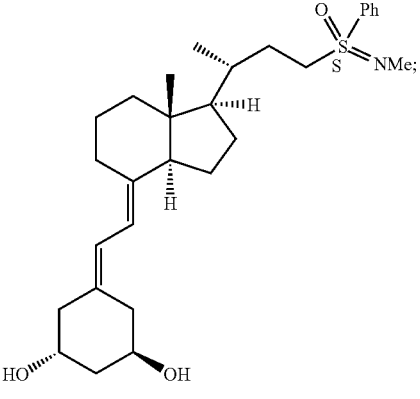
I(l)
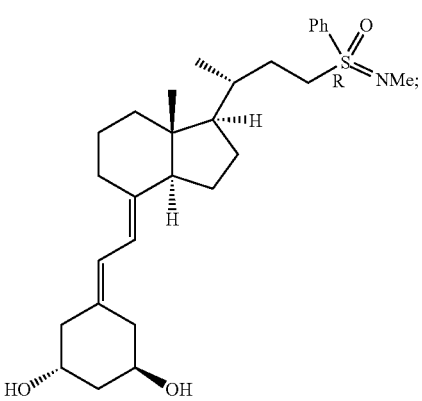
-continued
I(m)
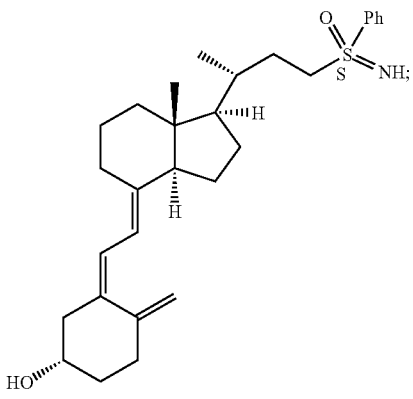
I(n)
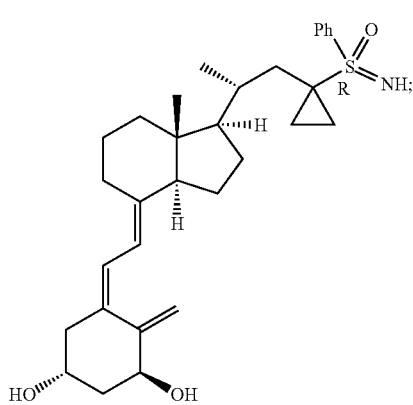
I(o)
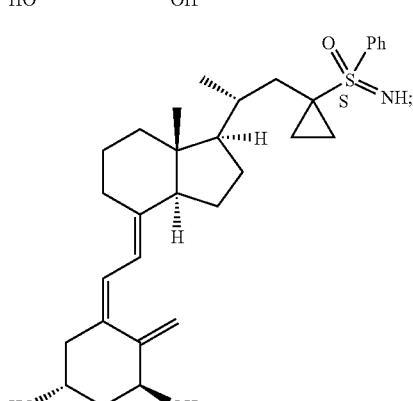
I(p)
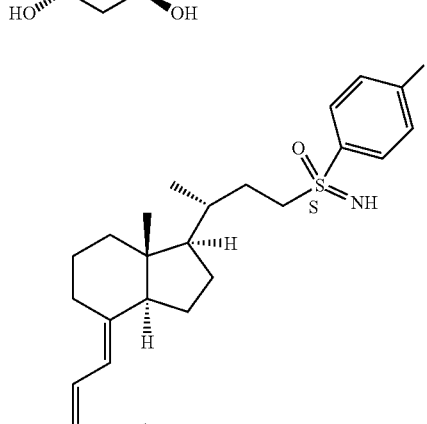

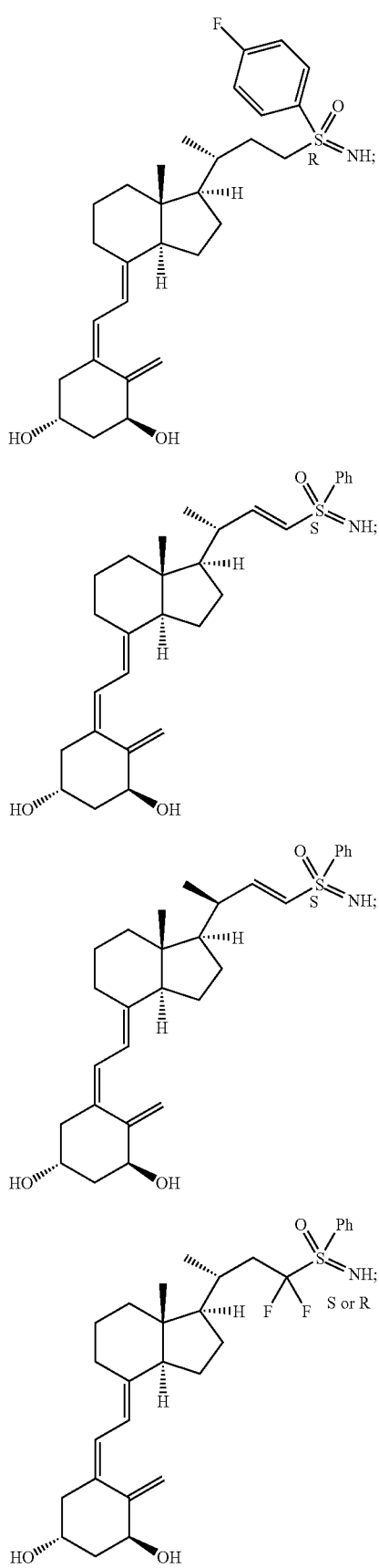

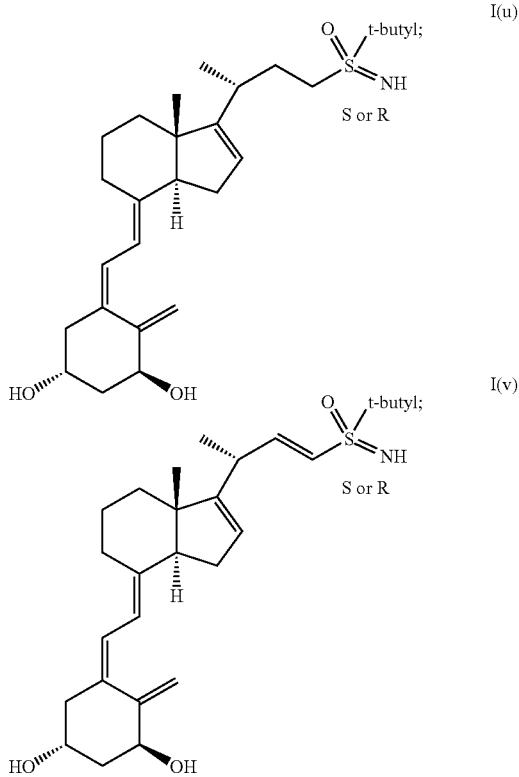

and pharmaceutically acceptable acid addition salts, hydrates, solvates and prodrugs thereof.

The present invention includes within its scope, prodrugs of the compounds of the invention. In general, such prodrugs will be functional derivatives of a compound of the invention which are readily convertible in vivo into the compound from which it is notionally derived. Conventional procedures for the selection and preparation of suitable prodrugs are described, for example, in "Design of Prodrugs" ed. H. Bundgaard, Elsevier, 1985.

The present invention includes radiolabeled forms of compounds of the invention, for example, compounds of the invention labeled by incorporation within the structure $^3$H or $^{14}$C or a radioactive halogen such as $^{125}$I.

III. Methods of Preparing Compounds of the Invention

In accordance with another aspect of the present invention, the compounds of the invention can be prepared by processes analogous to those established in the art. Therefore, compounds of this invention may be prepared, for example, by the reaction sequence shown in Scheme 1:

Scheme 1

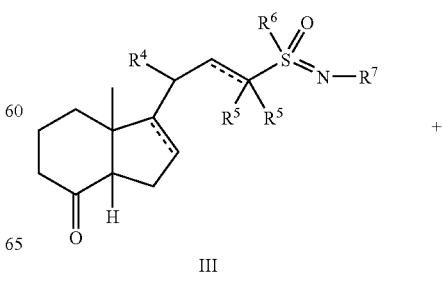

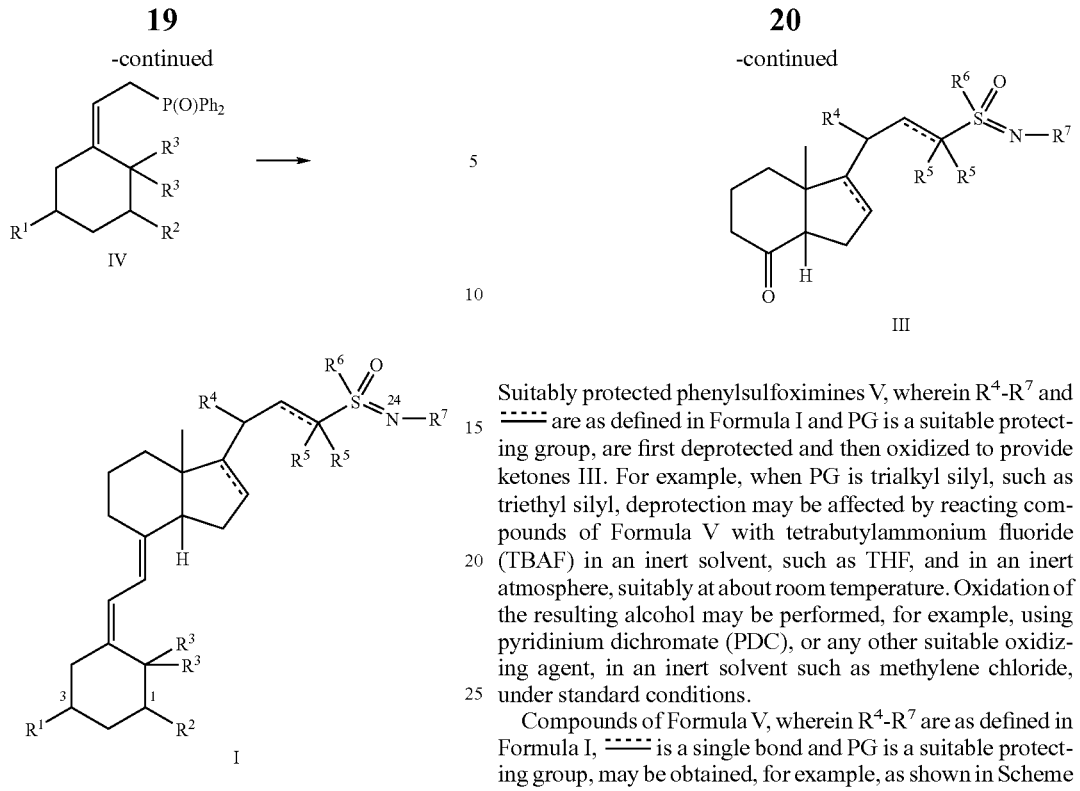

IV

I

Ketones of Formula III, wherein $R^4$-$R^7$ and ----- are as defined in Formula I, may be reacted with phosphine oxides of Formula IV, wherein $R^1$-$R^3$ are as defined in Formula I, under standard Horner-Wadsworth-Emmons (HWE) coupling conditions. Therefore phosphine oxides IV are treated with a strong base, for example an alkyl lithium such as n-butyl lithium, under anhydrous conditions in an inert atmosphere and solvent, for example tetrahydrofuran (THF), at temperatures in the range of about 60° C. to about −90° C., suitably at about −78° C. To the resulting intermediate phosphine oxide anion is added a cold, preferably at about −78° C., solution of a ketone III in an inert solvent such as THF while maintaining the anhydrous conditions. After removal of any protecting groups using standard chemistries (if needed), compounds of Formula I may be obtained.

Ketones of Formula III, wherein $R^4$, $R^5$, $R^6$ and $R^7$ are as defined in Formula I, may be prepared, for example, as shown in Scheme 2:

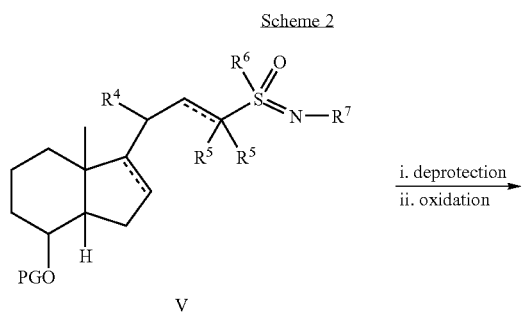

Suitably protected phenylsulfoximines V, wherein $R^4$-$R^7$ and ----- are as defined in Formula I and PG is a suitable protecting group, are first deprotected and then oxidized to provide ketones III. For example, when PG is trialkyl silyl, such as triethyl silyl, deprotection may be affected by reacting compounds of Formula V with tetrabutylammonium fluoride (TBAF) in an inert solvent, such as THF, and in an inert atmosphere, suitably at about room temperature. Oxidation of the resulting alcohol may be performed, for example, using pyridinium dichromate (PDC), or any other suitable oxidizing agent, in an inert solvent such as methylene chloride, under standard conditions.

Compounds of Formula V, wherein $R^4$-$R^7$ are as defined in Formula I, ----- is a single bond and PG is a suitable protecting group, may be obtained, for example, as shown in Scheme 3:

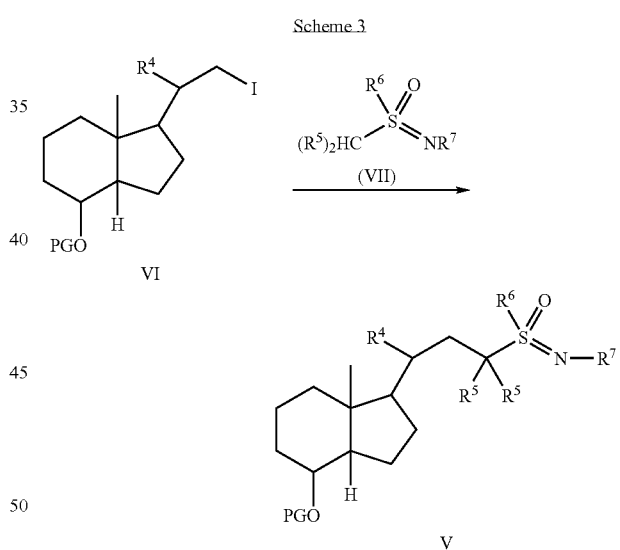

Compounds of Formula VI, wherein $R^4$ and ----- are as defined in Formula I and PG is a suitable protecting group may be reacted with the anion of compounds of Formula VII, wherein $R^5$-$R^7$ are as defined in Formula I under anhydrous conditions at temperatures in the range of about −60° C. to about −90° C., suitably at about −78° C. The anions of compounds of Formula VII may be prepared by treating compounds of Formula VII with a strong base, for example an alkyl lithium such as n-butyl lithium, under inert conditions and, in the presence, for example, of hexamethyl phosphoramide (HMPA) or $N^1$, $N,N^1,N^1$-tetramethy ethylenediamine (TMEDA). When $R^7$ is H, it is preferred for the sulfoximine nitrogen to be protected with a suitable protecting group, for example a tialkylsilane, which may be removed using standard techniques after the reaction of the compounds of Formula VI with the compounds of Formula VII.

Compounds of Formula V, wherein one or both of $R^5$ is fluoro, $R^4$, $R^6$, $R^7$ and ----- are defined in Formula I and PG is a suitable protecting group may also be prepared from compounds of Formula V, wherein both $R^5$ groups are H, by treatment of such compounds with one or two equivalents, either sequentially or together, of a strong base, such as an alkyllithium followed by a source of "F+", such as $(PhSO_2)_2NF$.

Compounds of Formula I, wherein $R^1$-$R^7$ and ----- between C16 and C17 are as defined in Formula I and ----- between C22 and C23 is a double bond, may be obtained, for example, as shown in Scheme 4:

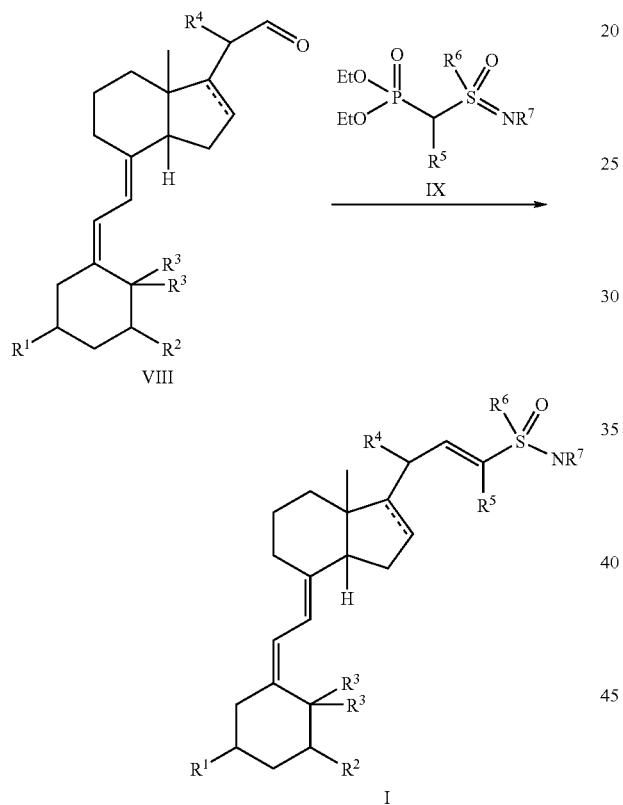

Compounds of Formula VIII, wherein $R^1$-$R^4$ and ----- are as defined in Formula I, may be reacted with the anion of compounds of Formula IX, wherein $R^5$-$R^7$ are as defined in Formula I, under anhydrous conditions at temperatures in the range of about −60° C. to about −90° C., suitably at about −78° C. The anions of compounds of Formula IX may be prepared by treating compounds of Formula IX with a strong base, for example, potassium t-butoxide, in an inert solvent, for example tetrahydrofuran, under anhydrous conditions at temperatures in the range of about −60° C. to about −90° C., suitably at about −78° C. When $R^7$ is H, it is preferred for the sulfoximine nitrogen in IX to be protected with a suitable protecting group, for example a trialkylsilane, which may be removed using standard techniques after the reaction of the compounds of Formula VIII with the compounds of Formula IX.

Compounds of Formula I, wherein $R^1$-$R^7$ and ----- between C16-C17 are as defined in Formula I and ----- between C22-C23 is a single bond, may also be prepared as shown in Scheme 5:

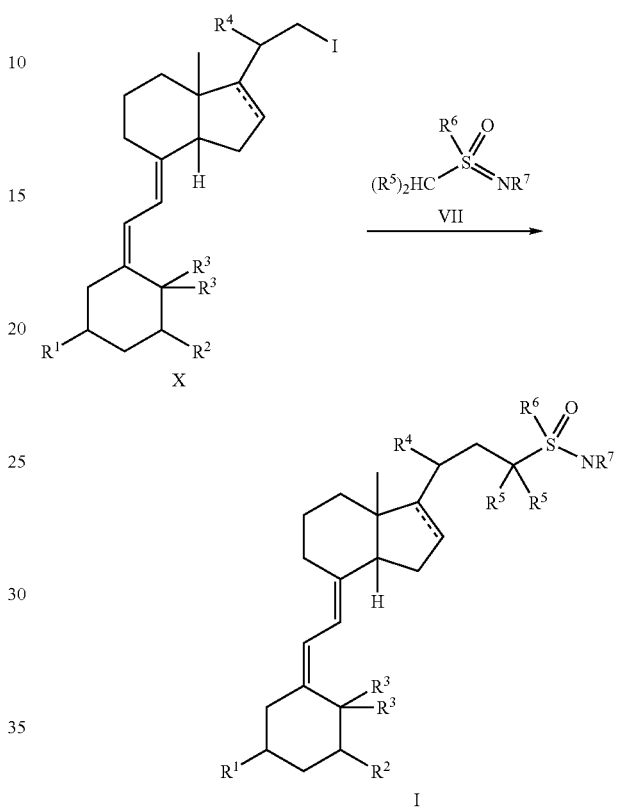

Compounds of Formula X, wherein $R^1$-$R^4$ and ----- are as defined in Formula I, may be reacted with the anion of compounds of Formula VII, wherein $R^5$-$R^7$ are as defined in Formula I under anhydrous conditions at temperatures in the range of about 60° C. to about −90° C., suitably at about −78° C. The anions of compounds of Formula VII may be prepared by treating compounds of Formula VII with a strong base, for example an alkyl lithium such as n-butyl lithium, under inert conditions and, in the presence, for example, of hexamethyl phosphoramide (HMPA) or $N_1,N,N^1,N^1$-tetramethyl-ethylenediamine (TMEDA). When $R^7$ is H, it is preferred for the sulfoximine nitrogen in VII to be protected with a suitable protecting group, for example a tialkylsilane, which may be removed using standard techniques after the reaction of the compounds of Formula X with the compounds of Formula VII.

Compounds of Formula VII, wherein $R^5$, $R^6$ and $R^7$ are as defined in Formula I are commercially available or may be prepared using methods known in the art (for the preparation of (±)-N,S-Dimethyl-S-phenylsulfoximine: see Johnson, C. R.; Haake, M.; Schroeck. *J. Am. Chem. Soc.* 1970, 92, 6594 and Shiner, C. S.; Berks, A. H. *J. Org. Chem.* 1988, 53, 5542; for the preparation of (i)-S-Methyl-S-Phenylsulfoximine: see Johnson, C. R.; Haake, M.; Schroeck. *J. Am. Chem. Soc.* 1970, 92, 6594; and for resolution see: Brandt, J.; Gais, H-J. *Tetrahedron; Asymmetry,* 1997, 8, 909 and Shiner, C. S.; Berks, A. H. *J. Org. Chem.* 1988, 53, 5542; for the preparation of S-(4-methyphenyl)-S-methylsulfoximine: see Johnson, Carl R.; Kirchhoff, Robert A.; Corkins, H. Glenn. *J. Org. Chem.* 1974, 39(16), 2458-9; for the preparation of S-(4-methoxyphenyl)-S-methylsulfoximine: see Akutagawa, Kunihiko; Furukawa, Naomichi; Oae, Shigeru. *Phosphorus Sulfur* 1984, 19(3), 369-74; for the preparation of S-(4-chlorophenyl)-S-methylsulfoximine: see Oae, S.; Harada, K.; Tsujihara, K.; Furukawa, N. *Int. J. Sulfur Chem., Part A* 1972, 2(1), 49-61; for the preparation of S-(4-nitrophenyl)-S-methylsulfoximine: see Oae, S.; Harada, K.; Tsujihara, K.; Furukawa, N. *Int. J. Sulfur Chem., Part A* 1972, 2(1), 49-61.

As an example, compounds of Formula VII, wherein $R^5$-$R^7$ are as defined in Formula I, may be prepared as shown in Scheme 6:

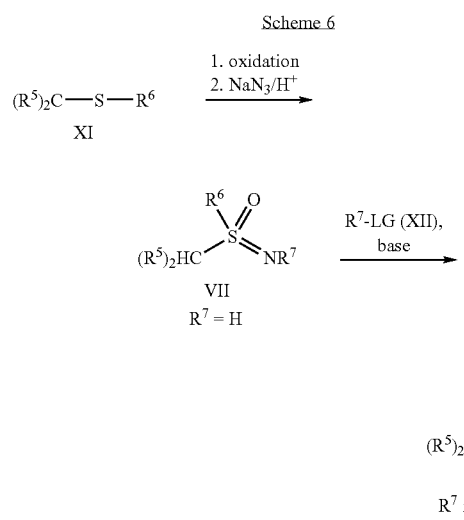

Sulfides of Formula XI, wherein $R^5$ and $R^6$ are as defined in Formula I may be oxidized to the corresponding sulfoxide using standard conditions, for example by treatment with one equivalent of mCPBA. This sulfoxide may then be treated with sodium azide and acid, for example sulfuric acid, in an inert solvent such as chloroform, at a temperature in the range of about −10° C. to about 25° C., suitably at about 0° C. Once the acid has been added to the reaction, the mixture may be allowed to room temperature and moderate heating may be used to push the reaction to completion. The resulting compound of Formula VII, wherein $R^7$ is H may be reacted with a compound of Formula XII, wherein $R^7$ is selected from $C_{1-6}$alkyl, C(O)Re (with $R^8$ being as defined in Formula I) or a suitable protecting group, for example a trialkylsilane, and LG is a suitable leaving group, for example halogen, in particular chlorine, under standard alkylation conditions to provide compounds of Formula VII wherein $R^7$ is selected from $C_{1-6}$alkyl, C(O)$R^8$ (with $R^8$ being as defined in Formula I) or a suitable protecting group.

Compounds of Formula IX, wherein $R^5$-$R^7$ are as defined in Formula I, may be prepared, for example, from a compound of Formula VII, wherein $R^5$-$R^7$ are as defined in Formula I, as shown in Scheme 7:

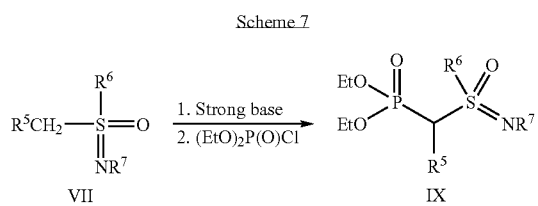

Compounds of Formula VII, wherein $R^5$-$R^7$ are as defined in Formula I, may be first treated with a strong base, for example an alkyl lithium, in an inert solvent, for example tetrahydrofuran, under anhydrous conditions at temperatures in the range of about 60° C. to about −90° C., suitably at about −78° C., followed by, for example, diethylchlorophosphate, also under anhydrous conditions at temperatures in the range of about 60° C. to about −90° C., suitably at about −78° C., to provide compounds of Formula IX, wherein $R^5$-$R^7$ are as defined in Formula I. When $R^7$ is H, it is preferred for the sulfoximine nitrogen in VII to be protected with a suitable protecting group, for example a tialkylsilane, which may be removed using standard techniques after the reaction of the compounds of Formula VII with the chlorophosphate.

An alternate route to compounds of Formula V, wherein $R^4$-$R^7$ and ---- are as defined in Formula I and PG is a suitable protecting group is shown in Scheme 8

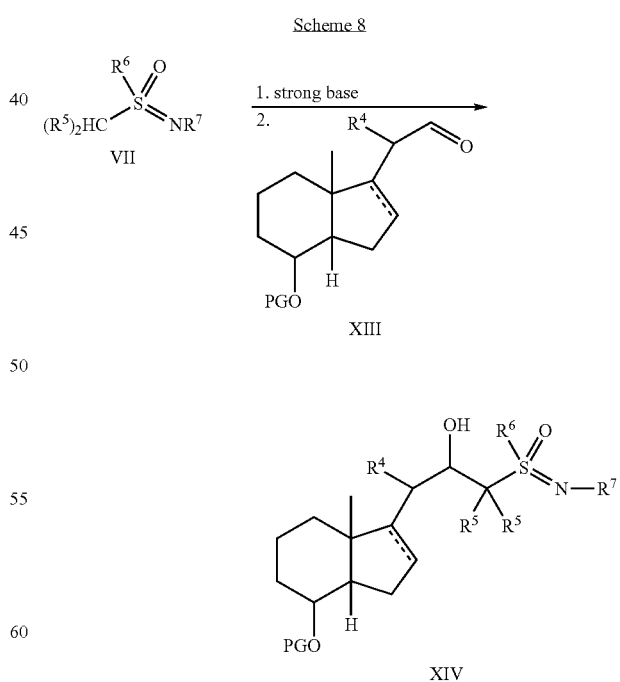

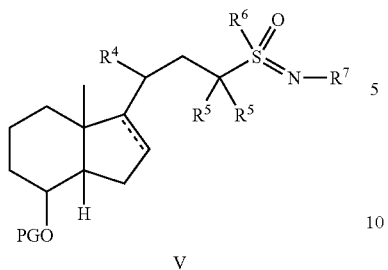

V

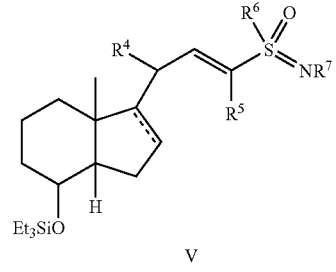

V

Compounds of Formula VII, wherein $R^5$-$R^7$ are as defined in Formula I (when $R^7$ is H, it is preferred that the H is replaced with a suitable protecting group, for example a trialkylsilane, for the above reaction sequence) may be treated with a strong base, for example an alkyl lithium, under anhydrous conditions at temperatures in the range of about −60° C. to about −90° C., suitably at about −78° C., followed by the addition of a compound of Formula XIII, wherein $R^4$ and ---- are as defined in Formula I and PG is a suitable protecting group, to provide compounds of Formula XIV, wherein $R^4$-$R^7$ and ---- are as defined in Formula I and PG is a suitable protecting group. The hydroxyl group at C22 of the compounds of Formula XIV may be removed using any known method, for example using free radical chemistry as shown in Scheme 8, to provide compounds of Formula V, wherein $R^4$-$R^7$ and ---- are as defined in Formula I and PG is a suitable protecting group. The above reaction scheme is especially useful for the preparation of compounds of Formula V where the bond between C16 and C17 is a double bond. Once again, when $R^7$ is H, it is preferred for the sulfoximine nitrogen in VII to be protected with a suitable protecting group, for example a tialkylsilane, which may be removed using standard techniques after completion of the above reaction sequence.

Compounds of Formula XIV, wherein $R^4$, $R^6$, $R^7$ and ---- are as defined in Formula I and at least one of $R^5$ is H, may also be used to prepare a compound of Formula V, wherein $R^4$, $R^6$, $R^7$ and ---- between C16 and C17 are as defined in Formula I, at least one of $R^5$ is H and ---- between C22 and C23 is a double bond, by treatment with acid under standard conditions as shown in Scheme 9. In the compounds shown below, it is an embodiment of the invention that $R^5$ is H.

Scheme 9

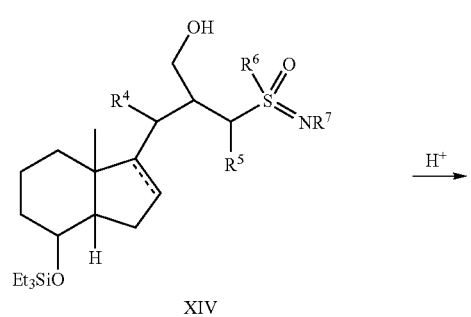

XIV

The preparation of compounds of Formula VI, wherein $R^4$ is as defined in Formula I and PG is a suitable protecting group, is known in the art. Therefore compounds of Formula VI may be prepared as described in Posner, G. H. et al. *J. Org. Chem.* 1997, 62, 3299-3314 the contents of which are incorporated herein by reference.

The preparation of compounds of Formula IV, wherein $R^1$ and $R^2$ are as defined in Formula I is known in the art. Therefore compounds of Formula IV may be prepared as described in Posner, G. H. et al. *J. Med. Chem.* 1992, 35, 3280-3287, the contents of which are incorporated herein by reference.

Compounds of Formula X, wherein $R^1$-$R^4$ and ---- are as defined in Formula I, may be prepared from the corresponding alcohol as reported by Manchand, S. M. et al. *J. Org. Chem.* 1995, 60, 6574-6581).

Compounds of Formula XIII, wherein $R^4$ is as defined in Formula I and ---- is a double bond may be prepared as described in Lars, K. L. et al. *J. Org. Chem.* 2003, 68, 1367-1374. The corresponding compounds where ---- is a single bond may be prepared by hydrogenation or reduction of the C16-C17 double bond using standard methodologies.

The preparation of enantiomerically pure compounds of Formula I may be accomplished by using enantiomerically pure compounds of Formula III and IV in the reaction shown in Scheme I. In this reaction, a mixture of the 1α,3β and 1β,3α diasteromers is typically obtained, with the 1α,3β diastereomer as the major product. These diasteromers may be separated using chromatography, for example using high performance liquid chromatography (HPLC).

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of the invention may be conventional esters formed with available hydroxy, thiol, amino or carboxyl group. For example, when $R^1$ and/or $R^2$ is OH in a compound of the invention, it may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters.

A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C.

IV. Uses

As hereinbefore mentioned, novel compounds of the Formula I have been prepared. Accordingly, the present invention includes all uses of the compounds of the invention including their use in therapeutic methods and compositions for modulating CYP24 activity, their use in diagnostic assays and their use as research tools.

Selectively inhibiting the cytochrome P450 enzymatic pathway, through which 1α,25-dihydroxy vitamin $D_3$ is catabolized (mainly via C-24 hydroxylation), is one important way to prolong the lifetime of this hormone, or analogs thereof. Therefore, the compounds of Formula I were tested in vitro, using a standard protocol, for their ability to inhibit specifically CYP24, an enzyme responsible for 24-hydroxylation of 1α,25-dihydroxy vitamin $D_3$. Antimycotic ketoconazole, a drug used clinically for chemotherapy of human prostate cancer (Trachtenberg, J. et al. J. Urol. 1984, J32, 61-63), was used as a control standard for inhibition of CYP24. Compounds I(a), I(c), I(e), I(g), I(i), I(j), I(k), I(l), I(m), I(n), I(o), I(p), I(q), I(r) and I(s) have been shown to selectively inhibit the CYP24.

By selectively modulating CYP24, the enzyme that metabolizes 1α,25-dihydroxy vitamin $D_3$, the levels of 1α,25-dihydroxy vitamin $D_3$ (either endogenous or administered as part of a chemotherapeutic regimen), or analogs thereof, may also be modulated. Diseases that benefit from a modulation, in particular an increase, of the levels of 1α,25-dihydroxy vitamin $D_3$ can therefore be treated using a modulator of CYP24. By acting preferentially on CYP24, side effects caused by interaction with other enzymes and receptors may be reduced. Accordingly, the present invention provides a method for treating diseases which benefit from a modulation, preferably an increase, of the levels of 1α,25-dihydroxy vitamin $D_3$, or an analog of 1α,25-dihydroxy vitamin $D_3$, comprising administering an effective amount of a compound of the invention to a cell or animal in need thereof. The invention also includes the use of a compound of the invention to treat diseases which benefit from a modulation, preferably an increase, of the levels of 1α,25-dihydroxy vitamin $D_3$, or an analog of 1α,25-dihydroxy vitamin $D_3$. Further, the invention includes a use of a compound of the invention to prepare a medicament to treat diseases which benefit from a modulation, preferably an increase, of the levels of 1α,25-dihydroxy vitamin $D_3$, or an analog of 1α,25-dihydroxy vitamin $D_3$.

Inhibition of CYP24 will inhibit the catabolism of 1α,25-dihydroxy vitamin $D_3$, or its analogs, which is expected to lengthen the biological lifetime of these compounds and thus allow smaller amounts of them to be used for effective disease treatment. Such smaller dosing is expected to avoid, or at least minimize, the hypercalcemic toxicity associated with medicinal use of 1α,25-dihydroxy vitamin $D_3$ and its analogs. Further, by inhibiting the catabolism of 1α,25-dihydroxy vitamin $D_3$, the compounds of the invention will increase the endogenous levels of this hormone, which will have similar beneficial therapeutic effects. Therefore, in an embodiment, the present invention provides a method for treating diseases which benefit from inhibiting the catabolism of 1α,25-dihydroxy vitamin $D_3$, or an analog of 1α,25-dihydroxy vitamin $D_3$, comprising administering an effective amount of a compound of the invention to a cell or animal in need thereof. The invention also includes the use of a compound of the invention to treat diseases which benefit from inhibiting the catabolism of 1α,25-dihydroxy vitamin $D_3$, or an analog of 1α,25-dihydroxy vitamin $D_3$. Further, the invention includes a use of a compound of the invention to prepare a medicament to treat diseases which benefit from inhibiting the catabolism of 1α,25-dihydroxy vitamin $D_3$, or an analog of 1α,25-dihydroxy vitamin $D_3$.

Diseases which will benefit for a modulation in the levels of 1α,25-dihydroxy vitamin $D_3$ include, but are not limited to:
  i. in the parathyroid—hyper- and hypo-parathyroidism, Osudohypo-parathyroidism, Secondary hyperparathyroidism;
  ii. in the pancreas—diabetes;
  iii. in the thyroid—medullary carcinoma;
  iv. in the skin psoriasis, wound healing;
  v. in the lung—sarcoidosis and tuberculosis;
  vi. in the kidney—chronic renal disease, hypophosphtatemic VDRR, vitamin D dependent rickets;
  vii. in the bone—anticonvulsant treatment, fibrogenisis imperfecta ossium, osteitits fibrosa cystica, osteomalacia, osteoporosis, osteopenia, osteosclerosis, renal osteodytrophy, rickets;
  viii. in the intestine—glucocorticoid antagonism, idopathic hypercalcemia, malabsorption syndrome, steatorrhea, tropical sprue; and
  ix. autoimmune disorders.

In embodiments of the invention, the disease that benefits from a modulation in the levels of 1α,25-dihydroxy vitamin $D_3$, or an analog of 1α,25-dihydroxy vitamin $D_3$, are selected from cancer, dermatological disorders (for example psoriasis), parathyroid disorders (for example hyperparathyroidism and secondary hyperparathyroidism), bone disorders (for example osteoporosis) and autoimmune disorders.

In accordance with a further aspect of the present invention, the disease that benefits from a modulation, in particular an increase, in the levels of 1α,25-dihydroxy vitamin $D_3$, or an analog of 1α,25-dihydroxy vitamin $D_3$, is a cell proliferative disorder. Accordingly, there is provided a method for modulating cell proliferation (preferably inhibiting cell proliferation) and/or promoting cell differentiation, comprising administering an effective amount of a compound of the invention to a cell or animal in need thereof. The invention also includes a use of a compound of the invention to modulate cell proliferation (preferably to inhibit cell proliferation) and/or to promote cell differentiation. The invention further includes a use of a compound of the invention to prepare a medicament to modulate cell proliferation (preferably to inhibit cell proliferation) and/or to promote cell differentiation.

In particular, the method of the invention is useful in inhibiting the proliferation of abnormal but not normal cells. Abnormal cells include any type of cell that is causative of or involved in a disease or condition and wherein it is desirable to modulate or to inhibit the proliferation of the abnormal cell, or to promote its differentiation, in order to treat the disease or condition. Examples of abnormal cells include malignant or cancerous cells as well as cells that over-proliferate in inflammatory conditions such as psoriasis.

In another embodiment of the present invention, the disease that benefits from a modulation, in particular an increase, in the levels of 1α,25-dihydroxy vitamin $D_3$, or an analog of 1α,25-dihydroxy vitamin $D_3$, is cancer. Accordingly, the present invention provides a method of treating cancer comprising administering an effective amount of a compound of the invention to a cell or animal in need thereof. The invention also includes a use of a compound of the invention to treat cancer. The invention further includes a use of a compound of the invention to prepare a medicament to treat cancer. In embodiments of the invention, the cancer is selected from the group consisting of breast cancer, lung cancer, prostate cancer, colon and colorectal cancer, kidney cancer, head and neck cancer, pancreatic cancer, skin cancer, Kaposi's sarcoma and leukemia.

In another aspect, the invention provides a method of modulating CYP24 activity in a cell by administering an effective amount of a compound of the invention. In a further aspect, the invention provides a method of inhibiting CYP24 activity in a cell by administering an effective amount of a compound of the invention. The present invention also provides a use of a compound of the invention to modulate, preferably to inhibit, CYP24 activity. The present invention further provides a use of a compound of the invention to prepare a medicament to modulate CYP24 activity, preferably to inhibit, CYP24 activity.

The compounds of the invention can be used alone or in combination with other agents that modulate CYP24 activity, or in combination with other types of treatment (which may or may not modulate CYP24) for diseases that benefit from a modulation, preferably an increase, in the levels of 1α,25-dihydroxy vitamin $D_3$, or analogs thereof, and/or an inhibition of the catabolism of 1α,25-dihydroxy vitamin $D_3$, or an analog thereof. Preferably the compounds of the invention are administered in combination with 1α,25-dihydroxy vitamin $D_3$ (calcitriol), an analog of 1α,25-dihydroxy vitamin $D_3$ or other vitamin D receptor agonists. Inhibiting catabolism of vitamin D receptor agonists such as 1α,25-dihydroxy vitamin $D_3$, or analogs thereof, will lengthen the biological lifetime or efficacy of these therapies and thus allow smaller amounts of the drug to be used for effective human chemotherapy; such smaller dosing will avoid, or at least minimize, the side effects, for example the hypercalcemic toxicity, associated with medicinal use of these compounds. The present invention therefore provides a method of increasing the efficacy of a vitamin D receptor agonist comprising co-administering an effective amount of a compound of the invention and an effective amount of the vitamin D receptor agonist. Further the invention includes the use of a compound of the invention to increase the efficacy of a vitamin D receptor agonist and a use of a compound of the invention to prepare a medicament to increase the efficacy of a vitamin D receptor agonist. In embodiments of the invention, the vitamin D receptor agonist is 1α,25-dihydroxy vitamin $D_3$, or an analog thereof. By analog of 1α,25-dihydroxy vitamin $D_3$, it is meant a chemically modified analog of 1α,25-dihydroxy vitamin $D_3$ which is a vitamin D receptor agonist and therefore exhibits a therapeutic profile similar to 1α,25-dihydroxy vitamin $D_3$. Examples of such compounds can be found in the following review articles, the contents of which are incorporated herein by reference: Pinette, K. V et al. "Vitamin D Receptor as a Drug Discovery Target", Mini Reviews in Med. Chem. 2003, 3:193-204; Mathieu, C. and Adorini, L. "The Coming of Age of 1,25-Dihydroxy Vitamin $D_3$ Analogs as Immunomodulatory Agents", Trends in Mol. Med. 2002, 8:174-179; Carlberg, C. "Molecular Basis of the Selective Activity of Vitamin D Analogues", J. Cell. Bio. 2003, 88:274-281; Stein, M. S. and Wark, J. D. "An update on the therapeutic potential of vitamin D analogues", Expert Opin. Invest. Drugs 2003, 12:825-840; Bouillon, R. et al. "Structure-Function Relationships in the Vitamin D Endocrine System" Endocr. Rev. 1995, 16:200-257; and Nagpal, S. et al. "Vitamin D Analogs: Mechanism of Action and Therapeutic Applications", Current Med. Chem. 2001, 8:1661-1679.

Treatments used in combination with the compounds of the present invention may be based on the disease type and do not have to specifically target CYP24 activity or the VDR. In a particular aspect of the present invention, the compounds of the invention are used in combination with other therapies and therapeutics to treat dermatological disorders, bone disorders, cancer and autoimmune disorders. Such therapies include, but are not limited to the following: for cancer: surgery, radiation, chemotherapies and biotherapies; for psoriasis: ultraviolet B radiation, chemotherapy and biotherapies.

One skilled in the art can determine which compounds of the invention would have therapeutic utility, for example, in inhibiting cell proliferation in any type of cancer or cell proliferative disorder. Compounds may be examined for their potency in inhibiting cell growth in cell proliferation assays such as inhibition of growth of murine keratinocyte cells (cell line PE) and for the inhibition of TPA-induced ornithine decarboxylase (ODC) activity as described in U.S. Pat. No. 5,830,885, the contents of which are incorporated herein by reference.

In addition to cancer, the compounds of the invention are useful in treating other conditions involving aberrant or abnormal cell proliferation. Other cell proliferative disorders that may be treated by the present invention include inflammatory diseases, allergies, autoimmune disease, graft rejection, psoriasis, restenosis, artherosclerosis, and any other disorder wherein it is desirable to inhibit, prevent or suppress cell growth. Compounds of the invention may be tested for their potency in a particular cell proliferation disorder using assays and techniques known to those of skill in the art. For example, the following references provide assays for various conditions: Rheumatoid Arthritis: "Regulation of IL-15—Simulated TNF-alpha Production by Rolipram", Journal of Immunology (1999) volume 163 page 8236 by C. S. Kasyapa et al.; Allergy: "A novel Lyn-Binding Peptide Inhibitor Blocks Eosinophil Differentiation, Survival, and Airway eosinophilic inflammation". Journal of Immunology (1999) volume 163 page 939 by T. Adachi et al.; Psoriasis: Journal of Immunology (2000) volume 165 page 224 "Inhibition of Keratinocyte apoptosis by IL-15: a new parameter in the pathegenosis of psoriasis" by R. Üchert; and Psoriasis: International Archives of allergy and Immunology (2000) Volume 123 page 275. "T-cell receptor mimic peptides and their potential application in T-cell mediated disease" by A. H. Enk.

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent or carrier. The present invention further comprises a pharmaceutical composition comprising a compound of the invention and a vitamin D receptor agonist in admixture with a suitable diluent or carrier. In embodiments of the invention, the vitamin D receptor agonist is 1α,25-dihydroxy vitamin $D_3$, or an analog thereof.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of the invention may be used in the form of the free base, in the form of solvates and as hydrates. All forms are within the scope of the invention.

In accordance with the methods of the invention, the described compounds or solvates thereof may be administered to a patient in a variety of forms depending on the selected route of administration, as will be understood by those skilled in the art. The compositions of the invention may be administered, for example, by oral, parenteral, buccal, sublingual, nasal, rectal, patch, pump or transdermal (topical) administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention thereof may be orally administered, for example, with an inert diluent or with an assimilable edible carder, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990-18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists. Ampoules are convenient unit dosages.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compositions for topical administration may include, for example, propylene glycol, isopropyl alcohol, mineral oil and glycerin. Preparations suitable for topical administration include liquid or semi-liquid preparations such as liniments, lotions, applicants, oil-in-water or water-in-oil emulsions such as creams, ointments or pastes; or solutions or suspensions such as drops. In addition to the aforementioned ingredients, the topical preparations may include one or more additional ingredients such as diluents, buffers, flavouring agents, binders, surface active agents, thickeners, lubricants, preservatives, e.g. methyl hydroxybenzoate (including antioxidants), emulsifying agents and the like.

Sustained or direct release compositions can be formulated, e.g. liposomes or those wherein the active compound is protected with differentially degradable coatings, such as by microencapsulation, multiple coatings, etc. It is also possible to freeze-dry the compounds of the invention and use the lypolizates obtained, for example, for the preparation of products for injection.

The compounds of the invention may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. For example, in the topical treatment, ointments, creams, or lotions containing from 1-1000 μg/g of a compound of the invention may be administered. Oral preparations may be formulated, preferably as tablets, capsules, or drops, containing from 0.5-1000 μg of a compound of the invention, per dosage unit. The compounds of the invention may be administered initially in a suitable dosage that may be adjusted as required, depending on the clinical response. For ex vivo treatment of cells over a short period, for example for 30 minutes to 1 hour or longer, higher doses of compound may be used than for long term in vivo therapy.

In addition to the above-mentioned therapeutic uses, the compounds of the invention are also useful in diagnostic assays, screening assays and as research tools.

In diagnostic assays the compounds of the invention may be useful in identifying or detecting a cell proliferative disorder. In such an embodiment, the compounds of the invention may be radiolabelled (as hereinbefore described) and contacted with a population of cells. The presence of the radiolabel on the cells may indicate a cell proliferative disorder.

In screening assays, the compounds of the invention may be used to identify other compounds that modulate cell proliferation or CYP24 activity. As research tools, the compounds of the invention may be used in receptor binding assays and assays to study the localization of CYP24. In such assays, the compounds may also be radiolabelled.

The following non-limiting examples are illustrative of the present invention:

EXAMPLES

Materials and Methods for Examples 1-20

Unless otherwise noted, all reactions were performed in oven-dried glassware stirred under an atmosphere of ultra-high-purity argon. THF was distilled from Na/benzophenone ketyl and $CH_2Cl_2$ was distilled from $CaH_2$ immediately prior to use. Organolithiums were titrated prior to use following known methods (Suffert, J. *J. Org. Chem.* 1989, 54, 509-512). All other reagents were used as received from commercial suppliers. Analytical TLC analysis was conducted on precoated glass-backed silica gel plates (Merck Kieselgel 60 $F_{254}$, 250 mm thickness) and visualized with p-anisaldehyde or $KMnO_4$ stains. Flash column chromatography was performed as reported by Still et al. *J. Org. Chem.* 1978, 43, 1404, on flash silica gel (particle size 230-400 mesh). Medium Pressure Liquid Chromatography (MPLC) was performed with FMI pump and prepacked silica gel column (Merck, Labor Columns, LiChroprep Si 60, 40-63 mm). HPLC was carried out using a Rainin HPLX™ system equipped with two 25-mL/min preparative pump heads using (1) a Chiral Technologies CHIRALCEL® OJ 10-mm×250-mm (semipreparative) column packed with cellulose tris(4-methylbenzoate) on a 10 μm silica-gel substrate or (2) a Phenomenex LUNA™ 10-mm×250-mm (semipreparative) column packed with 110 Å silica gel (5 μm pore size) as C-18-bonded silica and a Rainin Dynamax™ UV-C dual-beam variable-wavelength detector set at 254 nm. Yields are reported for pure products (>95% based on their chromatographic and spectroscopic homogeneity) and are unoptimized. Melting points were determined in open capillaries using a Mel-Temp metal-block apparatus and are uncorrected. Optical rotations were measured at the Na line using a JASCO, P-1100 model polarimeter (Japan Spectroscopic Co.). NMR spectra were obtained on a Varian XL-400 spectrometer operating at 400 MHz for $^1H$, 376 MHz for $^{19}F$, and 100 MHz for $^{13}C$ and a Bruker 300 AMX spectrometer operating at 300 MHz for $^1H$. Chemical shifts are reported in ppm (δ) and are referenced to $CDCl_3$ (7.26 ppm for $^1H$ and 77.0 ppm for $^{13}C$), tetramethylsilane (TMS, 0.00 ppm for $^1H$), and $CFCl_3$ (0.00 ppm for $^{19}F$). IR spectra were obtained using a Perkin Elmer 1600 Series FT-IR instrument. HRMS (high resolution mass spectra) were obtained at the mass spectrometry facility at the Ohio State University on a Micromass QTOF Electrospray mass spectrometer. (−)-(R)-N-trimethylsilyl-S-methyl-S-phenyl sulfoximine and (+)-(S)-N-trimethylsilyl-S-methyl-S-phenyl sulfoximine were prepared as previously reported (see Hwang, K-J. *J. Org. Chem.* 1986, 51, 99-101. b) Hwang, K-J.; Logusch, E. W.; Brannigan, L. *J. Org. Chem.* 1987, 52, 3435-3441. N-alkylation of S-methyl-S-phenylsulfoximine was carried out as previously reported (see Johnson, C. R.; Layergne, O. M. *J. Org. Chem.* 1993, 58, 1922, and Raguse, B.; Ridley, D. D. Aust. *J. Chem.* 1986, 39, 1655). (−)-(R)-S-methyl-S-phenyl sulfoximine, (+)-(S)-S-methyl-S-phenyl sulfoximine, (−)-(R)-N,S-dimethyl-S-phenyl sulfoximine and (+)-(S)-N,S-dimethyl-S-phenyl sulfoximine were obtained from commercial sources.

Example 1

General Procedure for the Preparation of Compounds of the Formula V, Wherein $R^7$ is Hydrogen and C22-C23 is a Single Bond A flame-dried 10-mL recovery flask equipped with a magnetic stir bar, a reflux condenser a septum along with an Ar balloon was charged with the appropriate sulfoximine VII (50 mg, 0.32 mmol) and dissolved in 0.6 mL anhydrous acetonitrile to give 0.5 M solution. Then the flask was placed into an oil bath at 60° C. To this solution was added $Et_2NTMS$ (72 μL, 0.38 mmol) via a syringe dropwise over several minutes. After the addition was complete, the mixture was allowed to stir at 60° C. for ca. 30 minutes. When thin layer chromatography (TLC) showed total consumption of the starting material, the flask cooled down to room temperature. The mixture was concentrated in vacuo to give the N-trimethylsilyl sulfoximine product, essentially pure as determined by $^1H$ NMR, This was used without further purification.

A flame-dried 10-mL recovery flask equipped with a magnetic stir bar, a septum along with an Ar balloon was charged with the appropriate N-trimethylsilyl sulfoximine VII (73 mg, 0.32 mmol) dissolved in 3.2 mL freshly distilled THF and 0.32 mL HMPA. Then the flask was cooled down to −78° C. in an isopropanol/dry ice bath. To this solution was added 0.23 mL of n-BuLi (0.33 mmol, 1.44 M solution in hexanes) dropwise over several minutes during which time a pale yellow color developed. This mixture was allowed to stir at −78° C. for an additional 30 min, then warmed up to 0° C. for 10 min. The flask was recooled to −78° C. Meanwhile, a flame-dried 10-mL pear shaped flask equipped with a septum along with an Ar balloon was charged with iodide (+)-VI (50 mg, 0.11 mmol) dissolved in 0.5 mL freshly distilled THF and cooled down to −78° C. in an isopropanol/dry ice bath. The solution of iodide (+)-VI was transferred into the flask containing the lithiated sulfoximine at −78° C. via cannula over several minutes. After the addition was complete, the mixture was gradually warmed up to room temperature and stirred at this temperature for about 10 hours. TLC showed the complete consumption of starting material. The reaction was quenched by addition of 2 mL 3N aqueous HCl and allowed to stir for 30 minutes. The mixture was diluted with diethyl ether and basified by using 1N aqueous NaOH until pH becomes about 9, then rinsed into a separatory funnel with diethyl ether. The mixture was extracted with diethyl ether (3×25 mL). The combined extracts were washed with water (1×25 mL), and brine solution (1×25 mL), dried over $Na_2SO_4$ and filtered. The filtrate was concentrated in vacuo to give the crude product that was purified by flash column chromatography.

a) Triethylsilyl protected alcohol (+)-V(a). According to the general procedure for the preparation of compounds of the formula V, wherein $R^7$ is a hydrogen described above, (+)-(S)-S-methyl-S-phenyl sulfoximine VII(a) gave a compound of the formula (+)-V(a) as shown in Scheme 10:

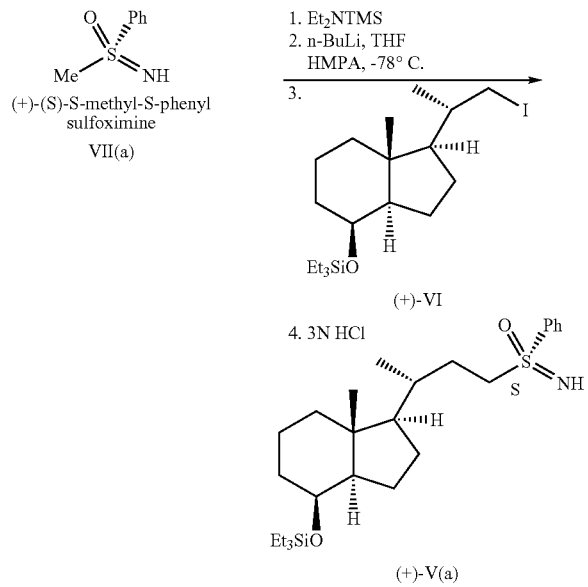

Flash column chromatography eluted with 50% ethyl acetate in hexanes afforded 28 mg of (+)-V(a) in 53% yield. Data for (+)-V(a): $[\alpha]^{25}{}_D$=+43.4 (c=1.4, CHCl$_3$) $^1$H NMR (CDCl$_3$, 400 MHz): δ 7.98-7.93 (m, 2H), 7.64-7.50 (m, 3H), 4.0 (d, 1H, J=Hz), 3.20 (ddd, 1H, J=4.4 Hz, J=12.4 Hz, J=13.6 Hz), 3.02 (ddd, 1H, J=4.4 Hz, J=11.6 Hz, J=13.6 Hz), 2.67 (br, 1H), 1.86 (d, 1H, J=12.4 Hz), 1.80-1.63 (m, 4H), 1.56-1.4 (m, 3H), 1.36-1.26 (m, 3H), 1.20-1.00 (m, 4H), 0.93 (t, 9H, J=8.4 Hz), 0.84 (s, 3H), 0.83 (d, 3H, J=6.8 Hz), 0.54 (q, 6H, J=8.4 Hz). $^{13}$C NMR (CDCl$_3$, 100 MHz): δ 141.9, 132.9, 129.1, 128.3, 69.2, 55.9, 54.8, 52.9, 42.1, 40.6, 34.5, 34.1, 28.6, 26.9, 22.8, 18.3, 17.6, 13.4, 6.9, 4.9. IR (Thin Film) 3271 (br, w), 2949 (s), 2875 (s), 1445 (m), 1224 (br, s), 1163 (m), 1091 (sh, m), 1017 (br, s), 742 (m) cm$^{-1}$. HRMS: calculated for $C_{26}H_{45}NO_2SSiNa^+$ [M+Na]: 486.2832 Found: 486.2829.

b) Triethylsilyl protected alcohol (+)-V(a'). According to the general procedure for the preparation of compounds of the formula V, wherein $R^7$ is a hydrogen described above, (−)-(R)—S-methyl-S-phenyl sulfoximine VII(a') gave a compound of the Formula (+)-V(a') as shown in Scheme 11:

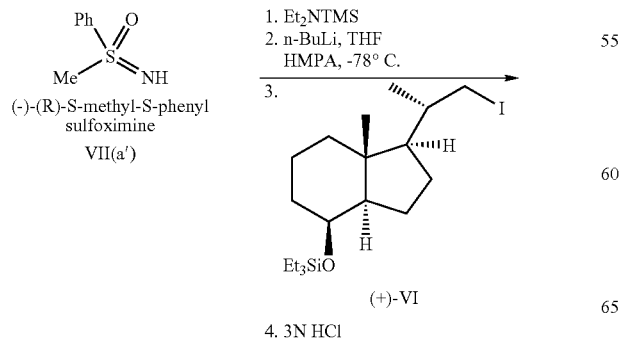

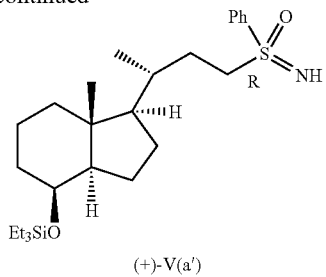

Flash column chromatography eluted with 50% ethyl acetate in hexanes afforded 38 mg of alkylation product (+)-V(a') as a viscous oil in 72% yield. Data for (+)-V(a'): $[\alpha]^{25}{}_D$=+37.1 (c=1.8, CHCl$_3$) $^1$H NMR (CDCl$_3$, 400 MHz): δ 7.97-7.93 (m, 2H), 7.64-7.49 (m, 3H), 4.0 (d, 1H, J=2.0 Hz), 3.17 (ddd, 1H, J=4.8, 12.4, 13.6 Hz), 3.06 (ddd, 1H, J=4.4, 12.0, 13.6 Hz), 2.68 (s, br, 1H), 1.88-1.71 (m, 3H), 1.66-1.44 (m, 4H), 1.42-1.25 (m, 4H), 1.19-1.00 (m, 4H), 0.93 (t, 9H, J=8.0 Hz), 0.84 (s, 3H), 0.83 (d, 3H, J=6.8 Hz), 0.53 (q, 6H, J=8.0 Hz). $^{13}$C NMR (CDCl$_3$, 100 MHz): δ 141.8, 132.9, 129.1, 128.3, 69.2, 55.8, 54.7, 52.9, 42.1, 40.6, 34.5, 34.1, 28.6, 26.9, 22.8, 18.3, 17.5, 13.4, 6.9, 4.9. IR (Thin Film) 3283 (br, w), 2948 (s), 2874 (s), 1445 (m), 1222 (br, s), 1163 (m), 1092 (sh, m), 1017 (br, s), 973 (br, m), 742 (m) cm$^{-1}$. HRMS: calculated for $C_{26}H_{45}NO_2SSiNa^+$ [M+Na]: 486.2832 Found: 486.2825.

Example 2

General Procedure for the Preparation of C,D-Ring Ketones III, wherein $R^7$ is Hydrogen and C22-C23 is a Single Bond

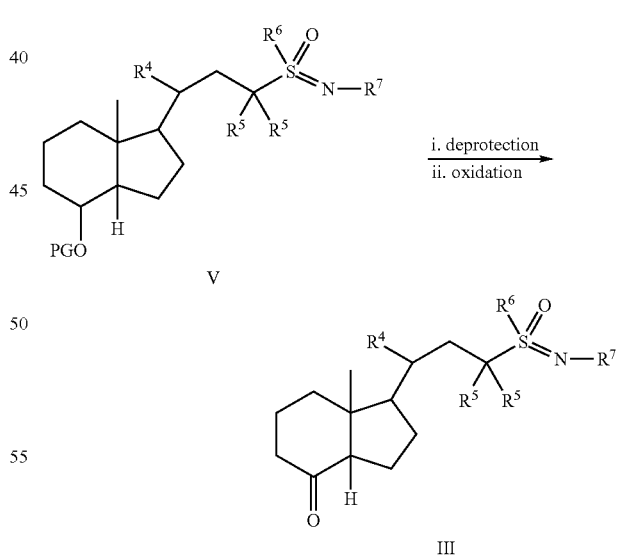

General Deprotection Method

An argon purged 5 mL polypropylene vial equipped with a magnetic stir bar, a septum along with an Ar balloon was charged with appropriate triethylsilyl protected alcohol (30 mg, 0.065 mmol) dissolved in 1.6 mL anhydrous acetonitrile to give ca. 0.04 M solution. To this well-stirred solution was added 0.26 mL of HF (0.46 mmol, 49% aqueous solution) via syringe at room temperature and the mixture was then allowed to stir at room temperature in the dark for 4 hours. TLC showed the completion of the reaction. This reaction mixture was diluted with ether (25 mL) and saturated solution of NaHCO$_3$ was added until no more carbon dioxide was liberated. The reaction mixture was then rinsed into a separatory funnel with ethyl acetate and was extracted with ethyl acetate (4×25 mL). The combined extracts were washed with water (1×25 mL) and brine solution (1×25 mL), dried over Na$_2$SO$_4$ and filtered. The filtrate was concentrated in vacuo to give the crude product.

General Oxidation Method

A flame-dried 10-mL recovery flask equipped with a magnetic stir bar, a septum along with an Ar balloon was charged with the appropriate alcohol (15 mg, 0.043 mmol) dissolved in 1 mL freshly distilled CH$_2$Cl$_2$ to give ca. 0.04 M solution. Then to this solution were added PDC (34 mg, 0.09 mmol) and 21 mg of oven-dried Celite in one portion at room. The resulting mixture was allowed to stir at room temperature for about 12 hours. TLC showed the complete consumption of starting material. The mixture was directly purified by column chromatography.

Example 2(a)

Preparation of CD-Ring Ketone(+)-III(a)

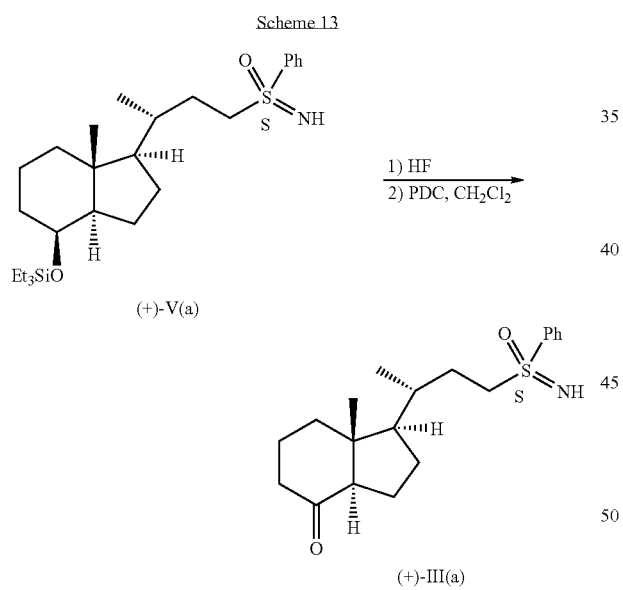

A solution of triethylsilyl protected alcohol (+)-V(a) (30 mg, 0.065 mmol) dissolved in 1.6 mL anhydrous acetonitrile was prepared to give ca. 0.04 M solution. To this well-stirred solution was added 0.26 mL of HF (0.46 mmol, 49% aqueous solution) via syringe at room temperature and the mixture was then allowed to stir at room temperature in the dark for 4 hours. TLC showed the completion of the reaction. This reaction mixture was diluted with ether (25 mL) and saturated solution of NaHCO$_3$ was added until no more carbon dioxide was liberated. The reaction mixture was then rinsed into a separatory funnel with ethyl acetate and was extracted with ethyl acetate (4×25 mL). The combined extracts were washed with water (1×25 mL) and brine solution (1×25 mL), dried over Na$_2$SO$_4$ and filtered. The filtrate was concentrated in vacuo to give the crude product. Flash column chromatography eluted with 100% ethyl acetate afforded 19.4 mg of the corresponding alcohol as a viscous oil in 86% yield. Data for the corresponding alcohol: $[\alpha]^{25}_D$=+30.2 (c=1.45, CHCl$_3$) $^1$H NMR (CDCl$_3$, 400 MHz): δ 7.97-7.95 (m, 2H), 7.64-7.53 (m, 3H), 4.05 (br, 1H), 3.20 (d 1H, J=4.4, 12.0, 13.6 Hz), 3.03 (ddd, 1H, J=4.4, 12.0, 13.6 Hz), 2.67 (s, br, 1H), 1.93-1.68 (m, 6H), 1.58-1.37 (m, 5H), 1.30-0.95 (m, 5H), 0.87 (s, 3H), 0.84 (d, 3H, J=6.4 Hz). $^{13}$C NMR (CDCl$_3$, 100 MHz): δ 141.9, 132.9, 129.1, 128.3, 69.0, 55.8, 54.8, 52.4, 41.8, 40.2, 34.1, 33.5, 28.5, 26.8, 22.3, 18.2, 17.3, 13.4. IR (Thin Film) 3436 (br, w), 3330 (br, w), 2934 (s), 2871 (s), 1445 (m), 1373 (w), 1219 (br, s), 1161 (w), 1097 (sh, m), 989 (s), m), 753 (s) cm$^{-1}$. HRMS: calculated for C$_{20}$H$_{31}$NO$_2$SNa$^+$ [M+Na]: 372.1967 Found: 372.1968.

The corresponding alcohol (15 mg, 0.043 mmol) dissolved in 1 mL freshly distilled CH$_2$Cl$_2$ to give ca. 0.04 M solution. Then to this solution was added PDC (34 mg, 0.09 mmol) and 21 mg of oven-dried Celite in one portion at room. The resulting mixture was allowed to stir at room temperature for about 12 hours. TLC showed the complete consumption of starting material. The mixture was directly purified by column chromatography. Flash column chromatography eluted with 100% ethyl acetate afforded 12 mg of ketone (+)-III(a) in 81% yield. Data for (+)-III(a): $[\alpha]^{25}_D$=+9.2 (c=0.4, CHCl$_3$) $^1$H NMR (CDCl$_3$, 400 MHz): δ 7.98-7.95 (m, 2H), 7.65-7.54 (m, 3H), 3.21 (ddd, 1H, J=4.4, 12.0, 13.6 Hz), 3.04 (ddd, 1H, J=4.4, 12.0, 13.6 Hz), 2.67 (s, 1H), 2.42 (dd, 1H, J=8.0 Hz, J=11.6 Hz), 2.30-2.16 (m, 2H), 2.05-1.95 (m, 2H), 1.93-1.65 (m, 5H), 1.60-1.35 (m, 4H), 1.27-1.19 (m, 1H), 0.91 (d, 3H, J=6.4 Hz), 0.58 (s, 3H). $^{13}$C NMR (CDCl$_3$, 100 MHz): δ 211.6, 141.9, 133.0, 129.2, 128.3, 61.7, 55.9, 54.7, 49.7, 40.8, 38.8, 34.4, 28.6, 27.2, 23.9, 18.9, 18.4, 12.4. IR (Thin Film) 3271 (w), 2942 (s), 2872 (s), 1701 (s), 1437 (sh, m), 1378 (w), 1219 (br, s), 1102 (w), 978 (m), 755 (w) cm$^{-1}$. HRMS: calculated for C$_{20}$H$_{29}$NO$_2$SNa$^+$ [M+Na]: 370.1811 Found: 370.1793.

Example 2(b)

Preparation of CD-Ring Ketone (+)-III(a')

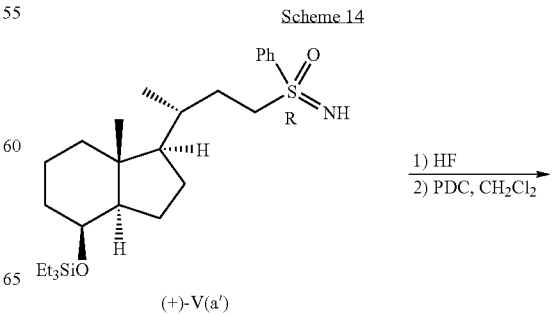

-continued

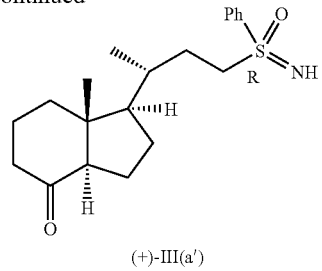

(+)-III(a')

A solution of triethylsilyl protected alcohol (+)-V(a') (30 mg, 0.065 mmol) dissolved in 1.6 mL anhydrous acetonitrile was prepared to give ca. 0.04 M solution. To this well-stirred solution was added 0.26 mL of HF (0.46 mmol, 49% aqueous solution) via syringe at room temperature and the mixture was then allowed to stir at room temperature in the dark for 4 hours. TLC showed the completion of the reaction. This reaction mixture was diluted with ether (25 mL) and saturated solution of $NaHCO_3$ was added until no more carbon dioxide was liberated. The reaction mixture was then rinsed into a separatory funnel with ethyl acetate and was extracted with ethyl acetate (4×25 mL). The combined extracts were washed with water (1×25 mL) and brine solution (1×25 mL), dried over $Na_2SO_4$ and filtered. The filtrate was concentrated in vacuo to give the crude product. Flash column chromatography eluted with 100% ethyl acetate afforded 20.1 mg of the corresponding alcohol as a viscous oil in 89% yield. Data for the corresponding alcohol: $[\alpha]^{25}_D$=+23.7 (c=1.45, $CHCl_3$) $^1$H NMR ($CDCl_3$, 400 MHz): δ 7.99-7.96 (m, 2H), 7.66-7.54 (m, 3H), 4.07 (br, 1H), 3.19 (ddd, 1H, J=4.8, 12.4, 13.6 Hz), 3.07 (ddd, 1H, J=4.4, 11.6, 13.6 Hz), 2.68 (s, br, 1H), 1.95-1.78 (m, 4H), 1.75-1.62 (m, 2H), 1.58-1.36 (m, 5H), 1.32-0.95 (m, 5H), 0.89 (s, 3H), 0.87 (d, 3H, J=6.4 Hz). $^{13}$C NMR ($CDCl_3$, 100 MHz): δ 141.9, 132.9, 129.1, 128.3, 69.0, 55.7, 54.7, 52.4, 42.8, 40.2, 34.1, 33.5, 28.5, 26.8, 22.3, 18.2, 17.3, 13.4. IR (Thin Film) 3448 (br, w), 3330 (br, w), 2935 (s), 2871 (s), 1445 (m), 1219 (br, s), 1098 (sh, m), 1078 (br, s), 990 (s), m), 753 (s) $cm^{-1}$. HRMS: calculated for $C_{20}H_{31}NO_2SNa^+$ [M+Na]: 372.1967 Found: 372.1981.

The corresponding alcohol (15 mg, 0.043 mmol) dissolved in 1 mL freshly distilled $CH_2Cl_2$ to give ca. 0.04 M solution. Then to this solution was added PDC (34 mg, 0.09 mmol) and 21 mg of oven-dried Celite in one portion at room. The resulting mixture was allowed to stir at room temperature for about 12 hours. TLC showed the complete consumption of starting material. The mixture was directly purified by column chromatography. Flash column chromatography eluted with 100% ethyl acetate afforded 13 mg of ketone (+)-III(a') in 87% yield. Data for (+)-III(a'): $[\alpha]^{25}_D$=+8.0 (c=0.4, $CHCl_3$) $^1$H NMR ($CDCl_3$, 400 MHz): δ 7.98-7.95 (m, 7.54 (m, 3H), 3.18 (ddd, 1H, J=4.8, 12.0, 13.6 Hz), 3.08 (ddd, 1H, J=4.8, 12.0, 13.6 Hz), 2.67 (s, 1H), 2.41 (dd, 1H, J=7.6 Hz, J=10.8 Hz), 2.30-2.16 (m, 2H), 2.06-1.95 (m, 2H), 1.93-1.80 (m, 2H), 1.78-1.64 (m, 3H), 1.57-1.33 (m, 4H), 1.27-1.19 (m, 1H), 0.92 (d, 3H, J=6.8 Hz), 0.59 (s, 3H). $^{13}$C NMR ($CDCl_3$, 100 MHz): δ 211.6, 141.9, 133.0, 129.1, 128.3, 61.7, 55.8, 54.6, 49.7, 40.8, 38.8, 34.4, 28.6, 27.1, 23.9, 18.9, 18.4, 12.4. IR (Thin Film) 3271 (w), 2954 (s), 2872 (s), 1701 (s), 1443 (sh, m), 1219 (br, s), 1096 (s), 978 (m), 749 (w) $cm^{-1}$. HRMS: calculated for $C_{20}H_{29}NO_2SNa^+$ [M+Na]: 370.1811 Found: 370.1809.

Example 3a

24-Phenyl Sulfoximines I(a) and I(b)

Scheme 15

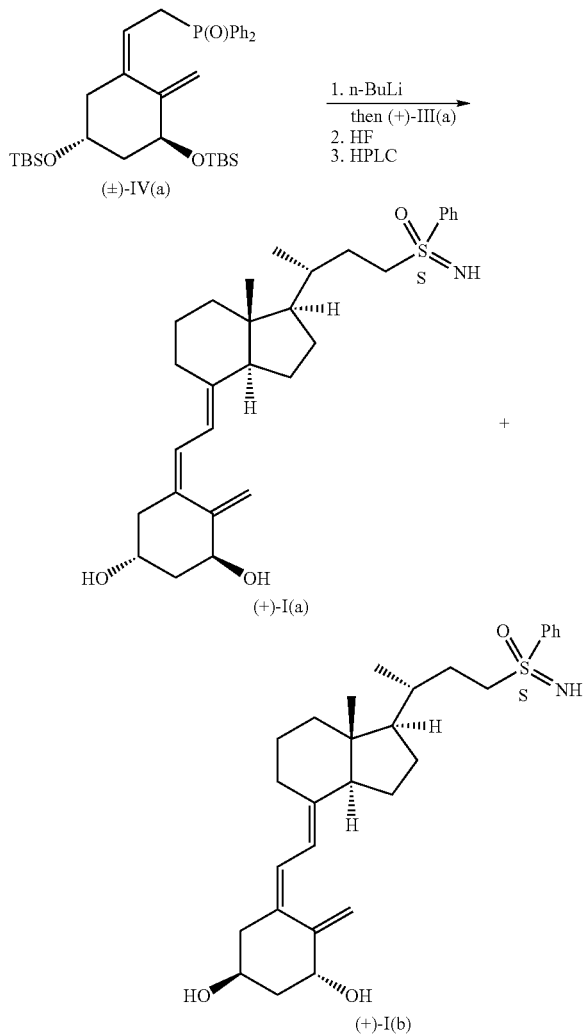

Prior to reaction, the phosphine oxide (+)-IV(a) (Posner, G. H. et al. *J. Med. Chem.* 1992, 35, 3280-3287) and CD-ring ketone (+)-III(a) were azeotrophically dried with benzene and left under vacuum for 48 h. Under argon, the phosphine oxide (±)-IV(a) (65 mg, 0.11 mmol) was dissolved in 1.1 mL freshly distilled THF to give ca. 0.1 M solution in a flame-dried 10 mL flask, and the flask was cooled down to −78° C. in an isopropanol/dry ice bath. To this solution was added n-BuLi (68 μL, 0.11 mmol, 1.6 M solution in hexanes) dropwise over several minutes during which time a deep red color developed and persisted. This mixture was allowed to stir at −78° C. for an additional 10 min. Meanwhile, a flame-dried 10-mL recovery flask equipped with a magnetic stir bar, a septum along with an Ar balloon was charged with CD-ring ketone (+)-III(a) (12 mg, 0.036 mmol) dissolved in 1 mL freshly distilled THF and cooled down to −78° C. in an isopropanol/dry ice bath. The solution of CD-ring ketone was gently transferred dropwise into the flask containing the phoshine oxide anion at −78° C. via cannula over several minutes. After the addition was complete, the deep red color persisted and the mixture was allowed to stir at 78° C. for ca. 15 hours during which time it was visually checked. Upon observation of the light yellow color, the reaction was quenched at −78° C. by addition of 5 mL of pH 7 buffer and allowed to come to room temperature. The mixture was then rinsed into a separatory funnel with ethyl acetate and extracted with ethyl acetate (3×25 mL). The combined extracts were washed with water (1×25 mL) and brine solution (1×25 mL), dried over $Na_2SO_4$ and filtered. The filtrate was concentrated in vacuo to give the crude product which was purified by column chromatography eluted with 50% ethyl acetate in hexanes in the presence of 1% triethylamine to afford the coupled product.

The coupled product (13 mg, 0.018 mmol) in a 5 mL argon purged polypropylene vial equipped with a magnetic stir bar was dissolved in 0.9 mL anhydrous acetonitrile to give ca. 0.02 M solution. To this well-stirred solution was added 75 μL of HF (1.8 mmol, 49% aqueous solution) via syringe at room temperature and the mixture was then allowed to stir at room temperature in the dark for 2 hours. TLC showed the completion of the reaction. The reaction mixture was diluted with ether (25 mL) and saturated solution of $NaHCO_3$ was added until no more carbon dioxide was liberated. The reaction mixture was then rinsed into a separatory funnel with ethyl acetate and was extracted with ethyl acetate (5×25 mL). The combined extracts were washed with water (1×25 mL), and brine solution (1×25 mL), dried over $Na_2SO_4$ and filtered. The filtrate was concentrated in vacuo to give the crude product that was purified by column chromatography.

Flash column chromatography eluted with 99% ethyl acetate in the presence of 1% triethylamine to afford 8.4 mg of a mixture of diastereomers (+)-I(a) and (+)-I(b) in 92% yield and in a ratio of 2.5:1 respectively. The diastereomeric mixture was then separated by HPLC using a Chiralcel OJ column (Semipreparative (1×25 cm), flow rate=2.0 mL/min) eluted with 13% ethanol in hexanes to afford 1.9 mg (+)-I(a) and 1.0 mg (+)-I(b) in 21% and 11% yields, respectively. The retention time for (+)-I(a) was 58.1 min, and for (+)-I(b) was 45.7 min.

Data for (+)-I(a): $[\alpha]_D$=+80.4 (c=0.13, MeOH) $^1$H NMR (CDCl$_3$, 400 MHz): δ 7.98-7.96 (m, 2H), 7.64-7.52 (m, 3H), 6.36 (d, 1H, J=11.2 Hz), 5.99 (d, 1 Hz), 5.32 (t, 1H, J=1.6 Hz) 4.98 (br, 1H), 4.43-4.40 (m, 1H), 4.23-4.22 (m, 1H) (ddd, 1H, J=4.4, 12.4, 13.2 Hz), 3.03 (ddd, 1H, J=4.8, 12.4, 13.2 Hz), 2.82-2.78 (m, 1H), 2.65 (s, 1H), 2.61-2.58 (m, 1H), 2.33-2.28 (m, 1H) 2.04-1.90 (m, 4 (m, 2H), 1.69-1.42 (m, 8H), 1.28-1.20 (m, 4H), 0.88 (d, 3H, J=6.4 Hz), 0.49 (s, 3H). $^{13}$C NMR (CD3OD, 100 MHz): δ 149.9, 142.3, 140.8, 136.0, 135.2, 130.7, 129.9, 124.9, 119.3, 112.2, 71.6, 67.5, 57.5, 57.2, 55.5, 47.0, 46.2, 43.8, 41.8, 36.4, 30.3, 30.0, 28.4, 24.7, 23.3, 19.1, 12.4. IR: 3387 (br, m), 3307 (br, m) 2942 (s), 2872 (m), 1443 (m), 1349 (w), 1213 (s), 1096 (m), 1055 (s), 1008 (m), 984 (sh, s), 749 (s) cm$^{-1}$. HRMS: calculated for $C_{29}H_{41}NO_3SNa^+$ [M+Na]: 506.2699. Found: 506.2668. Data for (+)-I(b): $[\alpha]_D$=+9 (c=0.09, MeOH) $^1$H NMR (CDCl$_3$, 400 MHz): δ 7.98-7.96 (m, 2H), 7.64-7.52 (m, 3H), 6.37 (d, 1H, J=11.6 Hz), 5.98 (d, 1H, J=11.6 Hz), 5.31 (m, 1H) 4.98 (br, 1H), 4.43-4.41 (m, 1H), 4.23-4.19 (m, 1H), 3.23-317 (m, 1H) 3.07-2.99 (m, 1H), 2.83-2.80 (m, 1H), 2.66 (s, 1H), 2.62-2.60 (m, 1H), 2.32-2.27 (m, 1H) 2.00-1.90 (m, 5H), 1.81-1.64 (m, 7H), 1.25-1.21 (m, 6H), 0.87 (d, 3H, J=6.8 Hz), 0.48 (s, 3H). $^{13}$C NMR (CD$_3$OD, 100 MHz): δ 149.8, 142.4, 142.2, 135.9, 130.5, 129.8, 124.9, 124.9, 119.2, 112.4, 71.7, 67.5, 57.2, 55.8, 47.0, 46.4, 43.8, 41.8, 36.4, 30.5, 30.0, 28.4, 24.7, 23.4, 19.1, 12.4. IR: 3320 (br, m), 3307, 2940 (s), 2871 (m), 1445 (m), 1349 (w), 1214 (s), 1093 (m), 1053 (s), 1008 (m), 984 (sh, s), 749 (s) cm$^{-1}$. HRMS: calculated for $C_{29}H_{41}NO_3SNa^+$ [M+Na]: 506.2699. Found: 506.2690.

Example 3b

24-Phenyl Sulfoximines I(c) and I(d)

In a like manner, compounds I(c) and I(d) can be prepared as shown in Scheme 16:

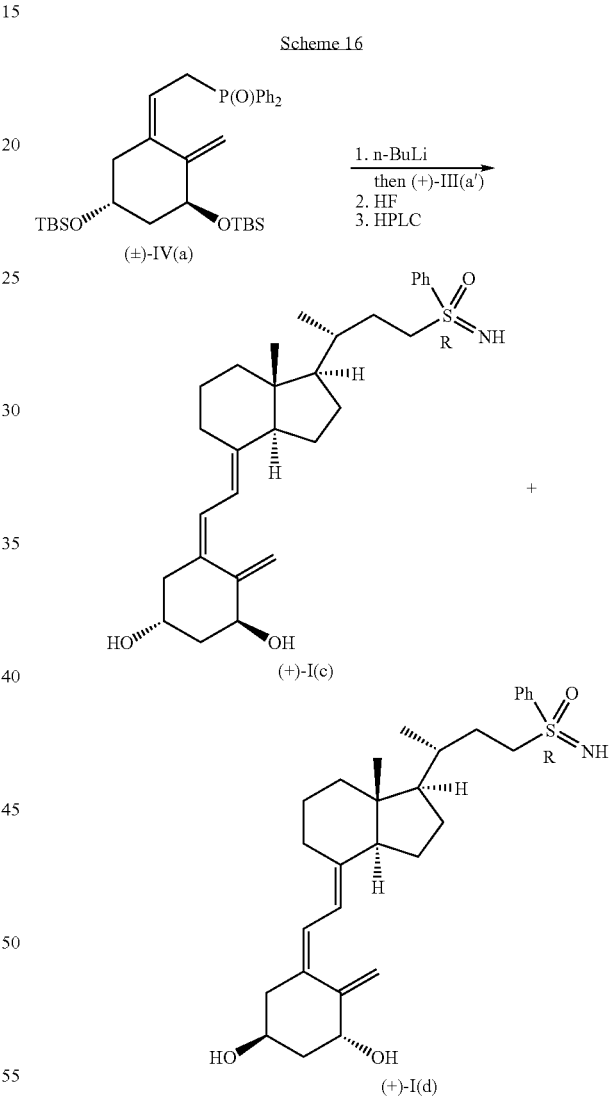

wherein CD-ring ketone (+)-III(a') instead of CD-ring ketone (+)-III(a) is coupled with phospine oxide (±)IV(a) as disclosed in example 3a above. After the coupling reaction and the subsequent deprotection step, flash column chromatography eluted with 99% ethyl acetate in the presence of 1% triethylamine afforded 7.2 mg of a mixture of diastereomers (+)-I(c) and (+)-I(d) in 82% yield and in a ratio of 2.9:1 respectively. The diastereomeric mixture was then separated by HPLC using Chiralcel OJ column (Semipreparative (1×25 cm), flow rate=2.0 mL/min) eluted with 13% ethanol in hexanes to afford 2.2 mg (+)-I(c) and 1.0 mg (+)-I(d) in 25% and 11% yields, respectively. The retention time for (+)-I(c) was 49.2 min. and for (+)-I(d) was 40.2 min.

Data for (+)-I(c): $[\alpha]_D$=+37.3 (c=0.13, MeOH) $^1$H NMR (CDCl$_3$, 400 MHz): δ 7.98-7.95 (m, 2H), 7.65-7.52 (m, 3H), 6.36 (d, 1H, J=11.6 Hz), 5.99 (d, 1H, J=11.2 Hz), 5.31 (m, 1H) 4.98 (br, 1H), 4.43-4.40 (m, 1H), 4.29-4.22 (m, 1H), 3.18 (ddd, 1H, J=4.8, 12.4, 14.0 Hz), 3.07 (ddd, 1H, J=4.8, 12.4, 14.0 Hz), 2.83-2.80 (m, 1H), 2.66 (s, 1H), 2.61-2.58 (m, 1H), 2.33-2.28 (m, 1H) 2.20-1.80 (m, 6H), 1.75-1.62 (m, 4H), 0.88 (d, 3H, J=6.4 Hz), 0.49 (s, 3H). $^{13}$C NMR (CDCl$_3$, 100 MHz): δ 147.6, 142.5, 133.2, 129.6, 128.6, 128.2, 124.8, 117.3, 111.8, 70.8, 66.8, 56.1, 55.7, 54.1, 45.9, 45.2, 42.8, 40.3, 34.9, 28.9, 28.2, 27.2, 23.4, 22.1, 18.5, 11.9. IR: 3377 (br, m), 3318 (br, m), 2931 (s), 2872 (m), 1442 (m), 1214 (s), 1096 (m), 1055 (s), 1008 (m), 984 (sh, s), 749 (s) cm$^{-1}$. HRMS: calculated for C$_{29}$H$_{41}$NO$_3$SNa$^+$ [M+Na]: 506.2699. Found: 506.2676.

Data for (+)-Id: $[\alpha]_D$=+17.5 (c=0.09, MeOH) $^1$H NMR (CDCl$_3$, 400 MHz): δ 7.98-7.95 (m, 2H), 7.64-7.52 (m, 3H), 6.37 (d, 1H, J=11.2 Hz), 5.98 (d, 1H, J=11.2 Hz), 5.31 (m, 1H) 4.98 (br, 1H), 4.43-4.41 (m, 1H), 4.22-4.19 (m, 1H), 3.16 (ddd, 1H, J=4.4, 12.0, 13.2 Hz), 3.08 (ddd, 1H, J=4.4, 12.4, 13.2 Hz), 2.82-2.80 (m, 1H), 2.66 (s, 1H), 2.62-2.58 (m, 1H), 2.31-2.27 (m, 1H) 1.91-1.80 (m, 4H), 1.74-1.60 (m, 10H), 1.30-1.19 (m, 4H), 0.88 (d, 3H, J=6.4 Hz), 0.50 (s, 3H). $^{13}$C NMR (CDCl$_3$ MHz): δ Due to insufficient amount, $^{13}$C was not obtained. IR: 3307 (br, m), 2919 (s), 2860 (m), 1443 (m), 1219 (s), 1090 (m), 1055 (s), 984 (sh, s), 749 (s) cm$^{-1}$. HRMS: calculated for C$_{29}$H$_{41}$NO$_3$SNa$^+$ [M+Na]: 506.2699. Found: 506.2673.

Example 4

General Procedure for the Preparation of Compounds of the Formula V, Wherein R$^7$ is Not Hydrogen and C22-C23 is a Single Bond A flame-dried 10 mL recovery flask equipped with a magnetic stir bar, a septum along with an Ar balloon was charged with the appropriate sulfoximine VII (see scheme 3) (43 mg, 0.25 mmol) and dissolved in 1.7 mL freshly distilled THF and 0.17 mL HMPA. Then the flask was cooled down to −78° C. in an isopropanol/dry ice bath. To this solution was added 0.156 mL of n-BuLi (0.25 mmol, 1.6 M solution in hexanes) dropwise over several minutes during which time a pale yellow color developed. This mixture was allowed to stir at −78° C. for an additional 30 min, then 0° C. for 10 min. The flask was recooled to −78° C. Meanwhile, a flame-dried 10 mL pear shaped flask equipped with a septum along with an Ar balloon was charged with iodide VI (see scheme 3) (37 mg, 0.0845 mmol) which was dissolved in 0.5 mL freshly distilled THF and cooled down to −78° C. in an isopropanol/dry ice bath. The solution of iodide VI was transferred into the flask containing the lithiated sulfoximine at −78° C. via cannula over several minutes. After the addition was complete, the mixture was gradually warmed up to room temperature and then stirred for about 4 hours. TLC showed the complete consumption of starting material. The reaction was quenched by addition of 5 mL distilled water and then rinsed into a separatory funnel with ethyl acetate. The mixture was extracted with ethyl acetate (3×25 mL). The combined extracts were washed with water (1×25 mL), and brine solution (1×25 mL), dried over Na$_2$SO$_4$ and filtered. The filtrate was concentrated in vacuo to give the crude product that was purified by flash column chromatography.

a) Triethylsilyl protected alcohol (+)-V(b). According to the general procedure for the preparation of compounds of the formula V, wherein R$^7$ is not a hydrogen described above, (+)-(S)—N,S-dimethyl-S-phenyl sulfoximine VII(b) gave a compound of the formula V(b) as shown in Scheme 17:

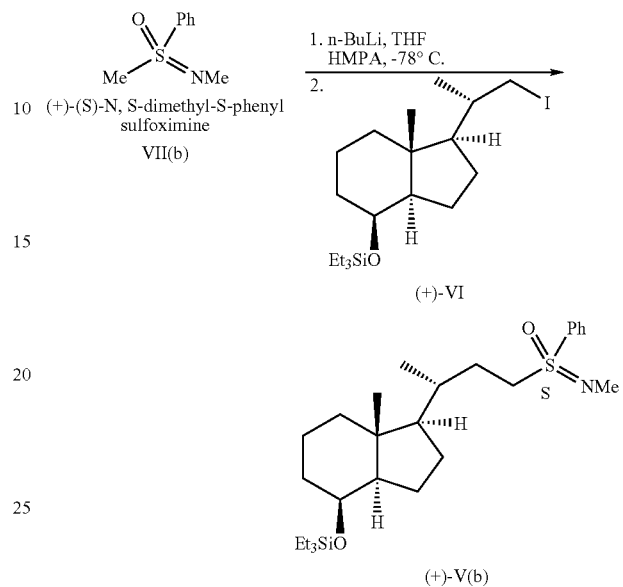

Flash column chromatography eluted with 30% ethyl acetate in hexanes afforded 32.4 mg of (+)-V(b) in 80% yield. Data for (+)-V(b): $[\alpha]^{25}_D$=+82.69 (c=0.3, CHCl$_3$) $^1$H NMR (CDCl$_3$, 400 MHz): δ 7.84-7.81 (m, 2H), 7.61-7.52 (m, 3H), 3.98 (d, 1H, J=4.0 Hz), 3.20 (ddd, 1H, J=4.8 Hz, J=5.2 Hz, J=12.4 Hz), 2.98 (ddd, 1H, J=4.4 Hz, J=4.4 Hz, J=12.4 Hz), 2.65 (s, 3H), 1.85-1.60 (m, 6H), 1.56-1.23 (m, 6H), 1.17-0.98 (m, 3H), 0.91 (t, 6H, J=7.6 Hz), 0.80 (s, 3H), 0.79 (d, 3H, J=6.4 Hz), 0.51 (q, 9H, J=8.0 Hz). $^{13}$C NMR (CDCl$_3$, 100 MHz): δ 137.54, 132.71, 129.31, 69.20, 55.92, 53.88, 52.93, 42.09, 40.62, 34.48, 34.23, 29.53, 28.11, 26.94, 22.81, 18.26, 17.57, 13.43, 6.91, 4.88. IR (Thin Film) 2950 (s), 2875 (s), 1445 (sh, m), 1490 (m), 1246 (br, s), 1149 (m), 1082 (sh, m), 1020 (m), 846 (w) cm$^{-1}$. HRMS: calculated for C$_{27}$H$_{47}$NO$_2$SSiNa$^+$ [M+Na]: 500.2988 Found: 500.2998.

b) Triethylsilyl protected alcohol (−)-V(b'). According to the general procedure for the preparation of compounds of the formula V, wherein R$^7$ is not a hydrogen described above, (−)-(R)—N,S-dimethyl-S-phenyl sulfoximine VII(b') gave a compound of the formula V(b') as shown in Scheme 18:

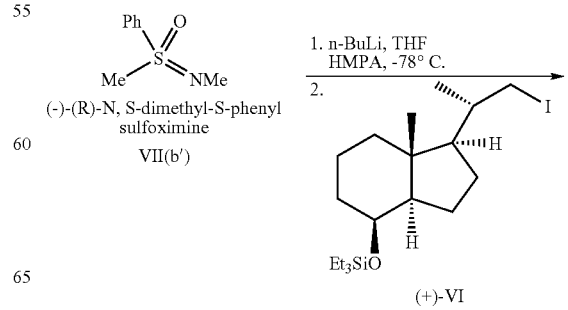

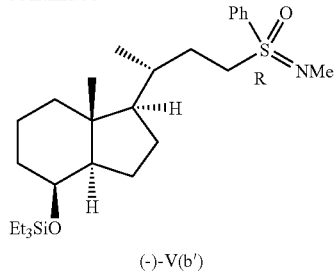

(−)-V(b')

Flash column chromatography eluted with 30% ethyl acetate in hexanes afforded 35 mg of alkylation product (−)-V(b') as a viscous oil in 86% yield. Data for (−)-V(b'): $[\alpha]^{25}_D=-5.92$ (c=0.3, CHCl$_3$) $^1$H NMR (CDCl$_3$, 400 MHz): δ 7.85-7.83 (m, 2H), 7.63-7.54 (m, 3H), 3.99 (d, 1H, J=2.4 Hz), 3.18-3.02 (m, 2H), 2.66 (s, 3H), 1.88-1.44 (m, 8H), 1.36-1.24 (m, 4H), 1.17-1.05 (m, 3H), 0.93 (t, 9H, J=8.0 Hz), 0.84 (s, 3H), 0.82 (d, 3H, J=6.4 Hz), 0.53 (q, 6H, J=8.0 Hz). $^{13}$C NMR (CDCl$_3$, 100 MHz): δ 137.48, 132.72, 129.39, 129.31, 69.20, 55.88, 53.72, 52.94, 42.09, 40.63, 34.48, 34.11, 29.55, 28.12, 26.89, 22.82, 18.28, 17.57, 13.43, 6.91, 4.88. IR (Thin Film) 2946 (s), 2874 (s), 1445 (m), 1490 (m), 1245 (br, s), 1150 (w), 1084 (sh, m), 1021 (br, s), 846 (w) cm$^{-1}$. HRMS: calculated for C$_{27}$H$_{47}$NO$_2$SSiNa$^+$ [M+Na]: 500.2988 Found: 500.2956.

Example 5

General Procedure for the Preparation of C,D-Ring Ketones III, Wherein R$^7$ is not Hydrogen and C22-C23 is a Single Bond Scheme 19

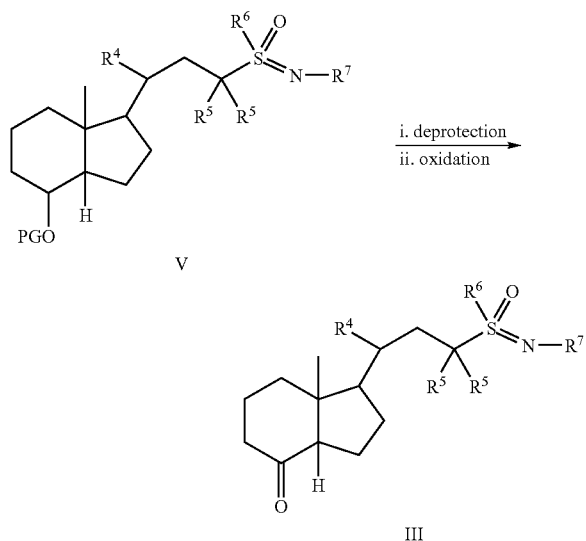

General Deprotection Method

A flame-dried 10 mL recovery flask equipped with a magnetic stir bar, a septum along with an Ar balloon was charged with the appropriate triethylsilyl protected alcohol (35 mg, 0.073 mmol) which was dissolved in 1.4 mL freshly distilled THF to give ca. 0.05 M solution. The flask was cooled down to 0° C. in an ice bath. To this solution 0.21 mL of TBAF (0.22 mmol, 1.0 M solution in THF) was added dropwise over several minutes, resulting in a yellow solution. After the addition was complete, the mixture was gradually warmed up to room temperature and then stirred at this temperature for about 12 hours. TLC showed the complete consumption of starting material. The mixture was concentrated in vacuo and directly purified by column chromatography.

General Oxidation Method

A flame-dried 10-mL recovery flask equipped with a magnetic stir bar, a septum along with an Ar balloon was charged with the appropriate alcohol (25 mg, 0.068 mmol) and dissolved in 1.7 mL freshly distilled CH$_2$Cl$_2$ to give ca. 0.04 M solution. Then, to this solution were added PDC (54 mg, 0.14 mmol) and 34 mg of oven-dried Celite in one portion at room. The resulting mixture was allowed to stir at room temperature for about 12 hours. TLC showed the complete consumption of starting material. The mixture was directly purified by column chromatography.

Example 5(a)

Preparation of CD-Ring Ketone(+)-III(b)

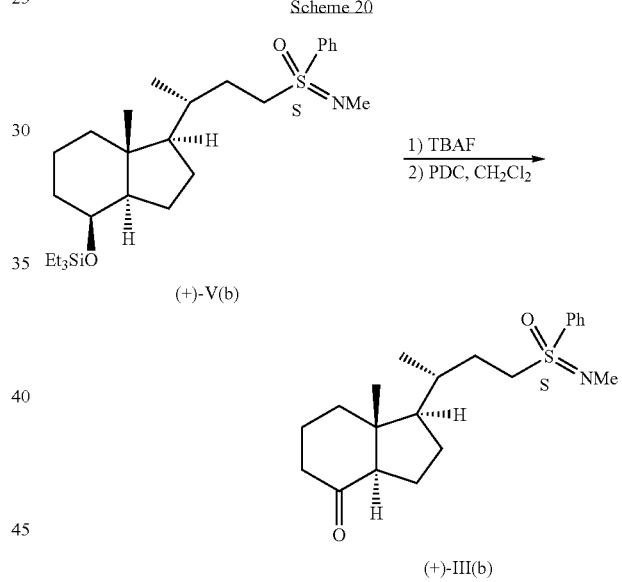

A solution of the triethylsilyl protected alcohol (+)-V(b) (35 mg, 0.073 mmol) in 1.4 mL freshly distilled THF was prepared to give ca. 0.05 M solution. The flask was cooled down to 0° C. in an ice bath. To this solution 0.21 mL of TBAF (0.22 mmol, 1.0 M solution in THF) was added dropwise over several minutes, resulting in a yellow solution. After the addition was complete, the mixture was gradually warmed up to room temperature and then stirred at this temperature for about 12 hours. TLC showed the complete consumption of starting material. The mixture was concentrated in vacuo and directly purified by column chromatography. Flash column chromatography eluted with 100% ethyl acetate afforded 24.3 mg of the corresponding alcohol in 98% yield. Product was recrystallized from acetone by slow evaporation. m. p. 115-116° C. $[\alpha]^{25}_D=+86.76$ (c=2.18, Acetone) $^1$H NMR (Aceton-d$_6$, 400 MHz): δ 7.86-7.83 (m, 2H), 7.70-7.61 (m, 3H), 3.99 (br, 1H), 3.17 (ddd, 1H, J=4.4 Hz, J=4.4 Hz, J=11.6 Hz), 3.04 (ddd, 1H, J=4.8 Hz, 4.8 Hz, J=11.8 Hz), 2.86 (br, 1H), 2.55 (s, 3H), 1.91-1.58 (m, 6H), 1.50-1.24 (m, 6H), 1.19-1.00

(m, 3H), 0.90 (s, 3H), 0.85 (d, 3H, J=6.4 Hz). $^{13}$C NMR (Aceton-d$_6$, 100 MHz): 6139.51, 133.50, 130.19 (2C), 68.71, 56.91, 53.91, 53.71, 42.80, 41.54, 35.07, 34.93, 29.51, 29, 34, 27.78, 23.39, 18.79, 18.40, 14.07. IR (Thin Film) 3284 (br, m), 2930 (s), 2877 (m), 1446 (sh, m), 1402 (w), 1377 (w), 1232 (s), 1147 (s), 1106 (m), 992 (w), 943 (w), 861 (w) cm$^{-1}$. HRMS: calculated for $C_{21}H_{33}NO_2SNa^+$ [M+Na]: 386.2124 Found: 386.2138.

The corresponding alcohol (25 mg, 0.068 mmol) was dissolved in 1.7 mL freshly distilled $CH_2Cl_2$ to give ca. 0.04 M solution. Then, to this solution was added PDC (54 mg, 0.14 mmol) and 34 mg of oven-dried Celite in one portion at room. The resulting mixture was allowed to stir at room temperature for about 12 hours. TLC showed the complete consumption of starting material. The mixture was directly purified by column chromatography. Flash column chromatography eluted with 100% ethyl acetate afforded the ketone (+)-M(b) as a viscous oil in 82% yield. Data for (+)-III(b): $[\alpha]^{25}_D$=+52.61 (c=0.5, CHCl$_3$) $^1$H NMR (CDCl$_3$, 400 MHz): δ 7.86-7.83 (m, 2H), 7.65-7.55 (m, 3H), 3.23 (ddd, 1H, J=4.8 Hz, J=5.2 Hz, J=12.0 Hz), 3.00 (ddd, 1H, J=4.4 Hz, J=4.8 Hz, J=11.6 Hz), 2.67 (s, 3H), 2.41 (dd, 1H, J=7.6 Hz, J=6.0 Hz), 2.29-2.16 (m, 2H), 2.05-1.35 (m, 1H), 1.25-1.16 (m, 1H), 0.89 (d, 3H, J=6.0 Hz), 0.56 (s, 3H). $^{13}$C NMR (CDCl$_3$, 100 MHz): δ 211.54, 137.43, 132.80, 129.35, 129.31, 61.68, 55.86, 53.83, 49.69, 40.78, 38.75, 34.45, 29.46, 28.07, 27.13, 23.86, 18.89, 18.32, 12.36. IR (Thin Film) 2956 (s), 2874 (s), 2801 (w), 1711 (s), 1445 (sh, m), 1380 (w), 1243 (br, s), 1107 (w), 1080 (w), 920 (w), 858 (w) cm$^{-1}$. HRMS: calculated for $C_{21}H_{31}NO_2SNa^+$ [M+Na]: 384.1967 Found: 384.1943.

Example 5(b)

Preparation of CD-Ring Ketone (−)-III(b')

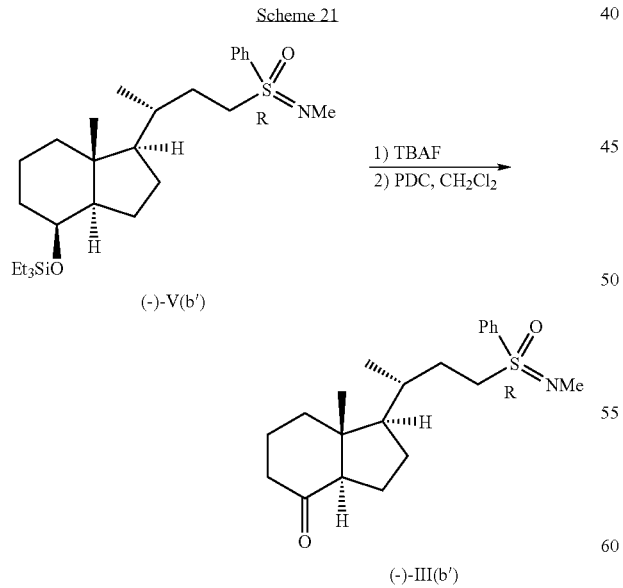

A solution of the triethylsilyl protected alcohol (−)-V(b') (35 mg, 0.073 mmol) in 1.4 mL freshly distilled THF was prepared to give ca. 0.05 M solution. The flask was cooled down to 0° C. in an ice bath. To this solution 0.21 mL of TBAF (0.22 mmol, 1.0 M solution in THF) was added dropwise over several minutes, resulting in a yellow solution. After the addition was complete, the mixture was gradually warmed up to room temperature and then stirred at this temperature for about 12 hours. TLC showed the complete consumption of starting material. The mixture was concentrated in vacuo and directly purified by column chromatography. Flash column chromatography eluted with 100% ethyl acetate afforded 24.8 mg of the corresponding alcohol as a white solid in 93% yield. Product was recrystallized from acetone by slow evaporation. m. p. 122-123° C. $[\alpha]^{25}_D$=−31.93 (c=2.36, Acetone) $^1$H NMR (Aceton-d$_6$, 400 MHz): δ 7.85-7.83 (m, 2H), 7.70-7.61 (m, 3H), 3.99 (br, 1H), 3.20-3.01 (m, 2H), 2.88 (br, 1H), 2.54 (s, 3H), 1.91-1.58 (m, 6H), 1.54-1.46 (m, 1H), 1.42-1.23 (m, 5H), 1.16-1.01 (m, 3H), 0.92 (s, 3H), 0.86 (d, 3H, J=6.4 Hz). $^{13}$C NMR (Aceton-d$_6$, 100 MHz): δ 139.37, 133.51, 130.20 (2C), 68.72, 56.84, 53.71, 42.80, 41.53, 35.03, 34.92, 29.53, 29, 33, 27.70, 23.39, 18.81, 18.39, 14.07. IR (Thin Film) 3280 (br, m), 2930 (s), 2877 (s), 1445 (m), 1238 (br, s), 1148 (m), 1106 (m), 865 (w) cm$^{-1}$. HRMS: calculated for $C_{21}H_{33}NO_2SNa^+$ [M+Na]: 386.2124 Found: 386.2155.

The corresponding alcohol (25 mg, 0.068 mmol) was dissolved in 1.7 mL freshly distilled $CH_2Cl_2$ to give ca. 0.04 M solution. Then, to this solution was added PDC (54 mg, 0.14 mmol) and 34 mg of oven-dried Celite in one portion at room. The resulting mixture was allowed to stir at room temperature for about 12 hours. TLC showed the complete consumption of starting material. The mixture was directly purified by column chromatography. Flash column chromatography eluted with 100% ethyl acetate afforded 23.5 mg of ketone (−)-III(b') in 95% yield. Data for (−)—III(b'): $[\alpha]^{25}_D$=−24.43 (c=0.5, CHCl$_3$) $^1$H NMR (CDCl$_3$, 400 MHz): δ 7.86-7.83 (m, 2H), 7.65-7.55 (m, 3H), 3.19-3.04 (m, 2H), 2.67 (s, 3H), 2.40 (dd, 1H, J=7.6 Hz, J=11.2 Hz), 2.29-2.15 (m, 2H), 2.05-1.80 (m, 4H), 1.75-1.63 (m, 2H), 1.56-1.20 (m, 6H), 0.91 (d, 3H, J=6.8 Hz), 0.59 (s, 3H). $^3$C NMR (CDCl$_3$, 100 MHz): δ 211.53, 137.36, 132.80, 129.35, 129.32, 61.68, 55.80, 53.65, 49.69, 40.78, 38.76, 34.30, 29.48, 28.10, 27.08, 23.85, 18.89, 18.34, 12.38. IR (Thin Film) 2958 (s), 2875 (s), 2802 (w), 1713 (s), 1445 (sh, m), 1380 (m), 1243 (br, s), 1145 (s), 1107 (s), 1083 (s), 920 (w), 858 (w) cm$^1$. HRMS: calculated for $C_{21}H_{31}NO_2SNa^+$ [M+Na]: 384.1967 Found: 384.2000.

Example 6a

24-Phenyl N-Methyl Sulfoximines (Ie) and I(f)

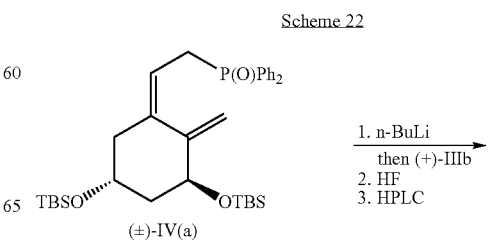

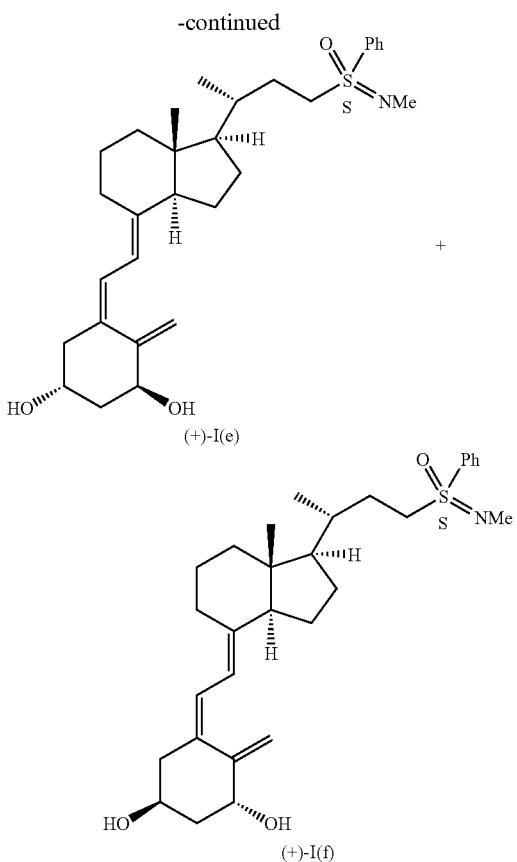

(+)-I(e)

(+)-I(f)

Prior to reaction, the phosphine oxide (±)IV(a) (Posner, G. H. et al. *J. Med. Chem.* 1992, 35, 3280-3287) and CD-ring ketone (+)-IIIb were azeotrophically dried with benzene and left under vacuum for 48 h. The phosphine oxide (±)IV(a) (70 mg, 0.12 mmol) was dissolved in 2.4 mL freshly distilled THF under argon to give ca. 0.05 M solution in a 10 mL flask. The flask was cooled down to −78° C. in an isopropanol/dry ice bath. To this solution was added n-BuLi (78 µL, 0.12 mmol, 1.53 M solution in hexanes) dropwise over several minutes during which time a deep red color developed and persisted. This mixture was allowed to stir at −78° C. for an additional 10 min. Meanwhile, a flame-dried 10 mL recovery flask equipped with a magnetic stir bar and containing the CD-ring ketone (+)-IIIb (22 mg, 0.06 mmol) was dissolved in 1 mL freshly distilled THF under argon and cooled down to −78° C. in an isopropanoury ice bath. The solution of CD-ring ketone(+)-IIIb was gently transferred dropwise into the flask containing the phoshine oxide anion at −78° C. via cannula over several minutes. After the addition was complete, the deep red color persisted and the mixture was allowed to stir at 78° C. for ca. 10 hours during which time it was visually checked. Upon observation of the light yellow color, the reaction was quenched at −78° C. by addition of 5 mL of pH 7 buffer and allowed to come to room temperature. The mixture was then rinsed into a separatory funnel with ethyl acetate and extracted with ethyl acetate (3×25 mL). The combined extracts were washed with water (1×25 mL) and brine solution (1×25 mL), dried over $Na_2SO_4$ and filtered. The filtrate was concentrated in vacuo to give the crude product which was purified by column chromatography eluted with 50% ethyl acetate in hexanes in the presence of 1% triethylamine to afford the coupled product as a waxy solid.

The coupled product (17 mg, 0.023 mmol) was placed into a 5 mL argon purged polypropylene vial equipped with a magnetic stir bar, and dissolved in 1.0 mL anhydrous acetonitrile under argon to give ca. 0.02 M solution. To this well-stirred solution was added 0.1 mL of HF (2.3 mmol, 49% aqueous solution) via syringe at room temperature and the mixture was then allowed to stir at room temperature in the dark for 2 hours. TLC showed the completion of the reaction. This reaction mixture was diluted with ether (25 mL) and saturated solution of $NaHCO_3$ was added until no more carbon dioxide was liberated. The reaction mixture was then rinsed into a separatory funnel with ethyl acetate and was extracted with ethyl acetate (4×25 mL). The combined extracts were washed with water (1×25 mL), and brine solution (1×25 mL), dried over $Na_2SO_4$ and filtered. The filtrate was concentrated in vacuo to give the crude product that was purified by column chromatography.

Flash column chromatography eluted with 99% ethyl acetate in the presence of 1% triethylamine afforded 10.3 mg of a mixture of (+)-I(e) and (+)-I(f) in 89% yield and in a ratio of 2.7:1 respectively. This diastereomeric mixture was then separated by HPLC using a Chiralcel OJ column (Semi-preparative (1×25 cm), flow rate=2.5 mL/min) eluted with 7% ethanol in hexanes to afford 6.62 mg (+)-I(e) and 2.73 mg (+)-I(f) in 57% and 23% yields respectively. The retention time for (+)-I(e) was 52.08 min, and for (+)-I(f) was 43.08 min.

Data for (+)-I(e): $[\alpha]_D$=+57.3 (c=0.44, $CHCl_3$) $^1H$ NMR ($CDCl_3$, 400 MHz): δ 7.86-7.84 (m, 2H), 7.64-7.54 (m, 3H), 6.36 (d, 1H, J=11.2 Hz), 5.98 (d, 1 Hz), 5.32 (dd, 1H, J=1.6 Hz, J=1.6 Hz), 4.99-4.98 (m, 1H), 4.44-4.42 (m, 1H), 4.2-4.22 (m, 1H), 3.22 (ddd, 1H, J=4.8 Hz, J=12.8 Hz, J=13.6 Hz), 3.00 (ddd, 1H, J=4.4 Hz, J=11.6 Hz, J=13.6 Hz), 2.80 (dd, 1H, J=4.4 Hz, J=12.8 Hz), 2.67 (s, 3H), 2.59 (dd, 1H, J=3.2 Hz, J=13.2 Hz) 2.30 (dd, 1H, J=6.8 Hz, J=13.6 Hz), 2.04-1.89 (m, 3H), 1.80-1.38 (m, 1H), 1.28-1.12 (m, 4H), 0.85 (d, 3H, J=6.4 Hz), 0.47 (s, 3H). $^{13}C$ NMR ($CDCl_3$, 100 MHz): δ 147.56, 142.66, 137.52, 133.07, 132.78, 129.37 (br, 2C) 124.84, 117.16, 111.84, 70.80, 66.80, 56.13, 55.69, 53.90, 45.80, 45.23, 42.80, 40.29, 35.04, 29.54, 28.93, 28.17, 27.26, 23.43, 22.11, 18.47, 11.92. IR: 3378 (br, m), 2944 (s), 2874 (m), 1645 (w), 1445 (m), 1380 (w), 1235 (br, s), 1146 (m), 1107 (w), 1067 (sh, m), 957 (w), 895 (w), 753 (s) cm$^{-1}$. HRMS: calculated for $C_{30}H_{44}NO_3S^+$ [M+]: 498.3036. Found: 498.3045.

Data for (+)-I(f): $[\alpha]_D$=+43.3 (c=0.18, $CHCl_3$) $^1H$ NMR ($CDCl_3$, 400 MHz): δ 7.86-7.83 (m, 2H), 7.64-7.54 (m, 3H), 6.37 (d, 1H, J=11.2 Hz), 5.98 (d, 1H, J Hz), 5.31 (dd, 1H, J=1.2 Hz, J=1.6 Hz), 4.99-4.98 (m, 1H), 4.43 (br, 1H), 4.22-4.20 (m, 1H), 3.22 (ddd, 1H, J=5.2 Hz, J=12.4 Hz, J=13.6 Hz), 3.00 (ddd, 1H, J=4.4 Hz, 11.6 Hz, 13.6 Hz), 2.80 (dd, 1H, J=4.0 Hz, J=12.8 Hz), 2.67 (s, 3H), 2.61 (dd, 1H, J=3.2 Hz, J=12.8 Hz), 2.29 (dd, 1H, J=7.6 Hz, J=13.6 Hz), 2.03-1.19 (m, 3H), 1.41 (m, 1H), 1.28-1.13 (m, 4H), 0.85 (d, 3H, J=6.8 Hz), 0.47 (s, 3H). $^{13}C$ NMR ($CDCl_3$, 100 MHz): δ 147.3, 142.7, 137.5, 132.9, 132.8, 129.4, 128.9, 124.83, 117.2, 11.5, 71.3, 66.8, 56.1, 55.7, 53.9, 45.8, 45.4, 42.8, 40.29, 30.1, 29.6, 28.9, 28.2, 27.3, 23.4, 22.1, 18.5, 12.0. IR: 3374 (br, m), 2943 (s), 2873 (m), 1646 (w), 1445 (m), 1379 (w), 1235 (br, s), 1145 (s), 1057 (br, s), 957 (m), 861 (m), 752 (s) cm$^{-1}$. HRMS: calculated for $C_{30}H_{44}NO_3S$+[M+]: 498.3036 Found: 498.3049.

Example 6b

24-Phenyl N-Methyl Sulfoximines I(g) and I(h)

In a like manner, the compounds (+)-I(g) and (−)-I(h) can be prepared as shown in Scheme 23:

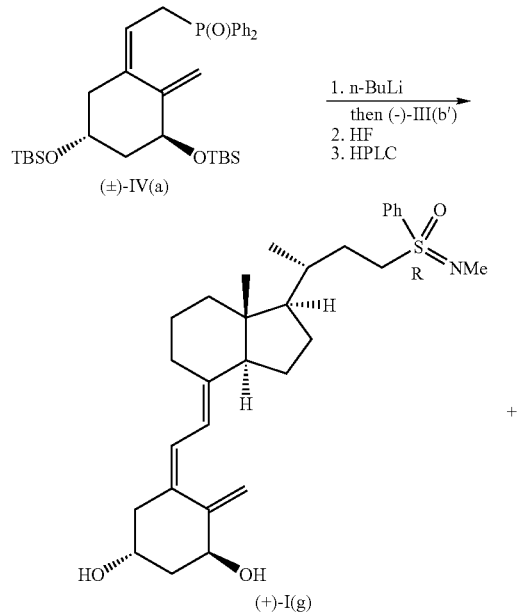

wherein CD-ring ketone (−)-III(b') instead of CD-ring ketone (+)-III(b) is coupled with phospine oxide (±)IV(a) as disclosed in example 6a above. After the coupling reaction and the subsequent deprotection step, flash column chromatography eluted with 99% ethyl acetate in the presence of 1% triethylamine afforded 9.5 mg of a mixture of diastereomers (+)-I(g) and (−)-I(h) in 82% yield and in a ratio of 3:1 respectively. The diastereomeric mixture was then separated by HPLC using a Chiralcel OJ column (Semipreparative (1×25 cm), flow rate=2.5 mL/min) eluted with 7% ethanol in hexanes to afford 3.39 mg (+)-I(g) and 1.12 mg (−)-I(h) in 29% and 10% yields respectively. The retention time for (+)-I(g) was 45.19 min. and for (−)-I(h) was 39.84 min.

Data for (+)-I(g): $[\alpha]_D$=+7.1 (c=0.2, CHCl$_3$) $^1$H NMR (CDCl$_3$, 400 MHz): δ 7.86-7.83 (m, 2H), 7.64-7.54 (m, 3H), 6.35 (d, 1H, J=11.2 Hz), 5.98 (d, 1H, J=11.2 Hz), 5.31 (dd, 1H, J=1.2 Hz, J=2.0 Hz), 4.98 (dd, 1H, J=1.2 Hz, J=2.0 Hz), 4.43 (m, 1H), 4.22 (m, 1H), 3.19-3.04 (m, 2H), 2.80 (dd, 1H, J=4.4 Hz, J=12.8 Hz), 2.67 (s, 3H), 2.59 (dd, 1H, J=3.2 Hz, J=13.6 Hz) 2.30 (dd, 1H, J=6.8 Hz, J=13.6 Hz) 2.05-1.84 (m, 4H), 1.71-1.13 (m, 14H), 0.86 (d, 3H, J=6.8 Hz), 0.49 (s, 3H). $^{13}$C NMR (CDCl$_3$, 100 MHz): d 147.58, 142.64, 137.49, 133.08, 132.76, 129.37 (br, 2C), 124.84, 117.18, 111.81, 70.80, 66.82, 56.15, 55.70, 53.77, 45.82, 45.23, 42.83, 40.32, 34.94, 29.55, 28.94, 28.17, 27.22, 23.44, 22.12, 18.48, 11.93. IR: 3350 (m, br), 2924 (s), 2873 (m), 1445 (m), 1378 (w), 1235 (br, s), 1147 (m), 1107 (w), 1057 (m), 861 (w), 753 (s) cm$^{-1}$. HRMS: calculated for C$_{30}$H$_{44}$NO$_3$S$^+$ [M+]: 498.3036. Found: 498.3049.

Data for (−)-I(h): $[\alpha]_D$=−8.5 (c=0.08, CHCl$_3$) $^1$H NMR (CDCl$_3$, 400 MHz): δ 7.86-7.84 (m, 2H), 7.64-7.52 (m, 3H), 6.36 (d, 1H, J=11.6 Hz), 5.97 (d, 1H, J=11.6 Hz), 5.31 (br, 1H), 4.98 (m, 1H), 4.43 (br, 1H), 4.22 (m, 1H), 3.19-3.04 (m, 2H), 2.80 (dd, 1H, J=4.4 Hz, J=12.4 Hz), 2.67 (s, 3H), 2.61-2.58 (m, 1H), 2.29 (dd, 1H, J=6.4 Hz, J=12.8 Hz) 2.01-1.90 (m, 5H), 1.69-1.17 (m, 13H), 0.86 (d, 3H, J=6.4 Hz), 0.49 (s, 3H). $^{13}$C NMR (CDCl$_3$, 100 MHz): d 147.3, 142.7, 137.4, 133.1, 132.9, 129.4, 129.0, 124.9, 117.2, 112.5, 71.3, 66.8, 56.1, 55.7, 53.78, 45.8, 45.4, 42.8, 40.3, 34.9, 29.6, 28.9, 28.2, 27.2, 23.4, 22.12, 18.5, 11.9. IR: 3383 (br, m) 2926 (s), 2873 (s), 1445 (m), 1235 (br, s), 1145 (s), 1056 (br, m), 957 (w), 860 (br, w), 753 (s) cm$^{-1}$. HRMS: calculated for C$_{30}$H$_{44}$NO$_3$S$^+$ [M+]: 498.3036 Found: 498.3061.

Example 7a

24-Phenyl Sulfoximine 19-Nor-Vitamin-D$_3$ I(i)

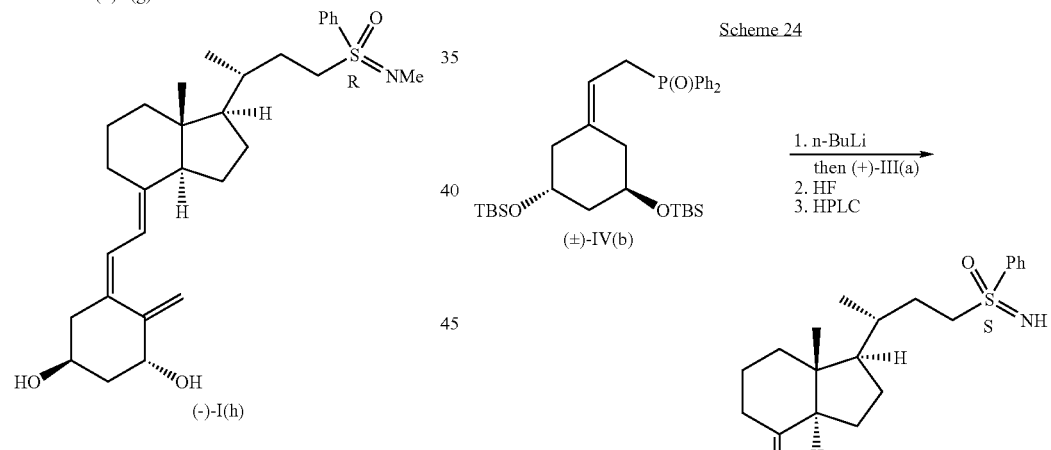

Prior to reaction, the phosphine oxide (+)-IV(b) (Posner, G. H. et al. *J. Med. Chem.* 1992, 35, 3280-3287) and CD-ring ketone (+)-III(a) were azeotrophically dried with benzene and left under vacuum for 48 h. Under argon, the phosphine oxide (+)-IV(b) (76 mg, 0.13 mmol) was dissolved in 0.8 mL freshly distilled THF to give ca. 0.1 M solution in a flame-dried 10 mL flask, and the flask was cooled down to −78° C. in an isopropanol/dry ice bath. To this solution was added n-BuLi (83 μL, 0.13 mmol, 1.6 M solution in hexanes) dropwise over several minutes during which time a deep red color developed and persisted. This mixture was allowed to stir at −78° C. for an additional 10 min. Meanwhile, a flame-dried 10-mL recovery flask equipped with a magnetic stir bar, a septum along with an Ar balloon was charged with CD-ring ketone (+)-III(a) (14 mg, 0.040 mmol) dissolved in 1 mL freshly distilled THF and cooled down to −78° C. in an isopropanol/dry ice bath. The solution of CD-ring ketone was gently transferred dropwise into the flask containing the phoshine oxide anion at −78° C. via cannula over several minutes. After the addition was complete, the deep red color persisted and the mixture was allowed to stir at 78° C. for ca. 15 hours during which time it was visually checked. Upon observation of the light yellow color, the reaction was quenched at −78° C. by addition of 5 mL of pH 7 buffer and allowed to come to room temperature. The mixture was then rinsed into a separatory funnel with ethyl acetate and extracted with ethyl acetate (3×25 mL). The combined extracts were washed with water (1×25 mL) and brine solution (1×25 mL), dried over $Na_2SO_4$ and filtered. The filtrate was concentrated in vacuo to give the crude product which was purified by column chromatography eluted with 50% ethyl acetate in hexanes in the presence of 1% triethylamine to afford the coupled product.

The coupled product (15 mg, 0.021 mmol) in a 5 mL argon purged polypropylene vial equipped with a magnetic stir bar was dissolved in 1.0 mL anhydrous acetonitrile to give ca. 0.02 M solution. To this well-stirred solution was added 87 mL of HF (2.1 mmol, 49% aqueous solution) via syringe at room temperature and the mixture was then allowed to stir at room temperature in the dark for 2 hours. TLC showed the completion of the reaction. The reaction mixture was diluted with ether (25 mL) and saturated solution of $NaHCO_3$ was added until no more carbon dioxide was liberated. The reaction mixture was then rinsed into a separatory funnel with ethyl acetate and was extracted with ethyl acetate (5×25 mL). The combined extracts were washed with water (1×25 mL), and brine solution (1×25 mL), dried over $Na_2SO_4$ and filtered. The filtrate was concentrated in vacuo to give the crude product that was purified by column chromatography.

Flash column chromatography eluted with 99% ethyl acetate in the presence of 1% triethylamine afforded 3.7 mg of (+)-I(i) in 70% yield. This analog was then further purified by HPLC using a Chiralcel OJ column (Semipreparative (1×25 cm), flow rate=2.5 mL/min) eluted with 15% ethanol in hexanes to afford 2.3 mg of (+)-I(i) in 43% yield. The retention time for (+)-I(i) was 35.22 min.

Data for (+)-I(i): $[α]_D$=+82.3 (c=0.16, MeOH) $^1H$ NMR ($d_3$-MeOD, 400 MHz): δ 7.98-7.96 (m, 2H), 7.73-7.61 (m, 3H), 6.20 (d, 1H, J=11.2 Hz), 5.86 (d, 1 Hz), 4.05-3.96 (m, 2H), 3.26 (dd, 1H, J=4.0, 11.6 Hz), 3.19-3.13 (m, 1H), 2.81 (dd, 1H, J=3.6 Hz, J=11.6 Hz), 2.58 (dd, 1H, J=4.0 Hz, J=13.6 Hz), 2.40 (dd, 1H, J=3.6 Hz, J=14.0 Hz), 2.23-2.13 (m, 2H), 2.03-1.93 (m, 2H), 1.84-1.46 (m, 12H), 1.33-1.17 (m, 5H), 0.89 (d, 3H, J=6.0 Hz), 0.51 (s, 3H). $^{13}C$ NMR ($d_3$-MeOD, 100 MHz): d 142.17, 141.91, 134.66, 134.20, 130.55, 129.81, 123.51, 117.41, 68.11, 67.84, 57.46, 57.29, 55.81, 46.89, 45.55, 42.81, 41.83, 37.76, 36.43, 30.52, 29.88, 28.46, 24.57, 23.31, 19.10, 12.49. IR: 3330 (m, br), 2942 (s), 2872 (s), 1443 (m), 1213 (br, s), 1096 (m), 1049 (m), 978 (s), 755 (s) $cm^{-1}$. HRMS: calculated for $C_{28}H_{41}NO_3SNa^+$ [M+Na]: 494.2699. Found: 494.2679.

Example 7b

24 Phenyl Sulfoximine 19-Nor-Vitamin-D3 I(i)

In a like manner, compound I(j) can be prepared as shown in Scheme 25:

Scheme 25

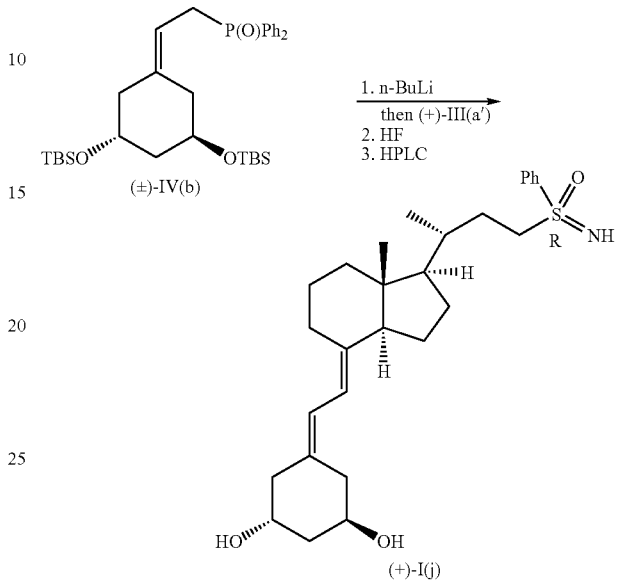

(+)-I(j)

wherein CD-ring ketone (+)-III(a') instead of CD-ring ketone (+)-III(a) is coupled with phospine oxide (J)IV(b) as disclosed in example 7a above. After the coupling reaction and the subsequent deprotection step, flash column chromatography eluted with 99% ethyl acetate in the presence of 1% triethylamine afforded 9.1 mg of (+)-I(j) in 91% yield. This analog was then further purified by HPLC using Chiralcel OJ column (Semipreparative (1×25 cm), flow rate=2.5 mL/min) eluted with 15% ethanol in hexanes to afford 7 mg of (+)-Id) in 70% yield. The retention time for (+)-I(j) was 30.25 min.

Data for (+)-I(j): $[α]_D$=+101.6 (c=0.46, MeOH) $^1H$ NMR ($d_3$-MeOD, 400 MHz): δ 7.98-7.96 (m, 2H), 7.73-7.62 (m, 3H), 6.20 (d, 1H, J=11.2 Hz), 5.86 (d, 1H, J=11.2 Hz), 4.04-3.96 (m, 2H), 3.26 (dd, 1H, J=4.8, 12.0 Hz), 3.15 (ddd, 1H, J=4.8, 11.6, 14.0 Hz) 2.81 (dd, 1H, J=3.6 Hz, J=12.4 Hz), 2.58 (dd, 1H, J=3.6 Hz, J=13.6 Hz), 2.40 (dd, 1H, J=2.8 Hz, J=13.6 Hz), 2.23-2.13 (m, 2H), 2.02-1.94 (m, 2H), 1.87-1.45 (m, 12H), 1.39-1.14 (m, 5H), 0.90 (d, 3H, J=6.8 Hz), 0.52 (s, 3H). $^{13}C$ NMR ($d_3$-MeOD, 100 MHz): d 142.11, 141.90, 134.66, 134.19, 130.55, 129.81, 123.50, 117.41, 68.11, 67.83, 57.45, 57.24, 55.70, 46.88, 45.55, 42.80, 41.81, 37.76, 36.41, 30.47, 29.88, 28.44, 24.57, 23.31, 19.12, 12.48. IR: 3330 (m, br), 2942 (s), 2872 (s), 1437 (m), 1213 (br, s), 1096 (m), 1049 (m), 978 (m), 749 (s) $cm^{-1}$. HRMS: calculated for $C_{28}H_{41}NO_3SNa^+$ [M+Na]: 494.2699. Found: 494.2707.

Example 8a

24-Phenyl N-Methyl Sulfoximine 19-Nor-Vitamin-$D_3$ I(k)

Scheme 26

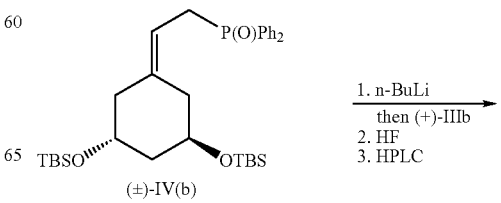

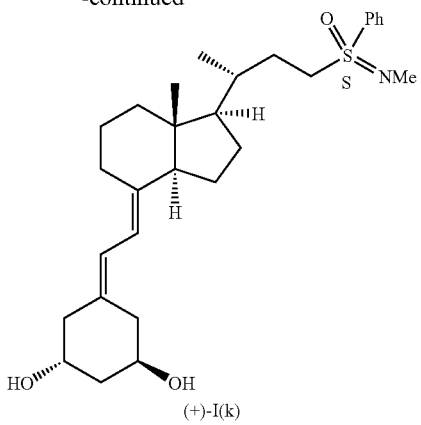

(+)-I(k)

Prior to reaction, the phosphine oxide (±)IV(b) (Posner, G. H. et al. *J. Med. Chem.* 1992, 35, 3280-3287) and CD-ring ketone (+)-III(b) were azeotrophically dried with benzene and left under vacuum for 48 h. The phosphine oxide (±)IV(b) (53 mg, 0.092 mmol) was dissolved in 0.9 mL freshly distilled THF under argon to give ca. 0.01 M solution in a 10 mL flask. The flask was cooled down to −78° C. in an isopropanol/dry ice bath. To this solution was added n-BuLi (55 µL, 0.093 mmol, 1.7 M solution in hexanes) dropwise over several minutes during which time a deep red color developed and persisted. This mixture was allowed to stir at −78° C. for an additional 10 min. Meanwhile, a flame-dried 10 mL recovery flask equipped with a magnetic stir bar and containing the CD-ring ketone (+)-III(b) (16 mg, 0.044 mmol) was dissolved in 1 mL freshly distilled THF under argon and cooled down to −78° C. in an isopropanol/dry ice bath. The solution of CD-ring ketone (+)-III(b) was gently transferred dropwise into the flask containing the phoshine oxide anion at −78° C. via cannula over several minutes. After the addition was complete, the deep red color persisted and the mixture was allowed to stir at 78° C. for ca. 10 hours during which time it was visually checked. Upon observation of the light yellow color, the reaction was quenched at −78° C. by addition of 5 mL of pH 7 buffer and allowed to come to room temperature. The mixture was then rinsed into a separatory funnel with ethyl acetate and extracted with ethyl acetate (3×25 mL). The combined extracts were washed with water (1×25 mL) and brine solution (1×25 mL), dried over $Na_2SO_4$ and filtered. The filtrate was concentrated in vacuo to give the crude product which was purified by column chromatography eluted with 50% ethyl acetate in hexanes in the presence of 1% triethylamine to afford the coupled product as a waxy solid.

The coupled product (21 mg, 0.029 mmol) was placed into a 5 mL argon purged polypropylene vial equipped with a magnetic stir bar, and dissolved in 1.5 mL anhydrous acetonitrile under argon to give ca. 0.02 M solution. To this well-stirred solution was added 0.12 mL of HF (2.9 mmol, 49% aqueous solution) via syringe at room temperature and the mixture was then allowed to stir at room temperature in the dark for 1.5 hours. TLC showed the completion of the reaction. This reaction mixture was diluted with ether (25 mL) and saturated solution of $NaHCO_3$ was added until no more carbon dioxide was liberated. The reaction mixture was then rinsed into a separatory funnel with ethyl acetate and was extracted with ethyl acetate (4×25 mL). The combined extracts were washed with water (1×25 mL), and brine solution (1×25 mL), dried over $Na_2SO_4$ and filtered. The filtrate was concentrated in vacuo to give the crude product that was purified by column chromatography.

Flash column chromatography eluted with 99% ethyl acetate in the presence of 1% triethylamine afforded 10.7 mg of (+)-I(k) in 72% yield. This analog was then further purified by HPLC using a Chiralcel OJ column (Semipreparative (1×25 cm), flow rate=2.5 mL/min) eluted with 10% ethanol in hexanes to afford 3.2 mg (+)-I(k) 30% yield. The retention time for (+)-I(k) was 27.26 min. Data for (+)-I(k): $[\alpha]_D$=+ 92.4 (c=0.13, MeOH) $^1$H NMR ($d_3$-MeOD, 400 MHz): δ 7.87-7.85 (m, 2H), 7.74-7.64 (m, 3H), 6.20 (d, 1H, J=10.8 Hz), 5.86 (d, 1H, J=11.2 Hz), 4.06-3.95 (m, 2H), 3.27 (ddd, 1H, J=5.2, 12.0, 18.4 Hz), 3.18 (ddd, 1H, J=4.4, 10.0, 18.4 Hz) 2.81 (dd, 1H, J=3.6 Hz, J=12.0 Hz), 2.60 (s, 3H), 2.58 (dd, 1H, J=4.0 Hz, J=13.2 Hz), 2.40 (dd, 1H, J=3.2 Hz, J=13.2 Hz) 2.22-2.13 (m, 2H), 2.03-1.94 (m, 2H), 1.87-1.42 (m, 13H), 1.34-1.16 (m, 5H), 0.88 (d, 3H, J=6.4 Hz), 0.49 (s, 3H). $^{13}$C NMR ($d_3$-MeOD, 100 MHz): d 141.9, 137.8, 134.8, 134.2, 130.9, 130.7, 123.5, 117.4, 68.1, 67.8, 57.4, 57.3, 54.2, 46.9, 45.5, 42.8, 41.8, 37.7, 36.5, 29.8, 29.7, 29.6, 28.5, 24.6, 23.3, 19.1, 12.5. IR: 3377 (m, br), 2931 (s), 2872 (m), 1437 (m), 1231 (br, s), 1143 (m), 1049 (m), 855 (w), 749 (s) cm$^{-1}$. HRMS: calculated for $C_{29}H_{13}NO_3SNa^+$ [M+Na]: 508.2855. Found: 508.2859.

Example 8b

24-Phenyl N-Methyl Sulfoximine 19-Nor-Vitamin-$D_3$ I(l)

In a like manner, the compound (+)-I(l) can be prepared as shown in Scheme 27:

Scheme 27

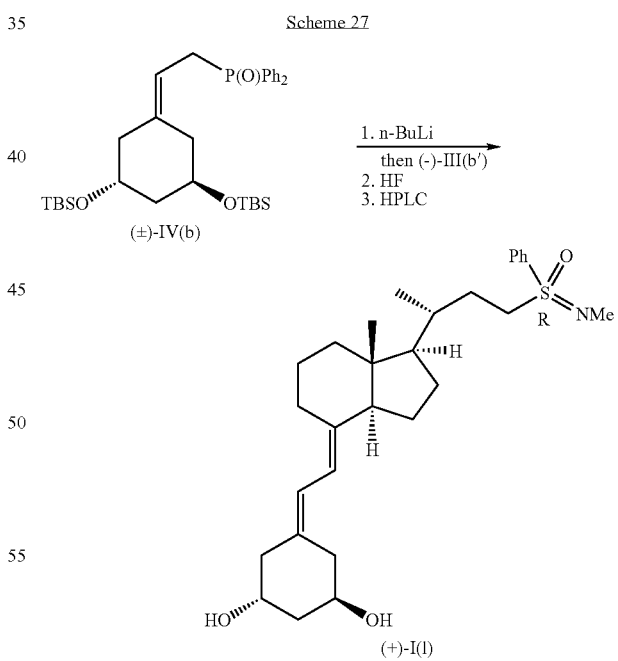

wherein CD-ring ketone (−)-III(b') instead of CD-ring ketone (+)-III(b) is coupled with phospine oxide (±)IV(b) as disclosed in example 8a above. After the coupling reaction and the subsequent deprotection step, flash column chromatography eluted with 99% ethyl acetate in the presence of 1% triethylamine afforded 11.3 mg (+)-I(l) in 79% yield. This analog was then further purified by HPLC using a Chiralcel OJ column (Semipreparative (1×25 cm), flow rate=2.5 mL/min) eluted with 10% ethanol in hexanes to afford 2.9 mg (+)-I(l) 26% yield. The retention time for (+)-I(l) was 25.88 min.

Data for (+)-I(l): $[\alpha]_D$=+71.6 (c=0.13, MeOH) $^1$H NMR ($d_3$-MeOD, 400 MHz): δ 7.87-7.85 (m, 2H), 7.74-7.65 (m, 3H), 6.20 (d, 1H, J=10.8 Hz), 5.86 (d, J=11.2 Hz), 4.05-3.95 (m, 2H), 3.27 (ddd, 1H, J=1.6, 2.8, 12 Hz), 3.17 (ddd, 1H, J=5.6, 12.0, 14.0 Hz) 2.81 (dd, 1H, J=2.8 Hz, J=11.2 Hz), 2.60 (s, 3H), 2.58 (dd, 1H, J=4.0 Hz, J=14.0 Hz), 2.40 (dd, 1H, J=3.2 Hz, J=13.2 Hz) 2.23-2.13 (m, 2H), 2.02-1.94 (m, 2H), 1.84-1.44 (m, 11H), 1.33-1.17 (m, 5H), 0.90 (d, 3H, J=6.4 Hz), 0.53 (s, NMR ($d_3$-MeOD, 100 MHz): d 141.9, 137.7, 134.8, 134.2, 130.9, 130.7, 123.5, 117.4, 68.1, 67.8, 57.4, 57.2, 53.9, 46.9, 45.5, 42.8, 41.8, 37.7, 36.4, 29.9, 29.7, 29.6, 28.4, 24.6, 23.3, 19.1, 12.5. IR: 3389 (m, br), 2942 (s), 2872 (m), 1443 (m), 1231 (br, s), 1143 (m), 1078 (m), 1043 (m), 855 (w), 749 (s) cm$^{-1}$. HRMS: calculated for $C_{29}H_{43}NO_3SNa^+$ [M+Na]: 508.2855. Found: 508.2850.

Example 9

24-Phenyl Sulfoximine 1-Nor Vitamin-$D_3$ I(m)

Scheme 28

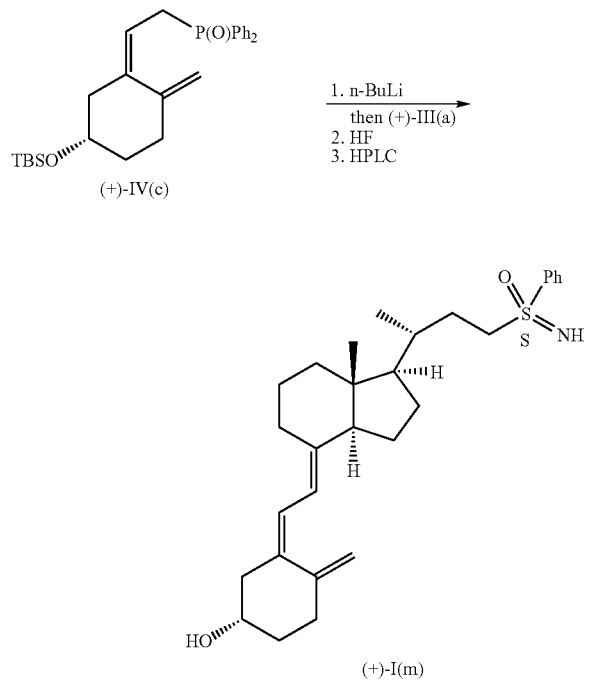

Prior to reaction, the phosphine oxide (+)-IV(c) (Kutner, A. et al. *Bioorg. Chem.* 1995, 23, 22-32) and CD-ring ketone (+)-III(a) were azeotrophically dried with benzene and left under vacuum for 48 h. Under argon, the phosphine oxide (+)-IV(c) (76 mg, 0.13 mmol) was dissolved in 0.8 mL freshly distilled THF to give ca. 0.1 M solution in a flame-dried 10 mL flask, and the flask was cooled down to −78° C. in an isopropanol/dry ice bath. To this solution was added n-BuLi (83 μL, 0.13 mmol, 1.6 M solution in hexanes) dropwise over several minutes during which time a deep red color developed and persisted. This mixture was allowed to stir at −78° C. for an additional 10 min. Meanwhile, a flame-dried 10-mL recovery flask equipped with a magnetic stir bar, a septum along with an Ar balloon was charged with CD-ring ketone (+)-III(a) (14 mg, 0.040 mmol) dissolved in 1 mL freshly distilled THF and cooled down to −78° C. in an isopropanol/dry ice bath. The solution of CD-ring ketone was gently transferred dropwise into the flask containing the phoshine oxide anion at −78° C. via cannula over several minutes. After the addition was complete, the deep red color persisted and the mixture was allowed to stir at 78° C. for ca. 15 hours during which time it was visually checked. Upon observation of the light yellow color, the reaction was quenched at −78° C. by addition of 5 mL of pH 7 buffer and allowed to come to room temperature. The mixture was then rinsed into a separatory funnel with ethyl acetate and extracted with ethyl acetate (3×25 mL). The combined extracts were washed with water (1×25 mL) and brine solution (1×25 mL), dried over $Na_2SO_4$ and filtered. The filtrate was concentrated in vacuo to give the crude product which was purified by column chromatography eluted with 50% ethyl acetate in hexanes in the presence of 1% triethylamine to afford the coupled product.

The coupled product (15 mg, 0.021 mmol) in a 5 mL argon purged polypropylene vial equipped with a magnetic stir bar was dissolved in 1.0 mL anhydrous acetonitrile to give ca. 0.02 M solution. To this well-stirred solution was added 87 mL of HF (2.1 mmol, 49% aqueous solution) via syringe at room temperature and the mixture was then allowed to stir at room temperature in the dark for 2 hours. TLC showed the completion of the reaction. The reaction mixture was diluted with ether (25 mL) and saturated solution of $NaHCO_3$ was added until no more carbon dioxide was liberated. The reaction mixture was then rinsed into a separatory funnel with ethyl acetate and was extracted with ethyl acetate (5×25 mL). The combined extracts were washed with water (1×25 mL), and brine solution (1×25 mL), dried over $Na_2SO_4$ and filtered. The filtrate was concentrated in vacuo to give the crude product that was purified by column chromatography.

Flash column chromatography eluted with 99% ethyl acetate in the presence of 1% triethylamine afforded 10.6 mg of (+)-I(m) in 88% yield. This analog was then further purified by HPLC using a Chiralcel OJ column (Semipreparative (1×25 cm), flow rate=2.5 mL/min) eluted with 10% ethanol in hexanes to afford 3.0 mg of (+)-I(m) in 28% yield. The retention time for (+)-I(m) was 31.47 min.

Data for (+)-I(m): $[\alpha]_D$=+36.6 (c=0.53, CHCl$_3$) $^1$H NMR (CDCl$_3$, 400 MHz): δ 7.98-7.96 (m, 2H), 7.64-7.53 (m, 3H), 6.21 (d, 1H, J=11.6 Hz), 6.00 (d, 1H, Hz), 5.05-5.04 (m, 1H), 4.80 (d, 1H, J=2.4 Hz), 3.96-3.91 (m, 1H), 3.20 (ddd, 1H, J=4.4, 12.4, 13.6 Hz), 3.04 (ddd, 1H, J=4.4, 11.2, 13.6 Hz) 2.80 (dd, 1H, J=4.4 Hz, J=12.4 Hz), 2.56 (dd, 1H, J=4.0 Hz, J=13.2 Hz), 2.43-2.36 (m, 1H), 2.33 (dd, 1H, J=7.6 Hz, J=13.2 Hz) 2.20-2.13 (m, 1H), 1.96-190 (m, 4H), 1.82-1.42 (m, 10H) 1.16 (m, 4H), 0.87 (d, 3H, J=6.4 Hz), 0.49 (s, 3H). $^{13}$C NMR (CDCl$_3$, 100 MHz) 145.0, 142.0, 141.6, 135.3, 132.9, 129.1, 128.3, 122.2, 117.7, 112.4, 69.2, 56.1, 55.7, 54.8, 45.9, 45.7, 40.3, 35.2, 35.0, 31.9, 28.8, 28.7, 27.3, 23.4, 22.1, 18.5, 11.9. IR: 3295 (m, br), 2931 (s), 2860 (m), 1443 (m), 1213 (br, s), 1096 (m), 1061 (w), 984 (m), 749 (s) cm$^{-1}$.

HRMS: calculated for $C_{29}H_{41}NO_2SNa^+$ [M+Na]: 490.2750. Found: 490.2723. UV (MeOH) $\lambda_{max}$ 265 nm ($\epsilon$ 15,648).

Example 10

General Procedure for the Preparation of Compounds of the Formula V, Wherein $R^7$ is Hydrogen and Both $R^5$ Together Form a Cyclopropyl Ring

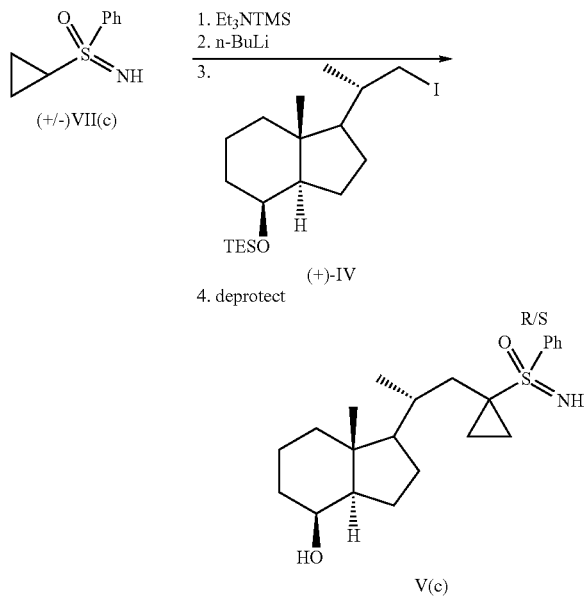

A flame-dried 10-mL recovery flask equipped with a magnetic stir bar, a reflux condenser a septum along with an Ar balloon was charged with (±)-S-cyclopropyl-S-phenyl sulfoximine VII(c) (100 mg, 0.55 mmol) and dissolved in 1.1 mL anhydrous acetonitrile to give 0.5 M solution. Then the flask was placed into an oil bath at 60° C. To this solution was added $Et_2NTMS$ (125 µL, 0.66 mmol) via a syringe dropwise over several minutes. After the addition was complete, the mixture was allowed to stir at 60° C. for ca. 30 minutes. When TLC showed total consumption of the starting material, the flask cooled down to room temperature. The mixture was concentrated in vacuo to give the N-trimethylsilyl sulfoximine product, essentially pure as determined by $^1H$ NMR. This was used without further purification.

A flame-dried 10-mL recovery flask equipped with a magnetic stir bar, a septum along with an Ar balloon was charged with the appropriate N-trimethylsilyl sulfoximine (0.163 mg, 0.55 mmol) dissolved in 2.8 mL freshly distilled THF and 0.28 mL HMPA. Then the flask was cooled down to −78° C. in an isopropanol/dry ice bath. To this solution was added 0.34 mL of n-BuLi (0.55 mmol, 1.6 M solution in hexanes) dropwise over several minutes during which time a pale yellow color developed. This mixture was allowed to stir at −78° C. for an additional 30 min, then warmed up to 0° C. for 10 min. The flask was recooled to −78° C. Meanwhile, a flame-dried 10-mL pear shaped flask equipped with a septum along with an Ar balloon was charged with iodide (+)-VI (80 mg, 0.18 mmol) dissolved in 0.5 mL freshly distilled THF and cooled down to −78° C. in an isopropanol/dry ice bath. The solution of iodide (+)-VI was transferred into the flask containing the lithiated sulfoximine at −78° C. via cannula over several minutes. After the addition was complete, the mixture was gradually warmed up to room temperature and stirred at this temperature for about 10 hours. TLC showed the complete consumption of starting material. The reaction was quenched by addition of 2 mL 3N aqueous HCl and allowed to stir for 30 minutes. The mixture was diluted with diethyl ether and basified by using 1N aqueous NaOH until pH becomes about 9, then rinsed into a separatory funnel with diethyl ether. The mixture was extracted with diethyl ether (3×25 mL). The combined extracts were washed with water (1×25 mL), and brine solution (1×25 mL), dried over $Na_2SO_4$ and filtered. The filtrate was concentrated in vacuo to give the crude product TMS-protected-V(c) that was purified by flash column chromatography.

Example 11

General Procedure for the Preparation of C,D-Ring Ketones III, wherein $R^7$ is Hydrogen and and Both $R^5$ Together Form a Cyclopropyl Ring General Deprotection Method A flame-dried 10 mL recovery flask equipped with a magnetic stir bar, a septum along with an Ar balloon was charged with the appropriate triethylsilyl protected alcohol V which was dissolved in 1.8 mL freshly distilled THF to give ca. 0.04 M solution. The flask was cooled down to 0° C. in an ice bath. To this solution 0.75 mL of TBAF (49% solution) was added dropwise over several minutes, resulting in a yellow solution. After the addition was complete, the mixture was gradually warmed up to room temperature and then stirred at this temperature for about 4 hours. TLC showed the complete consumption of starting material. The mixture was concentrated in vacuo and directly purified by column chromatography.

General Oxidation Method

A flame-dried 10-mL recovery flask equipped with a magnetic stir bar, a septum along with an Ar balloon was charged with the appropriate alcohol (50 mg, 0.133 mmol) and dissolved in 3.3 mL freshly distilled $CH_2Cl_2$ to give ca. 0.04 M solution. Then, to this solution were added PDC (105 mg, 0.279 mmol) and 66 mg of oven-dried Celite in one portion at room temperature. The resulting mixture was allowed to stir at room temperature for about 12 hours. TLC showed the complete consumption of starting material. The mixture was directly purified by column chromatography.

Example 11(a)

Preparation of CD-Ring Ketone III(c)

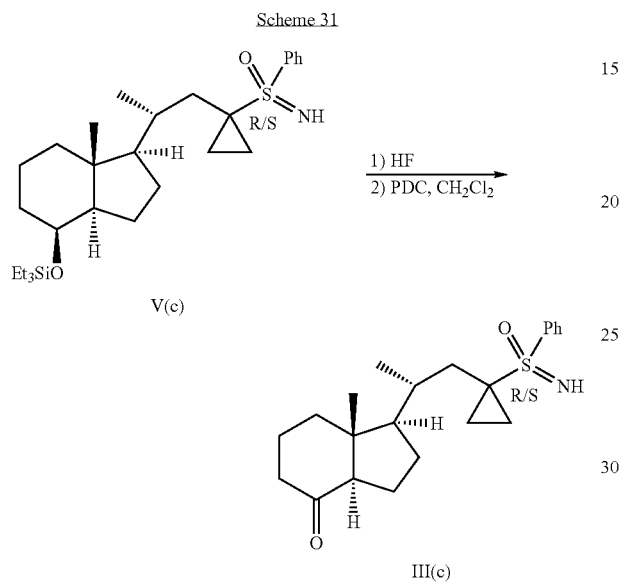

A solution of the triethylsilyl protected alcohol (+)-V(c) in 1.8 mL freshly distilled THF was prepared to give ca. 0.04 M solution. The flask was cooled down to 0° C. in an ice bath. To this solution 0.75 mL of HF (49% aqueous solution) was added dropwise over several minutes, resulting in a yellow solution. After the addition was complete, the mixture was gradually warmed up to room temperature and then stirred at this temperature for about 4 hours. TLC showed the complete consumption of starting material. The mixture was concentrated in vacuo and directly purified by column chromatography. Flash column chromatography eluted with 50% ethyl acetate afforded 50.0 mg of the corresponding alcohol in 73% yield. Product data: $^1$H NMR (CDCl$_3$, 400 MHz): δ 7.97-7.95 (m, 4H), 7.63-7.58 (m, 2H), 7.55-7.50 (m, 4H (br, 2H)), 2.14 (t, 4H, J=11.2 Hz), 1.90 (d, 2H, J=13.2 Hz), 1.78-1.20 (m, 22H), 1.08-0.88 (m, 12H), 0.86 (s, 3H), 0.83 (s, 3H), 0.78-0.70 (m, 2H), 0.71 (d, 3H, J=6.4 Hz), 0.68 (d, 3H, J=6.4 Hz). $^{13}$C NMR (CDCl$_3$, 100 MHz): δ 141.2, 140.50, 132.77, 132.70, 128.97, 128.88, 128.74, 69.05, 57.06, 56.97, 52.40, 41.93, 40.26, 40.20, 37.56, 37.13, 33.46, 33.26, 27.18, 27.13, 22.38, 18.78, 17.28, 13.48, 12.41, 12.27, 12.20, 11.67. IR (Thin Film) 3448 (br, w), 3330 (br, m), 3271 (m), 2931 (s), 2860 (s), 1443 (m), 1219 (br, s), 1067 (sh, m), 984 (s), 967 (m), 755 (s) cm$^{-1}$. HRMS: calculated for C$_{22}$H$_{33}$NO$_2$SNa$^+$ [M+Na]: 398.2124 Found: 398.2121.

The corresponding alcohol (50 mg, 0.133 mmol) was dissolved in 3.3 mL freshly distilled CH$_2$Cl$_2$ to give ca. 0.04 M solution. Then, to this solution was added PDC (105 mg, 0.279 mmol) and 66 mg of oven-dried Celite in one portion at room temperature. The resulting mixture was allowed to stir at room temperature for about 12 hours. TLC showed the complete consumption of starting material. The mixture was directly purified by column chromatography. Flash column chromatography eluted with 50% ethyl acetate afforded the ketone III(c) as a mixture (~1:1) of diastereoisomers as a viscous oil in 85% yield. Data for III(c): $^1$H NMR (CDCl$_3$, 400 MHz): δ 7.99-7.94 (m, 4H), 7.65-7.60 (m, 2H), 7.57-7.54 (m, 4H), 2.8 (br, 2H), 2.39-2.34 (m, 2H), 2.29-2.14 (m, 4H), 2.04-1.94 (m, 4H), 1.92-1.58 (m, 10H), 1.54-1.35 (m, 6H), 1.28-1.20 (m 2H), 1.12-0.91 (m, 6H), 0.81 (d, 3H, J=6.4 Hz), 0.77 (d, 3H, J=6.4 Hz), 0.79-0.69 (m, 4H), 0.58 (s, 3H), 0.55 (s, 3H). $^{13}$C NMR (CDCl$_3$, 100 MHz): δ 211.65, 139.98, 133.10, 133.02, 129.02, 128.92, 61.75, 57.09, 57.00, 49.85, 40.15, 38.81, 38.78, 37.82, 37.36, 33.62, 27.49, 27.43, 23.89, 19.00, 18.94, 12.71, 12.52, 12.49, 12.44, 11.83. IR (Thin Film) 3278 (m), 2957 (s), 2874 (m), 1708 (s), 1445 (sh, m), 1378 (w), 1220 (br, s), 1109 (w), 968 (m), 749 (m) cm$^{-1}$. HRMS: calculated for C$_{22}$H$_{31}$NO$_2$SNa$^+$ [M+Na]: 396.1967 Found: 396.1955.

Example 12

24-Phenyl Sulfoximines I(n) and I(o)

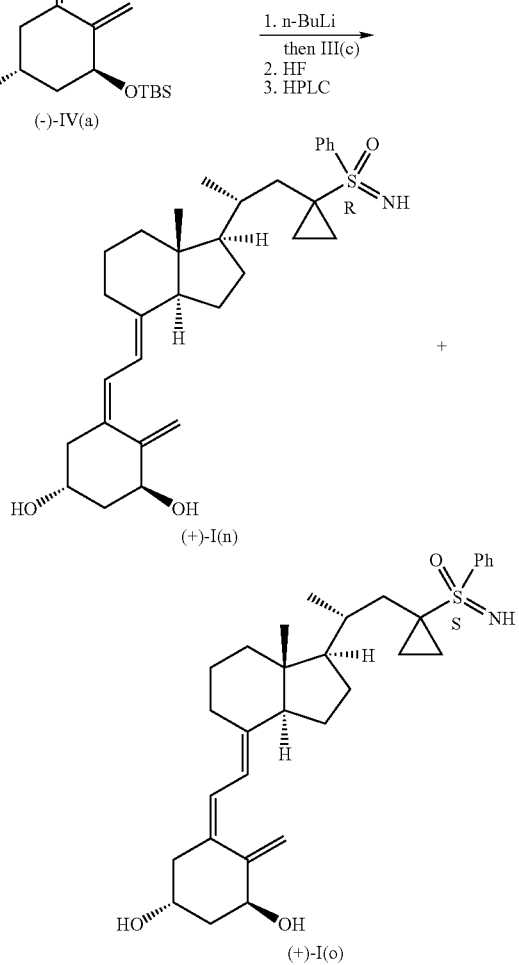

Prior to reaction, the phosphine oxide (±)-IV(a) (Posner, G. H. et al. *J. Med. Chem.* 1992, 35, 3280-3287) and CD-ring ketone (+)-I(c) were azeotrophically dried with benzene and left under vacuum for 48 h. Under argon, the phosphine oxide (±)-IV(a) (63.5 mg, 0.11 mmol) was dissolved in 1.1 mL freshly distilled THF to give ca. 0.1 M solution in a flame-dried 10 mL flask, and the flask was cooled down to −78° C. in an isopropanol/dry ice bath. To this solution was added n-BuLi (82 µL, 0.11 mmol, 1.33 M solution in hexanes) dropwise over several minutes during which time a deep red color developed and persisted. This mixture was allowed to stir at −78° C. for an additional 10 min. Meanwhile, a flame-dried 10-mL recovery flask equipped with a magnetic stir bar, a septum along with an Ar balloon was charged with CD-ring ketone (+)-III(c) (15 mg, 0.04 mmol) dissolved in 1 mL freshly distilled THF and cooled down to −78° C. in an isopropanol/dry ice bath. The solution of CD-ring ketone was gently transferred dropwise into the flask containing the phoshine oxide anion at −78° C. via cannula over several minutes. After the addition was complete, the deep red color persisted and the mixture was allowed to stir at 78° C. for ca. 8 hours during which time it was visually checked. Upon observation of the light yellow color, the reaction was quenched at −78° C. by addition of 5 mL of pH 7 buffer and allowed to come to room temperature. The mixture was then rinsed into a separatory funnel with ethyl acetate and extracted with ethyl acetate (4×25 mL). The combined extracts were washed with water (1×25 mL) and brine solution (1×25 mL), dried over $Na_2SO_4$ and filtered. The filtrate was concentrated in vacuo to give the crude product which was purified by column chromatography eluted with 50% ethyl acetate in hexanes in the presence of 1% triethylamine to afford the coupled product.

The coupled product (15 mg, 0.02 mmol) in a 5 mL argon purged polypropylene vial equipped with a magnetic stir bar was dissolved in 1.0 mL anhydrous acetonitrile to give ca. 0.02 M solution. To this well-stirred solution was added 83 µL of HF (2.0 mmol, 49% aqueous solution) via syringe at room temperature and the mixture was then allowed to stir at room temperature in the dark for 2 hours. TLC showed the completion of the reaction. The reaction mixture was diluted with ether (25 mL) and saturated solution of $NaHCO_3$ was added until no more carbon dioxide was liberated. The reaction mixture was then rinsed into a separatory funnel with ethyl acetate and was extracted with ethyl acetate (5×25 mL). The combined extracts were washed with water (1×25 mL), and brine solution (1×25 mL), dried over $Na_2SO_4$ and filtered. The filtrate was concentrated in vacuo to give the crude product that was purified by column chromatography.

Flash column chromatography eluted with 99% ethyl acetate in the presence of 1% triethylamine to afford 8.2 mg of a mixture of diastereomers (+)-I(n) and (+)-I(o) in 79% yield and in a ratio of 1:1 respectively. The diastereomeric mixture was then separated by HPLC using a Chiralcel OJ column (Semipreparative (1×25 cm), flow rate=2.0 mL/min) eluted with 7% ethanol in hexanes to afford 1.2 mg (+)-I(n) and 1.9 mg (+)-I(o) in 30% and 48% yields, respectively. The retention time for (+)-I(n) was 123.3 min, and for (+)-I(o) was 137.5 min.

Data for (+)-I(n): $[\alpha]_D$=+8.5 (c=0.08, $CHCl_3$) $^1$H NMR ($CDCl_3$, 400 MHz): δ 7.97-7.94 (m, 2H), 7.62-7.58 (m, 1H), 7.55-7.51 (m, 2H), 6.36 (d, 1H, J=11.6 Hz), 5.98 (d, 1H, J=11.2 Hz), 5.33 (m, 1H) 4.99 (br, 1H), 4.45-4.41 (m, 1H), 4.26-4.20 (m, 1H), 2.80 (dd, 1H, J=4.4 Hz, J=12.8 Hz), 2.59 (dd, 1H, J=3.6 Hz, J=13.6 Hz), 2.50 (s, 1H), 2.31 (dd, 1H, J=6.8, 13.6 Hz), 2.15 (d, 1H, J=14.4 Hz); 2.05-1.99 (m, 1H), 1.95-1.88 (m, 4H), 1.77-1.59 (m, 5H), 1.48-1.20 (m, 7H), 1.11-0.86 (m, 2H), 0.75 (d, 3H, J=6.0 Hz), 0.75-0.72 (m, 2H), 0.46 (s, 3H). $^{13}$C NMR ($CDCl_3$, 100 MHz): δ 147.62, 142.74, 141.50, 133.06, 129.38, 128.77, 128.46, 124.87, 117.17, 111.76, 70.82, 66.84, 57.05, 56.19, 54.1, 45.93, 45.24, 42.88, 40.33, 37.80, 34.11, 28.96, 27.61, 23.45, 22.21, 19.13, 12.29 (2C), 12.01. IR: 3330 (br, m), 2931 (s), 2872 (m), 1443 (m), 1219 (s), 1072 (m), 961. (sh, s), 890 (w) 749 (s) $cm^{-1}$. HRMS: calculated for $C_{31}H_{43}NO_3SNa^+$ [M+Na]: 532.2855. Found: 532.2826. UV (MeOH) $\lambda_{max}$ 265 nm (ϵ 9,024).

Data for (+)-I(o): $[\alpha]_D$=+37.7 (c=0.12, $CHCl_3$) $^1$H NMR ($CDCl_3$, 400 MHz): δ 7.98-7.95 (m, 2H), 7.63-7.59 (m, 1H), 7.56-7.52 (m, 2H), 6.36 (d, 1H, J=11.2 Hz), 5.99 (d, 1H, J=11.2 Hz), 5.33 (m, 1H) 4.99-4.98 (br, m, 1H), 4.45-4.41 (m, 1H), 4.26-4.17 (m, 1H), 2.79 (dd, 1H, J=4.0 Hz, J=12.4 Hz), 2.59 (dd, 1H, J=3.6 Hz, J=13.6 Hz), 2.54 (s, 1H), 2.31 (dd, 1H, J=6.4, 13.6 Hz), 2.13 (d, 1H, J=14.8 Hz), 2.05-1.99 (m, 1H), 1.95-1.88 (m, 4H), 1.77-1.59 (m, 5H), 1.48-1.20 (m, 7H), 1.11-0.86 (m, 2H), 0.73 (d, 3H, J=6.4 Hz), 0.76-0.70 (m, 2H), 0.49 (s, 3H). $^{13}$C NMR ($CDCl_3$, 100 MHz): δ 147.59, 142.70, 140.75, 133.08, 129.47, 128.78, 128.55, 124.84, 117.18, 111.79, 70.80, 66.81, 56.94, 56.18, 45.92, 45.22, 42.85, 40.32, 40.29, 37.40, 34.13, 28.95, 27.66, 23.44, 22.22, 19.11, 12.41, 12.03, 11.74. IR: 3334 (br, m), 2936 (s), 2872 (m), 1445 (m), 1284 (s), 1215 (br, m), 1119 (m), 1053 (br, s), 978 (w) 753 (s) $cm^{-1}$.

HRMS: calculated for $C_{31}H_{43}NO_3SNa^+$ [M+Na]: 532.2855. Found: 532.2860. UV (MeOH) $\lambda_{max}$ 265 nm (ϵ 15,684).

Example 13 p-Fluorophenylmethyl Sulfoximine VII(d) Protected with TBSCl

Scheme 33

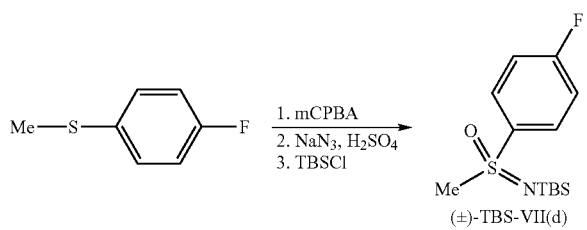

A flame-dried 25-mL recovery flask equipped with a magnetic stir bar, a septum, an addition funnel along with an Ar balloon was charged with 4-fluorophenylmethylsulfide (1 g, 7 mmol) and dissolved in 14 mL freshly distilled $CH_2Cl_2$. Then the flask was cooled down to 0° C. in an ice bath. To this solution was added mCPBA (1.9 g 7.7 mmol, 70%) as a solution in 5 mL $CH_2Cl_2$ dropwise via addition funnel over several minutes. This mixture was allowed to stir at 0° C. for an additional 2 hours. TLC showed complete consumption of starting material. The reaction was quenched by addition of water, then rinsed into a separatory funnel with 50 mL $CH_2Cl_2$. The mixture was extracted with $CH_2Cl_2$ (3×25 mL). The combined extracts were washed with sat. $NaHCO_3$ solution (1×10 mL), brine solution (1×10 mL), dried over $Na_2SO_4$ and filtered. The filtrate was concentrated in vacuo to give the crude product that was purified by flash column chromatography eluted first with 100% ethyl acetate affording the corresponding sulfoxide as an oil in 90% yield (1 g, 6.3 mmol).

A 25-mL flame-dried recovery flask equipped with a magnetic stir bar, a septum, and an addition funnel along with an Ar balloon was charged with the sulfoxide (1 g, 6.3 mmol) and dissolved in 6.3 mL $CHCl_3$. Then, (0.45 g, 6.9 mmol) of $NaN_3$ was added into the flask in one portion. Meanwhile, 1.53 mL of con. $H_2SO_4$ was charged into the addition funnel and allowed to drip into the reaction flask at 0° C. over several minutes. The addition funnel was then replaced with a reflux condenser and flask was placed into an oil bath and heated to 45° C. for overnight. TLC showed complete consumption of the starting material. The reaction flask was cooled down to room temperature and the reaction was quenched by addition of water, then rinsed into a separatory funnel with 50 mL CHCl₃. The mixture was extracted with CHCl₃ (3×25 mL). The combined extracts were washed with brine solution (1×10 mL), dried over Na₂SO₄ and filtered. The filtrate was concentrated in vacuo to give the crude product that was purified by flash column chromatography eluted with 100 V₀ ethyl acetate affording 0.81 g sulfoximine VII(d) as a solid in 74% yield. This was recrystallized from ethyl acetate. Product data for p-fluorophenylmethyl sulfoximine: mp. 93-94° C. $^1$H NMR (CDCl₃, 400 MHz): δ 8.06-8.02 (m, 2H), 7.26-7.21 (m, 2H), 3.12 (s, 3H), 2.76 (br, 1H). $^{13}$C NMR (CDCl₃, 100 MHz): δ 165.37 (d, J=253.7 Hz), 139.4 (d, J=2.7 Hz), 130.5 (d, J=9.1 Hz), 116.3 (d, J=22.8 Hz), 46.3. $^{19}$F NMR (CDCl₃, 375 MHz): δ− 105.60-105.7 (m). IR: 3268 (m), 3102 (w), 2928 (w), 1589 (s), 1493 (s), 1404 (w), 1321 (w), 1224 (s), 1094 (s), 1021 (m), 1004 (s), 946 (m), 840 (m), 817 (m), 753 (m) cm$^{-1}$. HRMS: calcd for C₇H₈FNOSNa⁺ [M+Na]: 196.0202. found: 196.0201.

A flame-dried 5-mL recovery flask equipped with a magnetic stir bar, a septum along with an Ar balloon was charged with p-fluorophenylmethyl sulfoximine (0.1 g, 0.58 mmol) and dissolved in 1.1 mL anhydrous pyridine to give ca. 0.5 M solution. To this solution was added TBSCl (0.1 g 0.69 mmol) as neat in one portion. This mixture was allowed to stir at room temperature 12 hours. TLC showed complete consumption of the starting material. The reaction was quenched by addition of water, then rinsed into a separatory funnel with 25 mL ethyl acetate. The mixture was extracted with ethyl acetate (3×25 mL). The combined extracts were washed with brine solution (1×10 mL), dried over Na₂SO₄ and filtered. The filtrate was concentrated in vacuo to give the crude product that was purified by flash column chromatography eluted with 10% ethyl acetate affording the sulfoximine TBS-protected VII(d) as an oil in 90% yield (0.15 g, 0.52 mmol). $^1$H NMR (CDCl₃, 400 MHz): δ 7.97-7.93 (m, 2H), 7.20-7.14 (m, 2H), 2.99 (s, 3H), 0.91 (s, 9H), 005 (s, 3H), 0.04 (s, 3H). $^{13}$C NMR (CDCl₃, 100 MHz): δ 164.9 (d, J=252.9 Hz), 141.2 (d, J=3.0 Hz), 129.6 (d, J=8.1 Hz), 116.0 (d, J=22.0 Hz), 49.7, 25.9, 17.9, −2.57. $^{19}$F NMR (CDCl₃, 375 MHz): 8-107.3-107.4 (m). IR: 2954 S), 2958 (s), 2885 (s), 2855 (s), 1589 (m), 1493 (m), 1322 (s), 1302 (s), 1284 (s), 1250 (m), 1163 (s), 1150 s), 1090 (w), 1006 (w), 953 (w), 834 (s), 814 (m), 774 (s) cm$^{-1}$. HRMS: calcd for C₁₃H₂₂FNOSSiNa⁺ [M+Na]: 310.1067. found: 310.1043.

Example 14

24-Phenyl Sulfoximines I(p) and I(q)

Scheme 34

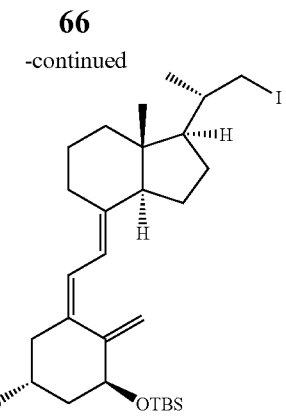

TBS-Protected (±)-VII(d)

+

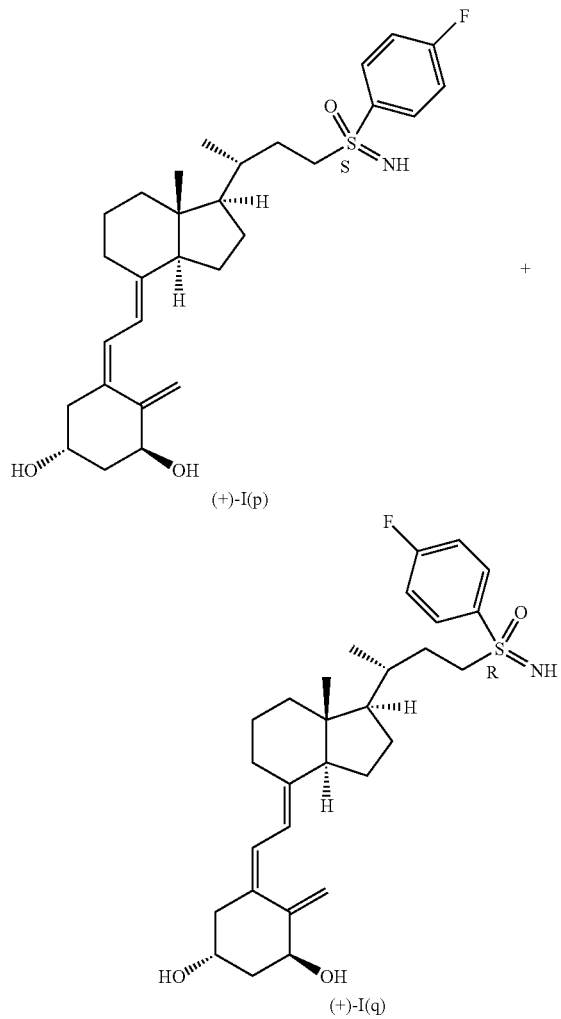

A flame-dried 5 mL recovery flask equipped with a magnetic stir bar, a septum along with an Ar balloon was charged with (±)-VII(a) (8.4 mg, 0.029 mmol) and dissolved in 0.5 mL freshly distilled THF. Then the flask was cooled down to −78° C. in an isopropanol/dry ice bath. To this solution was added 19 µL of n-BuLi (0.03 mmol, 1.6 M solution in hexanes) dropwise over several minutes followed by addition of 50 µL HMPA, resulting in a yellow color. This mixture was allowed to stir at −78° C. for an additional 30 min. Meanwhile, a flame-dried 5 mL pear shaped flask equipped with a septum along with an Ar balloon was charged with iodide (+)-IX (5 mg, 0.0073 mmol), dissolved in 0.5 mL freshly distilled THF and cooled down to −78° C. in an isopropanol/dry ice bath. The solution of iodide (+)-IX was transferred into the flask containing the lithiated sulfoximine at −78° C. via cannula over a few minutes. After the addition was complete, the mixture was stirred at −78° C. for about 4-5 hours. TLC showed almost complete consumption of (+)-IX. The reaction was quenched by addition of 2 mL pH 7 buffer, then rinsed into a separatory funnel with ethyl acetate. The mixture was extracted with ethyl acetate (3×10 mL). The combined extracts were washed with water (1×10 mL), and brine solution (1×10 mL), dried over Na$_2$SO$_4$ and filtered. The filtrate was concentrated in vacuo to give the coupled product that was purified by flash column chromatography eluted first with 100 mL of 100% hexanes, then 10% ethyl acetate in hexanes.

An argon purged 5 mL polypropylene vial equipped with a magnetic stir bar along with a cap was charged with the coupled product (3.4 mg, 0.004 mmol) and was dissolved in 0.4 mL anhydrous acetonitrile to give ca. 0.01 M solution. To this well-stirred solution was added 0.16 µL of HF (0.44 mmol, 49% aqueous solution) via syringe at room temperature and the mixture was then allowed to stir at room temperature in the dark for 4 hours. TLC showed the completion of the reaction. This reaction mixture was diluted with ether (10 mL) and saturated solution of NaHCO$_3$ was added until no more carbon dioxide was liberated. The reaction mixture was then rinsed into a separatory funnel with ethyl acetate and was extracted with ethyl acetate (4×10 mL). The combined extracts were washed with water (1×10 mL), brine solution (1×10 mL), dried over Na$_2$SO$_4$ and filtered. The filtrate was concentrated in vacuo to give the crude product which was purified by flash column chromatography eluted with 99% ethyl acetate in the presence of 1% triethylamine to afford 1.7 mg of (+)-I(p) and (+)-I(q) in 84% yield. This was further purified by HPLC using a Chiralcel OJ column (Semipreparative (1×25 cm), flow rate=2.5 mL/min) eluted with 13% ethanol in hexanes to afford 0.51 mg (+)-I(p) and 0.37 mg (+)-I(q) in 19% and 26%, respectively. The retention time for (+)-I(p) is 78.0 min and for (+)-I(q) is 61.0 min. Data for (+)-I(p): $[\alpha]_D$=+12.3 (c=0.09, CHCl$_3$) $^1$H NMR (CDCl$_3$, 300 MHz): δ 8.00-7.95 (m, 2H), 7.25-7.20 (m, 2H), 6.36 (d, 1H, J=11.22 Hz), 5.99 (d, 1H, J=11.22 Hz), 5.32 (br, s, 1H), 4.98 (br, s, 1H), 4.44-4.30 (m, 1H), 4.23-4.22 (m, 1H), 3.23-3.15 (m, 1H), 3.07-2.97 (m, 1H), 2.66 (br, 1H), 2.60 (dd, 1H, J=3.39 Hz, 13.26 Hz), 2.30 (dd, 1H, J=5.61 Hz, 13.29 Hz), 2.04-1.88 (m, 4H), 1.81-1.44 (m, 1H), 1.30-1.12 (m, 4H), 0.88 (d, 3H, J=6.33 Hz), 0.50 (s, 3H). $^{19}$F NMR (CDCl$_3$, 375 MHz): δ −105.75-105.78 (m). IR (neat) 3299 (m), 2926 (s), 2869 (s), 1587 (m), 1491 (w), 1446 (w), 11401 (w), 1350 (m), 1220 (s), 1016 (w), 1057 (w), 994 (m), 836 (w), 752 (s) cm$^{-1}$. HRMS: calcd for C$_{29}$H$_{40}$FNO$_3$SNa$^+$ [M+Na]: 524.2605. found: 524.2610. UV (MeOH), 263 nm (ε 11,096). Data for (+)-I(q): $[\alpha]_D$=+22.6 (c=0.05, CHCl$_3$) $^1$H NMR (CDCl$_3$, 300 MHz): δ 8.00-7.95 (m, 2H), 7.25-7.19 (m, 2H), 6.36 (d, 1H, J=11.22 Hz), 5.99 (d J=11.31 Hz), 5.32 (br, s, 1H), 4.98 (br, s, 1H), 4.45-4.40 (m, 1H), 4.24-4.18 (m, 1H), 3.22-3.00 (m, 2H), 2.80 (dd, 1H, J=3.81 Hz, 11.82 Hz), 2.67 (br, 1H), 2.59 (dd, 1H, J=3.48 Hz, 13.38 Hz), 2.31 (dd, 1H, J=6.36 Hz, 13.44 Hz), 2.06-1.87 (m, 3H), 1.55-1.41 (m, 11H), 1.29-1.15 (m, 4H), 0.88 (d, 3H, J=6.39 Hz), 0.50 (s, 3H). $^{19}$F NMR 375 MHz): δ −105.72-105.78 (m). IR (neat) 3294 (m), 2921 (s), 2866 (m), 1583 (m), 1490 (m), 1348 (m), 1222 (s), 1096 (m), 1052 (m), 997 (m), 838 (w), 750 (s) cm$^{-1}$. HRMS: calcd for C$_{29}$H$_{40}$FNO$_3$SNa$^+$ [M+Na]: 524.2605. found: 524.2619. UV (MeOH) λ$_{max}$ 263 nm (ε 10,895).

Example 15

Preparation of Sulfoximine IX

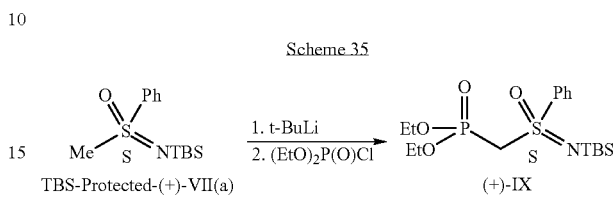

Scheme 35

A flame-dried 10-mL recovery flask equipped with a magnetic stir bar, a septum along with an Ar balloon was charged with (+)—S-methyl-S-phenyl sulfoximine (43 mg, 0.1595 mmol) and dissolved in 1.5 mL freshly distilled THF. Then the flask was cooled down to −78° C. in an isopropanol/dry ice bath. To this solution was added 0.16 mL of t-BuLi (0.1755, 1.1 M solution in pentane) dropwise over several minutes resulting in a yellow color. This mixture was allowed to stir at −78° C. for an additional 30 min. To this solution was added diethylchlorophosphate (41.3 mg, 35 µL, 0.2393 mmol). After the addition was complete, the mixture was stirred at −78° C. for about 1 hours. TLC showed that the starting matarial was entirely consume. Reaction was quenched by addition of water (5 mL) and then the mixture was rinsed into a separatory funnel extracted with ethyl acetate (3×10 mL). The combined extracts were washed with water (1×10 mL), brine solution (1×10 mL), dried over Na$_2$SO$_4$ and filtered. The filtrate was concentrated in vacuo to give the crude product. The crude was purified by flash chromatography eluted with a 9:1 mixture of ethyl acetate:hexanes to give 34 mg of (+)-IX as an oil in 53% yield. Data for (+)-IX: $[\alpha]_D^{22}$=+40.3 (c 0.55, CHCl$_3$). $^1$H NMR (CDCl$_3$, 300 MHz): δ 7.99-7.97 (m, 2H), 7.58-7.48 (m, 3H), 4.13-4.02 (m, 4H), 3.73 (dd, 1H, J=3.6 Hz, 15.2 Hz), 3.68 (dd, 1H, J=15.2 Hz), 1.28-1.21 (m, 6H), 0.91 (s, 9H), 0.05 (s, 6H). $^{13}$C NMR (CDCl$_3$ MHz) δ 144.46, 132.47, 128.55, 127.83, 62.74 (d, J=6.1 Hz), 62.55, (d, J=6.1 Hz), 58.02 (d, J=135.8 Hz), 25.85, 17.96, 16.22 (d, J=2.1 Hz), 16.16 (d, J=2.3 Hz), −2.63, −2.65 ppm. IR (neat) 3066 (w), 2955 (m), 2929 (m), 2855 (m), 1473 (m), 1446 (m), 1391 (m), 1361 (m), 1320 (m), 1300 (s), 1253 (s), 1167 (s), 1052 (s), 1025 (s), 974 (m), 834 (s), 778 (m), 689 (m) cm$^{-1}$. HRMS: calcd for C$_{17}$H$_{32}$NO$_4$PSSiNa$^+$ [M+Na]: 443.1451. found: 428.1435.

Example 16

24-Phenyl Sulfoximines I(r) and I(s) (C22-C23 Double Bond)

Scheme 36

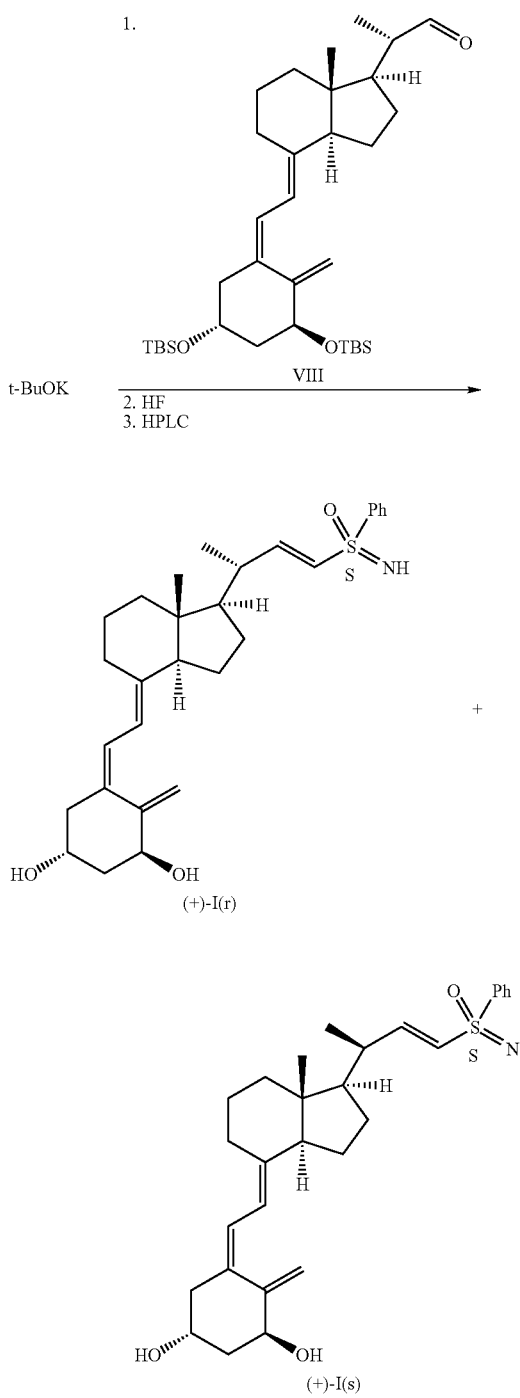

A flame-dried 5-mL recovery flask equipped with a magnetic stir bar, a septum along with an Ar balloon was charged with (±)-IX (4.2 mg, 0.01 mmol) and dissolved in 0.5 mL freshly distilled THF. Then the flask was cooled down to −78° C. in an isopropanol/dry ice bath. To this solution was added 13 μL of t-BuOK (0.013 mmol, 1.0 M solution in THF) dropwise over several minutes resulting in a yellow color. This mixture was allowed to stir at −78° C. for an additional 30 min. Meanwhile, a flame-dried 5-mL pear shaped flask equipped with a septum along with an Ar balloon was charged with VIII (5.0 mg, 0.0087 mmol) dissolved in 1.0 mL freshly distilled THF and cooled down to −78° C. in an isopropanol/dry ice bath. The solution of VIII was transferred into the flask containing the anion of (±)-IX at −78° C. via cannula over a few minutes. After the addition was complete, the mixture was stirred at −78° C. for about 1.0 hours. Then the flask was warmed up to room temperature and allowed to stir for 1.5 hours. TLC showed the consumption of the starting material. Reaction was quenched by addition of water (5 mL) and then the mixture was rinsed into a separatory funnel extracted with ethyl acetate (3×10 mL). The combined extracts were washed with water (1×10 mL), brine solution (1×10 mL), dried over $Na_2SO_4$ and filtered. The filtrate was concentrated in vacuo to give the coupled product. The coupled product was purified by flash chromatography eluted with 10% ethyl acetate in hexanes to give 5.4 mg in 71% yield.

An argon purged 5 mL polypropylene vial equipped with a magnetic stir bar along with a cap was charged with the coupled product (5.0 mg, 0.006 mmol) and dissolved in 0.6 mL anhydrous acetonitrile to give ca. 0.01 M solution. To this well-stirred solution was added 0.25 μL of HF (0.6 mmol, 49% aqueous solution) via syringe at room temperature and the mixture was then allowed to stir at room temperature in the dark for 4 hours. TLC showed the completion of the reaction. This reaction mixture was diluted with ether (10 mL) and saturated solution of $NaHCO_3$ was added until no more carbon dioxide was liberated. The reaction mixture was then rinsed into a separatory funnel with ethyl acetate and was extracted with ethyl acetate (3×10 mL). The combined extracts were washed with water (1×10 mL), brine solution (1×10 mL), dried over $Na_2SO_4$ and filtered. The filtrate was concentrated in vacuo to give the crude product which was passed through a pad of silica gel to afford 2.3 mg of a mixture of (+)-I(r) and (+)-I(s) in 79% yield. This was further purified by HPLC using a Chiralcel OJ column (Semipreparative (1×25 cm), flow rate=2.5 mL/min) eluted with 17% ethyl acetate in hexanes to afford 800 μg of (+)-I(r) and 540 μg of (+)-I(r) in 28% and 19% yields, respectively. Data for (+)-I(r): $^1$H NMR (CDCl$_3$, 300 MHz) δ 7.96-7.93 (m, 2H), 7.61-7.48 (m, 3H), 6.83 (dd, 1H, J=8.9 Hz, J=15.0 Hz), 6.35 (d, 1H, J=12.60 Hz), 6.31 (d, 1H, J=15.00 Hz), 5.98 (d, 1H, J=10.83 Hz), 5.31 (s, 1H) 4.97 (s, 1H), 4.48-4.38 (m, 1H), 4.28-4.18 (m, 1H), 2.84-2.79 (m, 2H), 2.62-2.57 (m, 1H), 2.34-2.28 (m, 2H) 2.06-1.88 (m, 4H), 1.69-1.33 (m, 7H), 1.33-1.22 (m, 4H), 1.11 (d, 3H, J=6.6 Hz), 0.52 (s, 3H). HRMS: calcd for $C_{29}H_{39}NO_3SNa^+$ [M+Na]: 504.2543. found: 504.2530. UV (MeOH), 261 nm (F 12,799). Data for (+)-I(r): $^1$H NMR (CDCl$_3$, 300 MHz) δ 7.96-7.94 (m, 2H), 7.61-7.48 (m, 3H), 6.83 (dd, 1H, J=89.8 Hz, J=15.0 Hz), 6.35 (d, 1H, J=8.3 Hz), 6.31 (d, 1H, J=15.00 Hz), 5.98 (d, 1H, J=11.16 Hz), 5.31 (s, 1H) 4.97 (s, 1H), 4.47-4.38 (m, 1H), 4.28-4.18 (m, 1H), 2.81-2.76 (m, 2H), 2.60-2.57 (m, 1H), 2.34-2.25 (m, 2H) 2.06-1.87 (m, 4H), 1.62-1.37 (m, 7H), 1.33-1.25 (m, 4H), 0.99 (d, 3H, J=6.6 Hz), 0.42 (s, 3H). HRMS: calcd for $C_{29}H_{39}NO_3SNa^+$ [M+Na]: 504.2543. found: 504.2543. UV (MeOH) m 265 nm (ε 7,718).

Example 17
Proposed Preparation of Compound (S)-I(t)—Method A
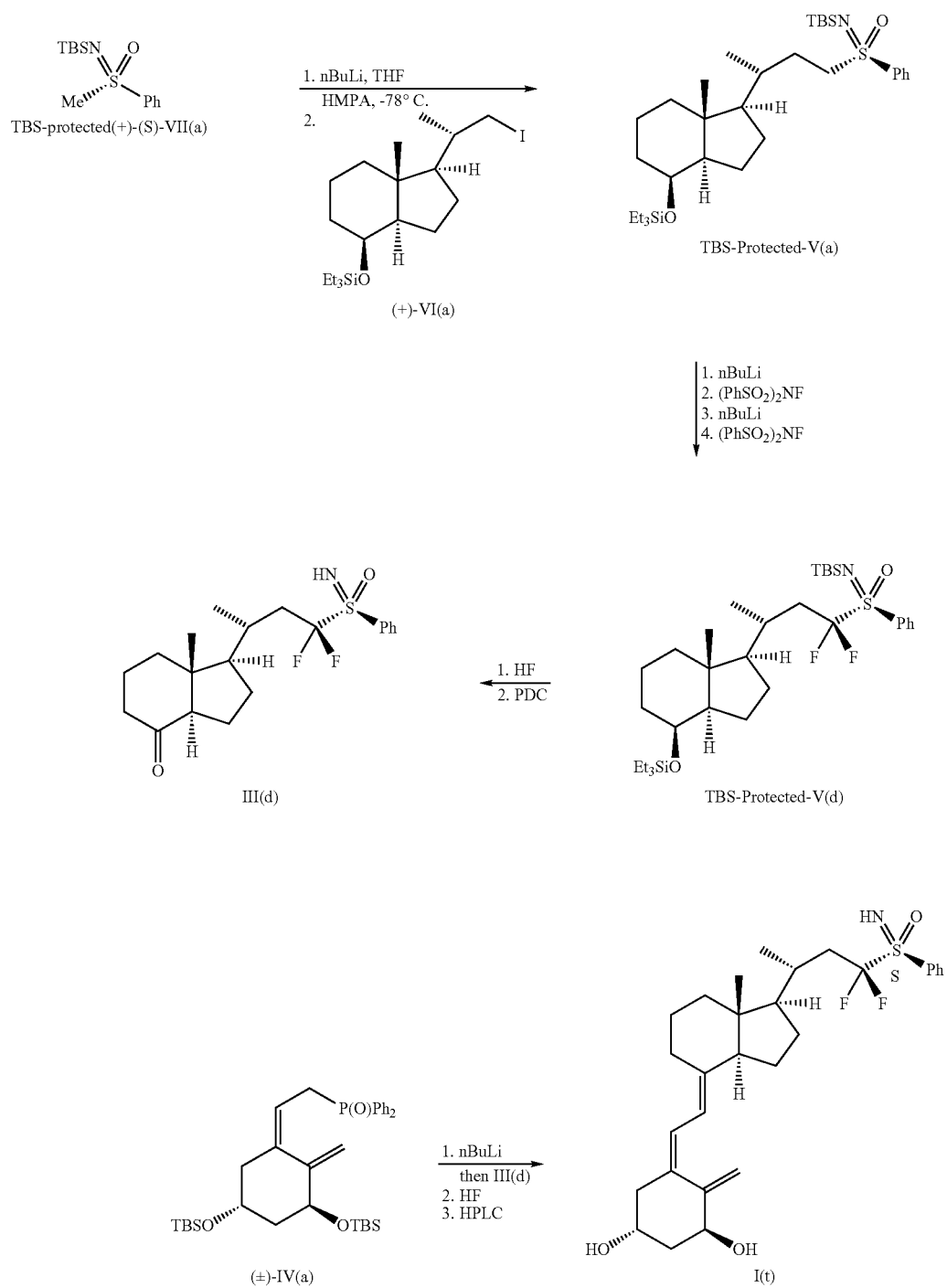

In a like manner, compound (R)-I(t) may be prepared from TBS-protected (R)-VII(a).
Example 18
Proposed Preparation of Compound (S)-I(t)—Method B
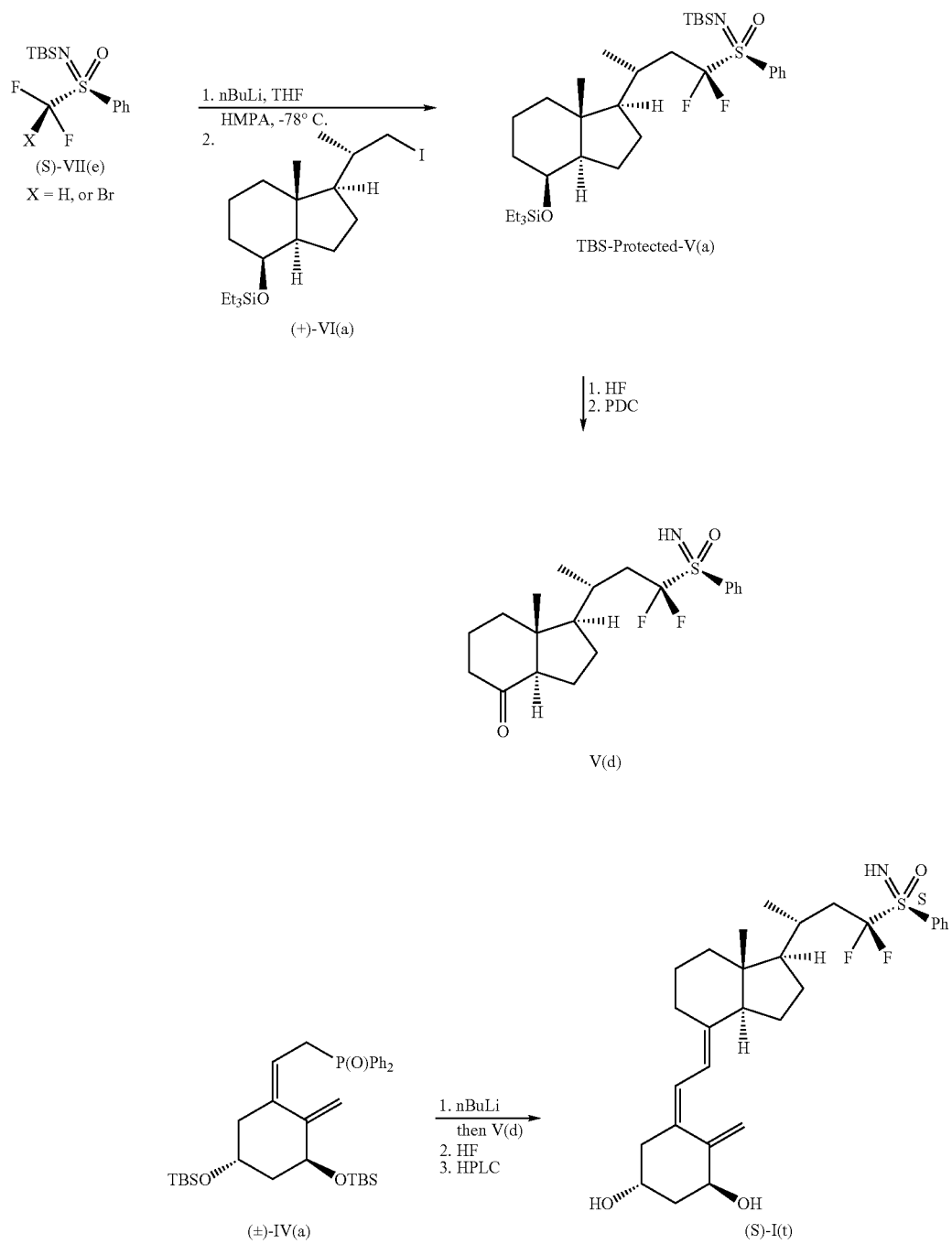

In a like manner, compound (R)-I(t) may be prepared from TBS-protected (R)-VII(e).
Example 19
Proposed Preparation of Compound (S)-I(u)
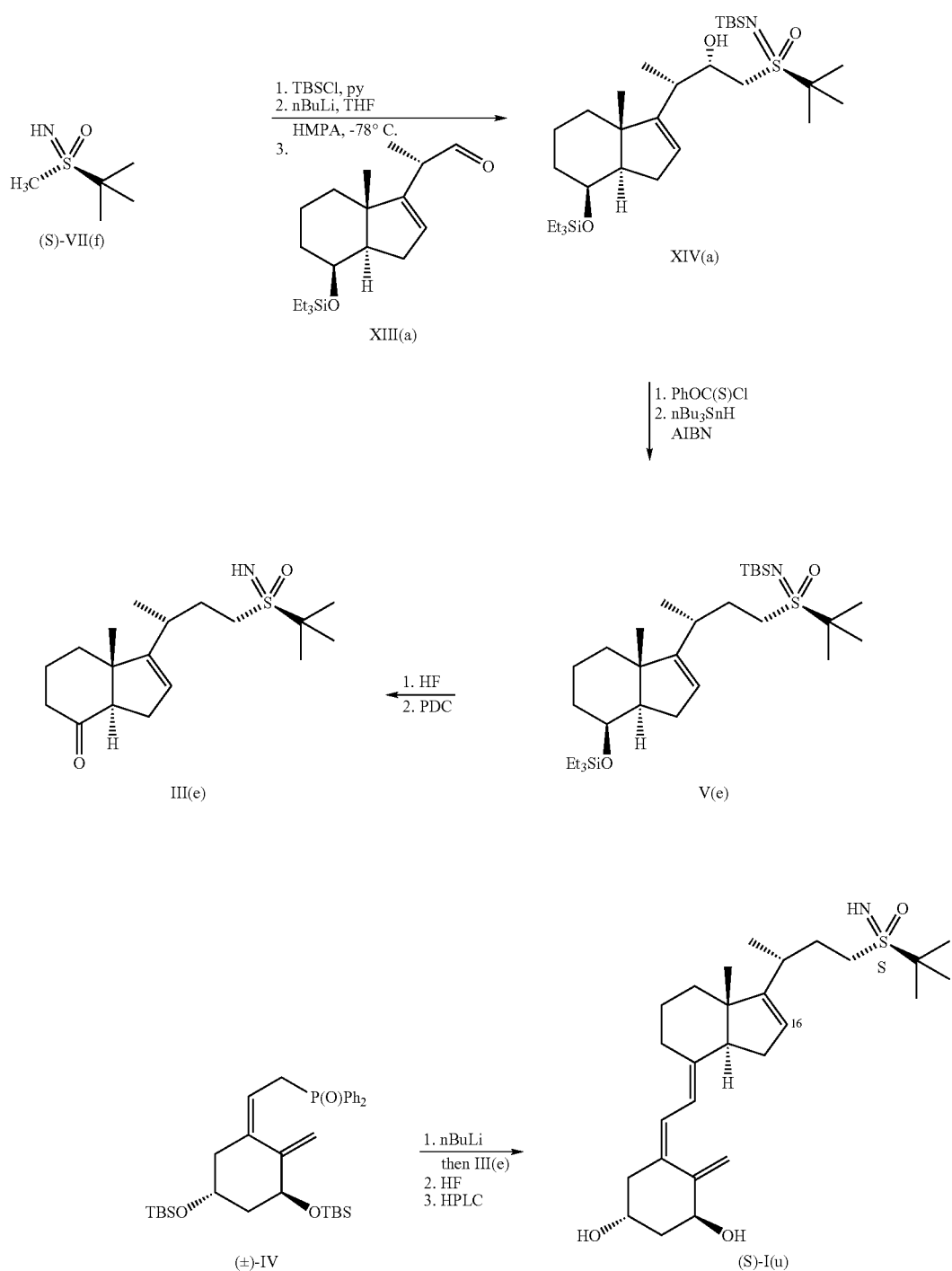

In a like manner, compound (R)-I(u) may be prepared from (R)-VII(f).

Example 20

Proposed Preparation of Compound (S)-I(v)

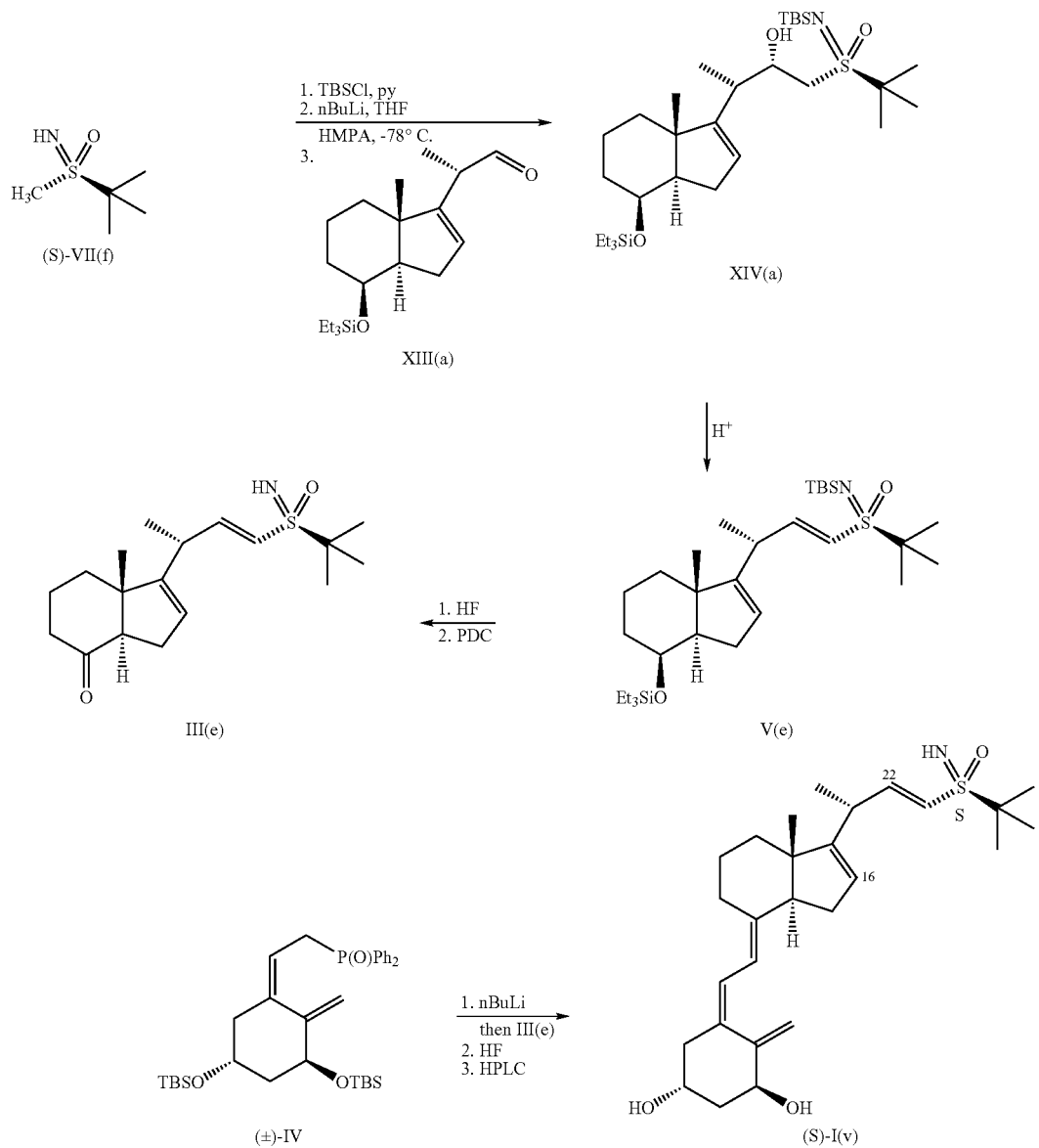

Aliquot 1 μl of 1.25(OH)$_2$D$_3$ 5×10$^{-3}$ M stock solution to 499 μl of isopropanol to make 1.25(OH)$_2$D$_3$ 10$^{-5}$ working solution. Store at −20° C. until needed.
[$^3$H]-1.25(OH)$_2$D$_3$ 16,000 cpm/mL, 8 μM (Perkin Elmer, Boston, Mass.)
HPK1A-ras cells (obtained from Dr. Glenville Jones, Queens University, Kingston, Ontario, Canada)

In a like manner, compound (R)—I(v) may be prepared from (R)-VII(f).

Example 21

CYP24 Enzyme Assay (Induced HPK1A-ras Cells)

(i) Material and Reagents:
1.25(OH)$_2$D$_3$ 10$^{-5}$ M (Sigma, St. Louis, Mo.);
Preparation of 10$^{-5}$ M working solution is as follows:
Dissolve 1 mg of 1,25(OH)$_2$D$_3$ into 480 μl of isopropanol to make 5×10$^{-3}$ M stock solution. Store at −70° C. until needed.

48-well plate
Methanol
Dichloromethane
Saturated KCl: KCl 30 g, H$_2$O 400 ml
1,2-Dianilinoethane (DPPD)
Ketoconazole (Sigma, St. Louis, Mo.)
(ii) Procedure:
1. Induction of HPK1A-ras cells (The day before assay)
When the HPK1A-ras cells were 80-90% confluent, added 1 μL 10$^{-5}$ M 1.25(OH)$_2$D$_3$ to 1 mL medium in the plate (final concentration is 10$^{-8}$ M).

2. Preparation of cell suspension
   After 18 to 20 hours induction, removed the medium and washed the cell twice with PBS. Then tripsinized the cells from plate, centrifuged (2,000 rpm, 5 min) and suspended cells pellet in DMEM medium+1% BSA. Counted the cells and adjusted cells density to 250,000/150 μL, added 150 μL cell suspension to each well in 48-well plate (including 3 wells as a no cell control, and 3 well cells without drug or inhibitor as controls).
3. Added 25 μL ketoconazole (final concentration $10^{-5}$ M, $10^{-6}$ M, $10^{-7}$ M, $10^{-8}$ M) or Drugs (final concentration $10^{-6}$ M, $10^{-7}$ M, $10^{-8}$ M, $10^{-9}$ M) into each designated well. Kept the plate in 37° C. for 10 min.
4. Preparation of substrate
   For each ml required, added 972 μl of DMEM+1% BSA medium, 20 μl of 3H-1,25$(OH)_2D_3$, and 8 μl of 100 nM DPPD to a tube and vortexed.
5. Incubation
   Added 25 μL substrate to each well, incubated the plate at 37° C. for 2 hour.
   Added 25 μL substrate to counting plate (2 well) as a total count.
6. Lipid Extraction and Counting
   Added 500 μL methanol to each well to stop the reaction, transferred them to tube.
   Added 250 μL dichloromethane and vortex.
   Added 250 μL dichloromethane and 250 mL saturated KCl, and vortex.
   Centrifuged at 4000 rpm for 5 min.
   Transferred 100 μL of aqueous phase (upper phase) to counting plastic counting plate. Added 600 μL of scintillation fluid to each well. Counted the plate in scintillation counter.
7. Calculation Enzyme Activity
   CPM of cell control after subtraction of CPM of non-cell control (NCC) was as 100% enzyme activity.

Enzyme activity=(*CPM* in test compounds well–*CPM* in *NCC* well)/(*CPM* in Cell control–*CPM* in *NCC* well)*100%

Dilution of Ketoconazole
Stock $10^{-2}$ M

| Concentration (final) | From previous step (μL) | DMEM + 1% BSA (μL) | Concentration (actual) |
|---|---|---|---|
| $10^{-5}$ M | 4 | 496 | $8 \times 10^{-5}$ M |
| $10^{-6}$ M | 12.5 | 112.5 | $8 \times 10^{-6}$ M |
| $10^{-7}$ M | 12.5 | 112.5 | $8 \times 10^{-7}$ M |
| $10^{-8}$ M | 12.5 | 112.5 | $8 \times 10^{-8}$ M |

Dilution of test compounds
Stock $10^{-3}$ M

| Concentration (final) | From previous step (μL) | DMEM + 1% BSA (μL) | Concentration (actual) |
|---|---|---|---|
| $10^{-6}$ M | 4 | 496 | $8 \times 10^{-6}$ M |
| $10^{-7}$ M | 12.5 | 112.5 | $8 \times 10^{-7}$ M |
| $10^{-8}$ M | 12.5 | 112.5 | $8 \times 10^{-8}$ M |
| $10^{-9}$ M | 12.5 | 112.5 | $8 \times 10^{-9}$ M |

(iii) Results are shown in Table 1
(iv) References:
Ray S, Ray R, Holick M. Metabolism of $^3$H-1 alpha, 25-dihydroxy vitamin $D_3$ in the cultured human keratinocytes (1995) 59:117-122

Dilworth F J, Scott I, Green A, Strugnell S, Guo Y D, Roberts E A, Kremer R, Calverley, M J, Makin H L J, Jones G. Different mechanisms of hydroxylation site selection by liver and kidney cytochrome P450 species (CYP27 and CYP24) involved in Vitamin D metabolism. (1995) J Biochem 270(28): 16766-16774.

Example 22

CYP24 Enzyme Assay (Using Stable Cell Line—V79-CYP24 Cells)

(i) Material and Reagents
1α,25$(OH)_2D_3$ 1 mM reconstituted in isopropanol
Substrates (1 mM) reconstituted in isopropanol
V79-CYP24 cells
DMEM media supplemented with hygromycin and 10% fetal bovine serum
DMEM+1% BSA media DPPD
48-well plate
methanol
dichloromethane
saturated KCl: KCl 30 g, $H_2O$ 400 ml
ketoconazole (ii) Procedure:
1. Preparation of Cell Suspension
   On the day of the assay, washed the monolayer of V79-CYP24 cells once with 1×PBS buffer and then trypsinize for 5 min at room temperature (approx. 22° C.). Added 1×PBS. Collected cells into tube, centrifuged cells (500×g, 5 min) and resuspended in DMEM+1% BSA media. Counted cells and adjusted density to 250,000 cells/150 μl (1.67 million/1 mL).
2. Cell Plating
   Added 150 μl of cell suspension to appropriately labelled wells of a 48-well plate. Incubated plate for 30 minutes at 37° C. in a humidified atmosphere containing 5% $CO_2$ for adherence of cells to wells.
3. Compound Addition
   Added 25 μl of inhibitor ($10^{-6}$ to $10^{-9}$ M) and then after 10 min added 25 μl of substrate [$^3$H-1β]-1α,25$(OH)_2D_3$ (20 nM) for 2 hours at 37° C. in a humidified atmosphere containing 5% $CO_2$. Both inhibitor and substrate were prepared in DMEM with 1% BSA media in the absence and presence of 100 μM DPPD.
4. Lipid Extraction and Counting
   Added 500 μL of methanol to stop the reaction. Transferred to tube. Added 250 μl of dichloromethane and vortexed. Added 250 μl of dichloromethane and 250 μl of saturated KCL and vortexed. Centrifuged at 4000 rpm for 5 min. Triplicate 100 μl aliquots of aqueous fraction were mixed with 600 μl of scintillation fluid and the radioactivity was measured using a scintillation counter. All values were normalized for background.

(iii) Results.
   Shown in Table 1
(iv) Reference.
1. PCT Patent Application Serial No. PCT/CA03/00620

Example 23

CYP27A1 Enzyme Assay (A) Procedure:
   As described in:
Dilworth F J, Black S M, Guo Y D, Miller W L, Jones G. Construction of a P450c27 fusion enzyme: a useful tool for analysis of vitamin $D_3$ 25-hydroxylase (1996) Biochem J 320:267-271

Sawada N, Sakaki T, Ohta M, Inouye K. Metabolism of vitamin D (3) by human CYP27A1 (2000) Biochem Biophys Res Commun 273(3):977-84

(B) Results:

See Table 1.

Example 24

VDR Bindiny Assay (i) Reagent and Materials
1. VDR 9.4 pmol/μl (human, recombinant, Biomol).
2. [$^3$H]-1.25(OH)$_2$D$_3$ in ethanol
3. 1.25(OH)$_2$D$_3$ in ethanol
4. TEK$_{300}$
Tris-HCI 50 mM
EDTA 1.5 mM
KCI 300 mM
Adjust pH to 7.4 (25° C.)
5. TEDK$_{300}$
TEK$_{300}$
DTT (dithiothreitol) 10 mM*MW 154.24)
6. Tris buffer
22.50 g Tris-HCI
500 ml H$_2$O
13.25 g Tris-base
500 ml H$_2$O
Kept in 4° C.
7. Dextran-T70 (Mol 70,000) Pharmacia
8. Charcoal (carbon decolorizing neutral, norit) Fisher Scientific
9. Gelatin (G-2625 Sigma)

(ii) Reagent Preparation
1. Charcoal Dextran Solution
   (1) Tris Buffer
   Mixed equal amount of Tris-HCI and Tris-base.
   (2) Norit decolorizing neutral charcoal 2.0 g
   Tris buffer 150 mL
   Stirred
   (3) Dextran T—70 0.2 g
   Tris buffer 50 ml.
   (4) Slowly driped the suspended dextran into charcoal solution with stirring.
   Kept in refrigerater overnight.
   Thirty minutes before use, stored on ice with continuous mixing.
2. TEK$_{300}$/Gelatin Solution
   50 mg swine gelatin
   5 ml TEDK$_{300}$ solution
   heated, stirred then cooled to 4° C.
   5 ml TEDK$_{300}$ solution
3. Preparation of 1.25(OH)$_2$D$_3$ and test compounds in ethanol
   1.25(OH)$_2$D$_3$: 125, 250, 500, 1000, 2000, 4000 pg/25 μl.
   (stock 10-5 M/25 μL=100,000 pg/25 μL)

| Concentration (ng/mL) | Amount (pg/50 μL) |
|---|---|
| 5.0 | 125 |
| 10.0 | 250 |
| 20.0 | 500 |
| 40.0 | 1000 |
| 80.0 | 2000 |
| 160.0 | 4000 |

Test compounds: 12,500, 25,000, 50,000, 100,000, 200,000 and 400,000 pg/25 μL. (4*10−5M/25 μL=400,000 pg/25 μL)

4. Dilution of VDR:
   1 μl stock VDR in 2.5 ml TEDK$_{300}$/Gelatin solution (500 μl/tube), (keep on ice)

(iii) Procedure

1. Reaction Setup

Label tubes according to the following chart, each in triplicate:

| No VDR Control | No VD3 Control | Standard | Test Compounds |
|---|---|---|---|
| Add 25 μL ethanol | Add 25 μL ethanol | Add 25 μL of each standard (in each concentration) | Add 25 μL of each sample (in each concentration) |
| Add 500 μL TEDK300/gelat in solution | Add 500 μL VDR working solution | Add 500 μL VDR working solution | Add 500 μL VDR working solution |

Mixed all tubes via vortex and incubated at room temperature for 1 hour. Added 10 μL of 3H-1,25(OH)$_2$D$_3$ Working Dilution, mixed by vortex and incubated at room temperature for 1 hour 2. Sample processing Thirty minutes before addition, put Charcoal/Dextran Solution on ice with continuous mixing. Added 100 mL of Charcoal/Dextran Solution to each tube, mixed well and incubated on ice for 30 minutes. Centrifuged @ 2000 rpm for 10 minutes at 4° C.

3. Counting

Pipetted 100 μL of the upper, aqueous phase to a 24 well scintillation counting plate and added 600 μL scintillation fluid per well, covered and mixed well. Counted the plate using a scintillation counter for 5 min/sample.

(iv) Calculations:

The amount of 1,25(OH)$_2$D$_3$ to displace 50 percent [$^3$H]-1,25(OH)$_2$D$_3$ from VDR was calculated as B$_{50}$ for 1,25(OH)$_2$D$_3$. The VDR binding of other compounds was calculated as B$_{50}$ relative to a value of 1 for 1,25(OH)$_2$D$_3$.

Serial Dilution of 1,25(OH)D$_3$

| Concentration (pg/25 μl) | Final concentration M | 10$^{-5}$ M (μl) | Ethanol (μl) |
|---|---|---|---|
| 4,000 | $2 \times 10^{-8}$ | 6 | 144 |
| 2,000 | $10^{-8}$ | 70 | 70 |
| 1,000 | $5 \times 10^{-9}$ | 70 | 70 |
| 500 | $2.5 \times 10^{-9}$ | 70 | 70 |
| 250 | $1.25 \times 10^{-9}$ | 70 | 70 |
| 125 | $6.25 \times 10^{-10}$ | 70 | 70 |

Serial Dilution of Test Compounds

| Concentration (pg/50 ul) | Final concentration M | $10^{-3}$ M ($\mu$l) | Ethanol ($\mu$l) |
|---|---|---|---|
| 400,000 | $2 \times 10^{-6}$ | 6 | 144 |
| 200,000 | $10^{-6}$ | 70 | 70 |
| 10,000 | $5 \times 10^{-7}$ | 70 | 70 |
| 5,000 | $2.5 \times 10^{-7}$ | 70 | 70 |
| 25,000 | $1.25 \times 10^{-7}$ | 70 | 70 |
| 12,500 | $6.25 \times 10^{-8}$ | 70 | 70 |

(v) Results:
  See Table 1
(vi) References:
1. Ross T K, Prahl J M, DeLuka H. Overproduction of rat 1,25-dihydroxy vitamin $D_3$ receptor in insect cells using the baculovirus expression system. (1991) Proc Natl Acd Sci USA 88:6555-6559
2. Wecksler W R, Norman A W. An hydroxylapatite batch assay for the quantitation of 1alpha, 25-dihydroxy vitamin $D_3$-receptor complexes (1979) Anal Biochem 92:314-323

Example 25

Figure 2:
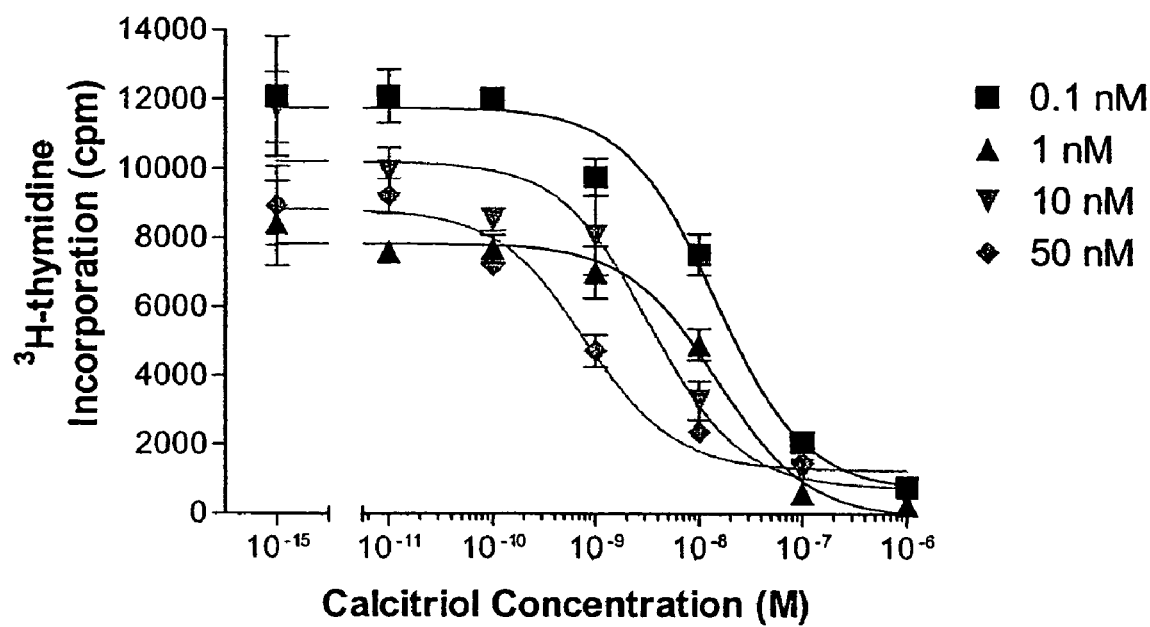
FIG. 2 is a graph showing that compound I(e) and calcitriol act to inhibit the proliferation of MCF-7 cells. MCF-7 cells were treated with specified concentrations of calcitriol and compound I(e) for three days. Cells were then incubated with [³H]-thymidine for 6 h at 37° C. in a humidified atmosphere containing 5% $CO_2$. Plates were harvested and radioactivity measured. Dose response curves in the absence of I(e) (■), 1 nM I(e) (▲), 10 nM I(e) (▼) and 50 nM I(e) (♦) are shown.
Figure 3:
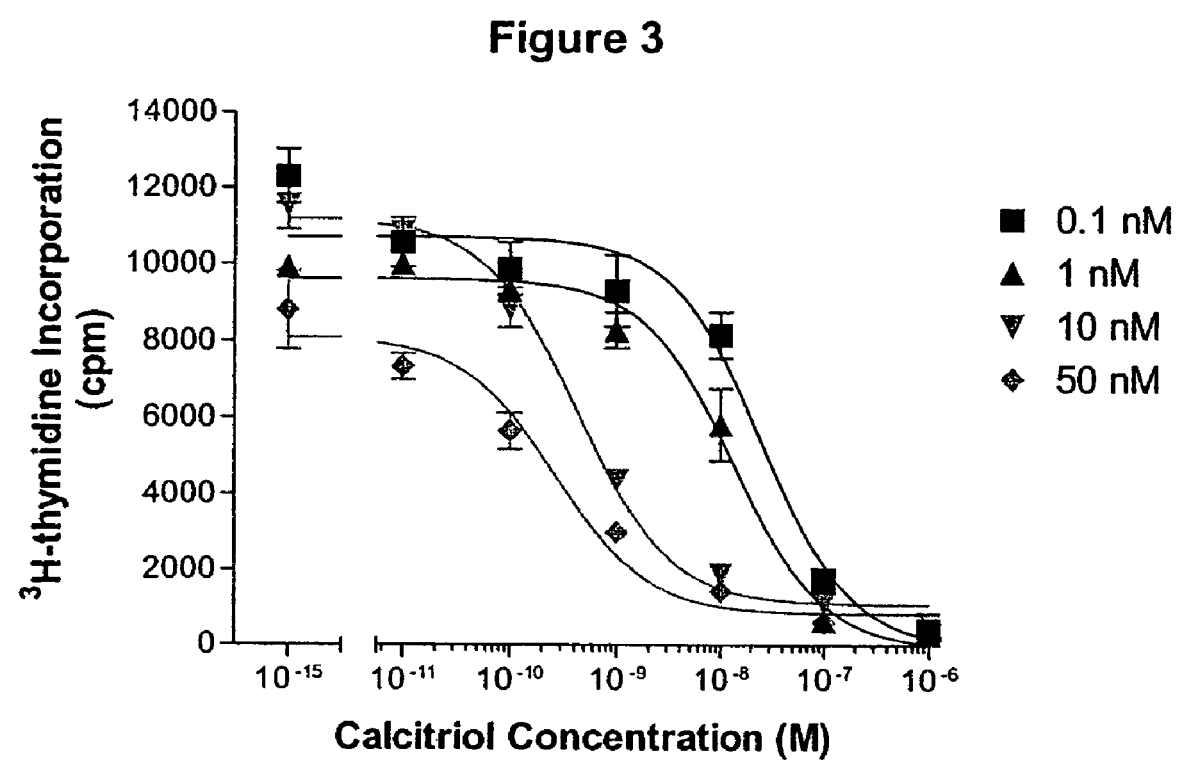
FIG. 3 is a graph showing that compound I(a) and calcitriol act to inhibit the proliferation of MCF-7 cells. MCF-7 cells were treated with specified concentrations of calcitriol and compound I(a) for three days. Cells were then incubated with [³H]-thymidine for 6 h at 37° C. in a humidified atmosphere containing 5% $CO_2$. Plates were harvested and radioactivity measured. Dose response curves for 0.1 nM I(a) (■), 1 nM I(a) (▲), 10 nM I(a) (▼) and 50 nM I(a) (♦) are shown.
Figure 4:
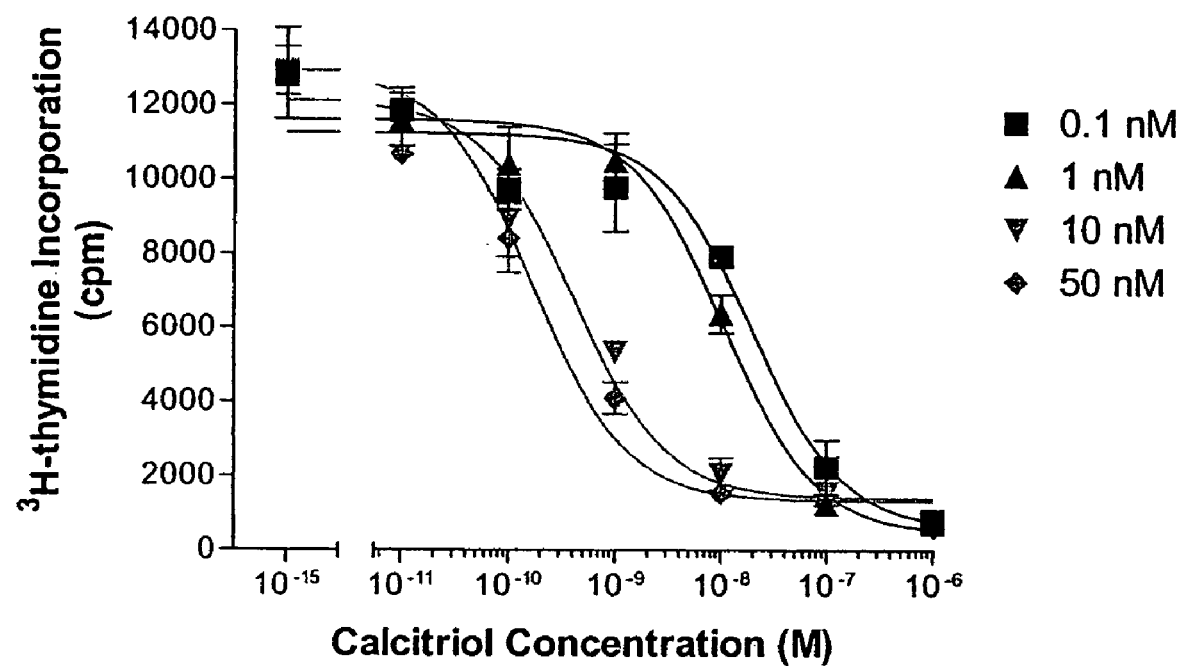
FIG. 4 is a graph showing that compound I(i) and calcitriol act to inhibit the proliferation of MCF-7 cells. MCF-7 cells were treated with specified concentrations of calcitriol and compound I(i) for three days. Cells were then incubated with [³H]-thymidine for 6 h at 37° C. in a humidified atmosphere containing 5% $CO_2$. Plates were harvested and radioactivity measured. Dose response curves for 0.1 nM I(i) (■), 1 nM I(i) (▲), 10 nM I(i) (▼) and 50 nM I(i) (♦) are shown.
Figure 5:
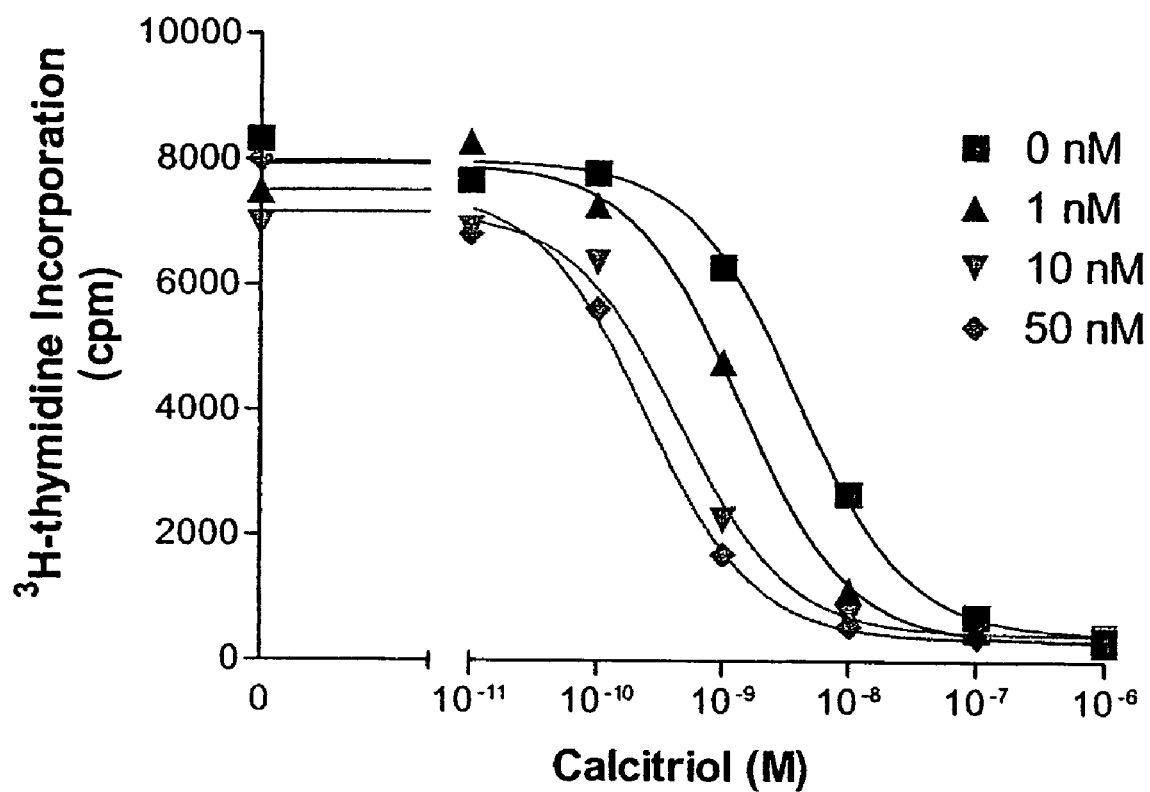
FIG. 5 is a graph showing that compound I(n) and calcitriol act to inhibit the proliferation of MCF-7 cells. MCF-7 cells were treated with specified concentrations of calcitriol and compound I(n) for three days. Cells were then incubated with [³H]-thymidine for 6 h at 37° C. in a humidified atmosphere containing 5% $CO_2$. Plates were harvested and radioactivity measured. Dose response curves in the absence of I(n) (■), 1 nM I(n) (▲), 10 nM I(n) (▼) and 50 nM I(n) (♦) are shown.

[$^3$H]-thymidine Proliferation Assay with MCF-7 Cells (i) Materials and Methods:
MCF-7 cells (ATCC)
MEM supplemented with sodium pyruvate, non-essential amino acids, bovine insulin, gentamycin and 10% Fetal bovine serum (growth media)
RPMI1640 supplemented with tri-iodothyronine, hydrocortisone, transferin, bovine insulin and 5% Fetal bovine serum (proliferation media)
$1\alpha,25(OH)_2D_3$ 1 mM reconstituted in isopropanol
substrates (1 mM) reconstituted in isopropanol
Trypsin:EDTA solution
1×PBS
75 cm$^2$ tissue culture flasks
96 well tissue culture plates
Liquid scintillation fluid
96 well filter plate (Millipore)
(ii) Procedure:
  1. Preparation of Cell Suspension
    When MCF-7 cells were 70-80% confluent, aspirated growth media. Washed the cells with 1×PBS. Trypsinized with trypsin-EDTA from the plate, collected cells from the tissue culture flask, centrifuged (500×g, 5 min) and resuspended in growth media.
  2. Cell Plating.
    Counted the cells and adjusted the cell density to 25,000/ml. Added 200 $\mu$l per well in a 96 well plate. Incubated plate for 24 h at 37° C. in a humidified atmosphere plus 5% $CO_2$. Aspirated used media and replaced with 150 $\mu$l per well with proliferation media.
  3. Substrate Addition.
    Added 25 $\mu$l of $1\alpha,25(OH)_2D_3$ (final concentration $10^{-6}$ M, $10^{-7}$ M, $10^{-8}$ M, $10^{-9}$ M, $10^{-10}$ M, $10^{-11}$ M) into each designated well. Added 25 $\mu$l of substrate (final concentration $10^{-7}$ M, $5 \times 10^{-8}$ M, $10^{-8}$ M or $10^{-9}$ M) into each designated well. Incubated plates for 3 days at 37° C. in a humidified atmosphere plus 5% $CO_2$.
  4. $^3$H-Thymidine incorporation.
    Added $^3$H-thymidine at 0.02 $\mu$Ci per well and incubated at 37° C. in a humidified atmosphere plus 5% $CO_2$ for 6 h.
  5. Plate Harvesting.
    Aspirated all media and washed cells with 1×PBS. Trypsinized cells for 30 min at 37° C. in a humidified atmosphere plus 5% $CO_2$. Harvested cells onto a 96 well filter plate (Millipore) using a Tomtec Cell Harvestor, according to manufacturers instructions.
  6. Scintillation Counting.
    Added 25 $\mu$l of scintillation fluid per well. Counted the plate using a scintillation counter.
  7. Results.
    Graphs showing results for compounds I(g), I(e), I(a), I(i), I(m) and I(n) are shown in FIGS. 1-5 respectfully.

Example 26

[$^3$H]-thymidine Proliferation Assay with SCC-25 Cells (i) Materials and Methods:
SCC-25 cells (ATCC)
DMEM-F12 supplemented with hydrocortisone and 5% Fetal bovine serum
$1\alpha,25(OH)_2D_3$ 1 mM reconstituted in isopropanol
Substrates (1 mM) reconstituted in isopropanol
Trypsin:EDTA solution
1×PBS
75 cm$^2$ tissue culture flasks
96 well tissue culture plates
Liquid scintillation fluid
96 well filter plate (Millipore)
(ii) Procedure:
  1. Preparation of Cell Suspension
    When SCC-25 cells were 70-80% confluent, aspirated media. Washed the cells with 1×PBS. Trypsinized with trypsin-EDTA from the plate, collected cells from the tissue culture flask, centrifuged (500×g, 5 min) and resuspended in media.
  2. Cell Plating.
    Counted the cells and adjusted the cell density to 10,000/ml. Added 200 $\mu$l per well in a 96 well plate. Incubated plate for 24 h at 37° C. in a humidified atmosphere plus 5% $CO_2$. Aspirated used media and replaced with 150 $\mu$l per well with media.
  3. Compound Addition.
    Added 25 $\mu$l of $1\alpha,25(OH)_2D_3$ (final concentration $10^{-6}$M, $10^{-7}$ M, $10^{-8}$ M, M, $10^{-10}$ M, $10^{-11}$ M) into each designated well. Added 25 $\mu$l of substrate (final concentration $10^{-7}$ M, $5 \times 10^{-8}$ M, $10^{-8}$ M or $10^{-9}$ M) into each designated well. Incubated plates for 3 days at 37° C. in a humidified atmosphere plus 5% $CO_2$.
  4. $^3$H-Thymidine Incorporation.
    Added $^3$H-thymidine at 0.02 $\mu$Ci per well and incubated at 37° C. in a humidified atmosphere plus 5% $CO_2$ for 6 h.
  5. Plate Harvesting.
    Aspirated all media and washed cells with 1×PBS. Trypsinized cells for 30 min at 37° C. in a humidified atmosphere plus 5% $CO_2$. Harvested cells onto a 96 well filter plate (Millipore) using a Tomtec Cell Harvestor, according to manufacturers instructions.
  6. Scintillation Counting.
    Added 25 $\mu$l of scintillation fluid per well. Counted the plate using a scintillation counter.

7. Results.

Figure 6:
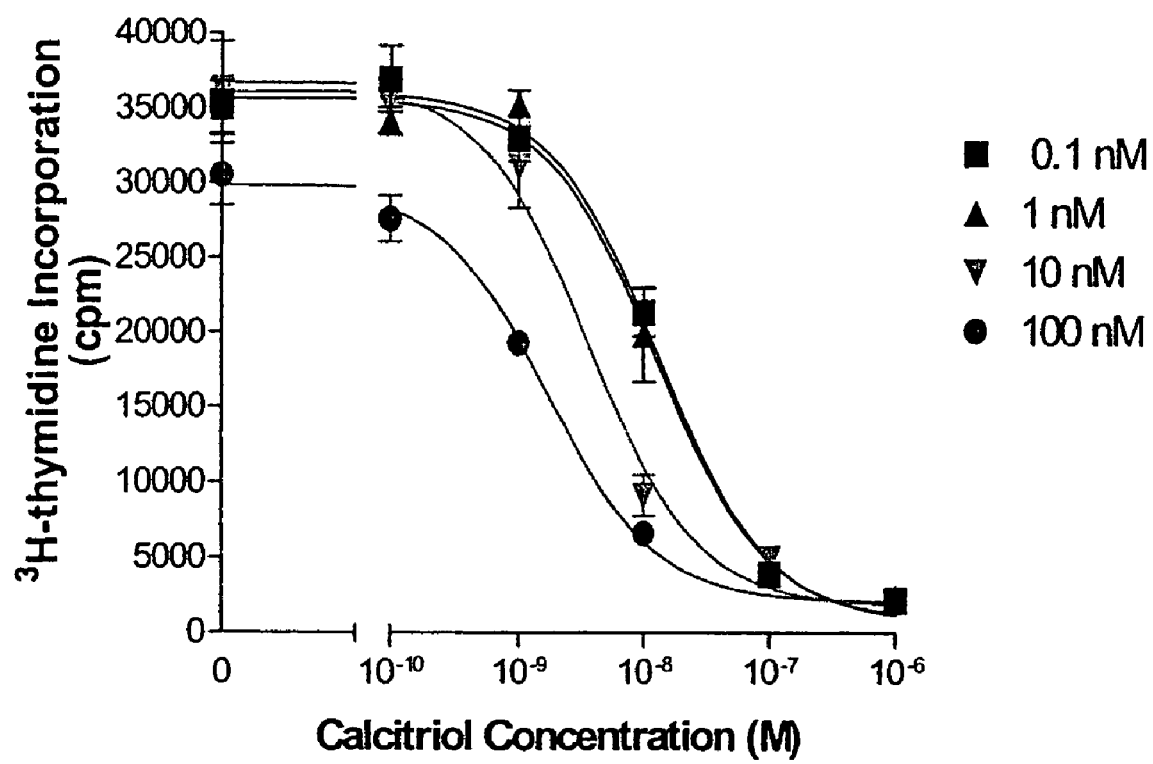
FIG. 6 is a graph showing that compound I(g) and calcitriol act to inhibit the proliferation of SCC-25 cells. SCC-25 cells were treated with specified concentrations of calcitriol and compound I(g) for three days. Cells were then incubated with [3H]-thymidine for 6 h at 37° C. in a humidified atmosphere containing 5% $CO_2$. Plates were harvested and radioactivity measured. Dose response curves for 0.1 nM I(g) (■), 1 nM I(g) (▲), 10 nM I(g) (▼) and 100 nM I(g) (♦) are shown.
Figure 7:
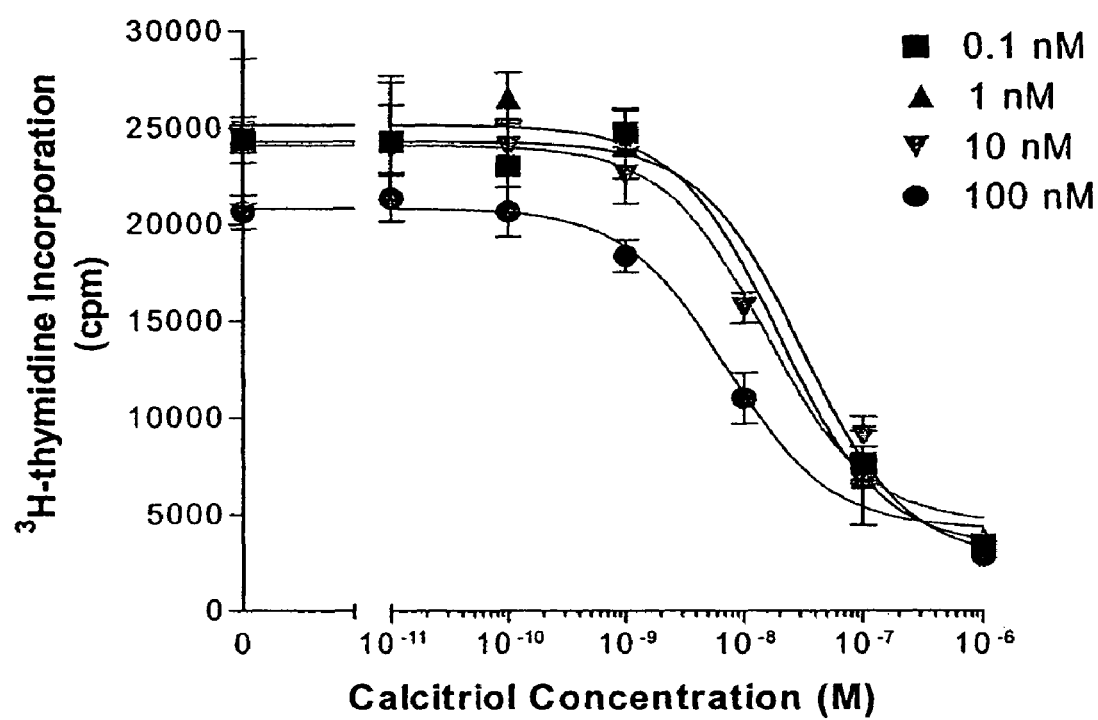
FIG. 7 is a graph showing that compound I(e) and calcitriol act to inhibit the proliferation of SCC-25 cells. SCC-25 cells were treated with specified concentrations of calcitriol and compound I(e) for three days. Cells were then incubated with [³H]-thymidine for 6 h at 37° C. in a humidified atmosphere containing 5% $CO_2$. Plates were harvested and radioactivity measured. Dose response curves for 0.1 nM I(e) (■), 1 nM I(e) (▲), 10 nM I(e) (▼) and 100 nM I(e) (♦) are shown.
Figure 8:
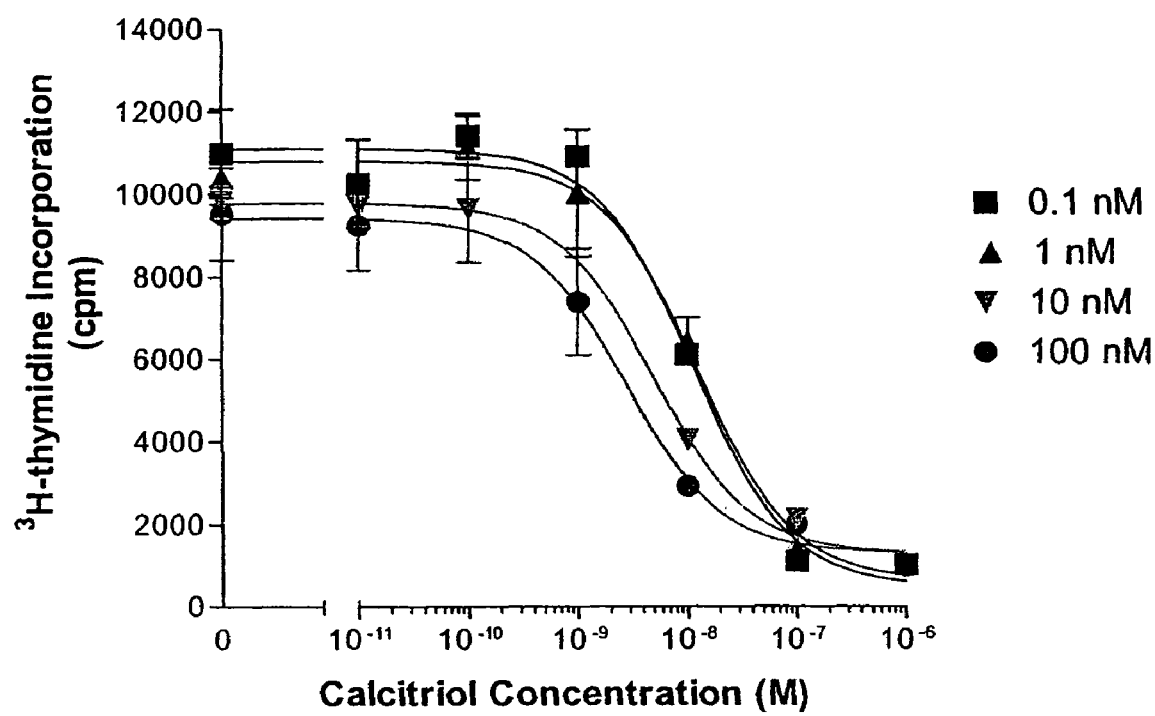
FIG. 8 is a graph showing that compound I(c) and calcitriol act to inhibit the proliferation of SCC-25 cells. SCC-25 cells were treated with specified concentrations of calcitriol and compound I(c) for three days. Cells were then incubated with [³H]-thymidine for 6 h at 37° C. in a humidified atmosphere containing 5% $CO_2$. Plates were harvested and radioactivity measured. Dose response curves for 0.1 nM I(c) (■), 1 nM I(c) (▲), 10 nM I(c) (▼) and 100 nM I(c) (♦) are shown.
Figure 9:
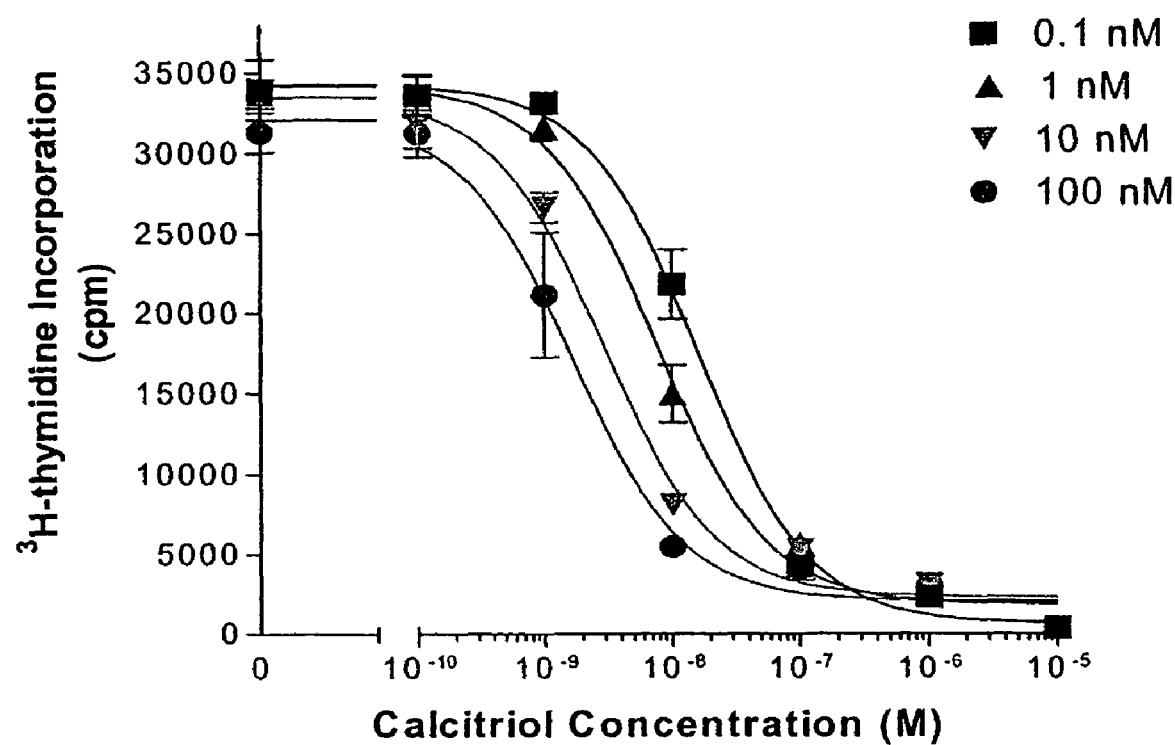
FIG. 9 is a graph showing that compound I(a) and calcitriol act to inhibit the proliferation of SCC-25 cells. SCC-25 cells were treated with specified concentrations of calcitriol and compound I(a) for three days. Cells were then incubated with [³H]-thymidine for 6 h at 37° C. in a humidified atmosphere containing 5% $CO_2$. Plates were harvested and radioactivity measured. Dose response curves for 0.1 nM I(a) (■), 1 nM I(a) (▲), 10 nM I(a) (▼) and 100 nM I(a) (♦) are shown.
Figure 10:
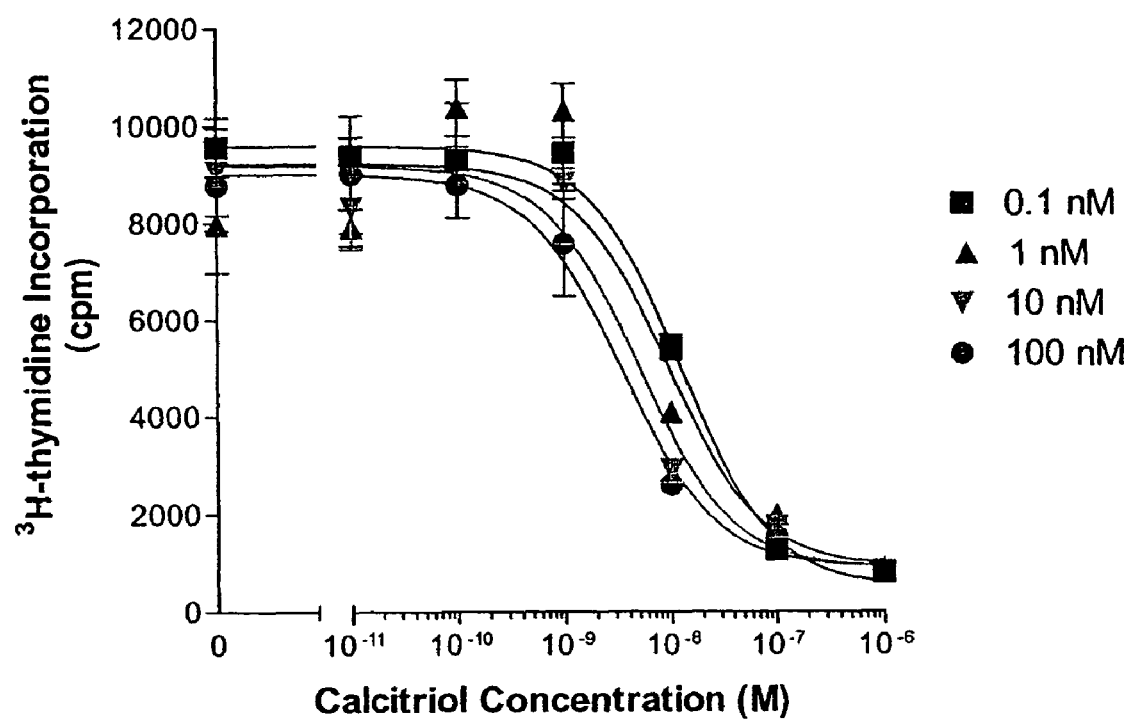
FIG. 10 is a graph showing that compound I(j) and calcitriol act to inhibit the proliferation of SCC-25 cells. SCC-25 cells were treated with specified concentrations of calcitriol and compound 10) for three days. Cells were then incubated with [³H]-thymidine for 6 h at 37° C. in a humidified atmosphere containing 5% $CO_2$. Dose response curves for 0.1 nM (j) (■), 1 nM I(j) (▲), 10 nM I(j) (▼) and 100 nM I(j) (♦) are shown.
Figure 11:
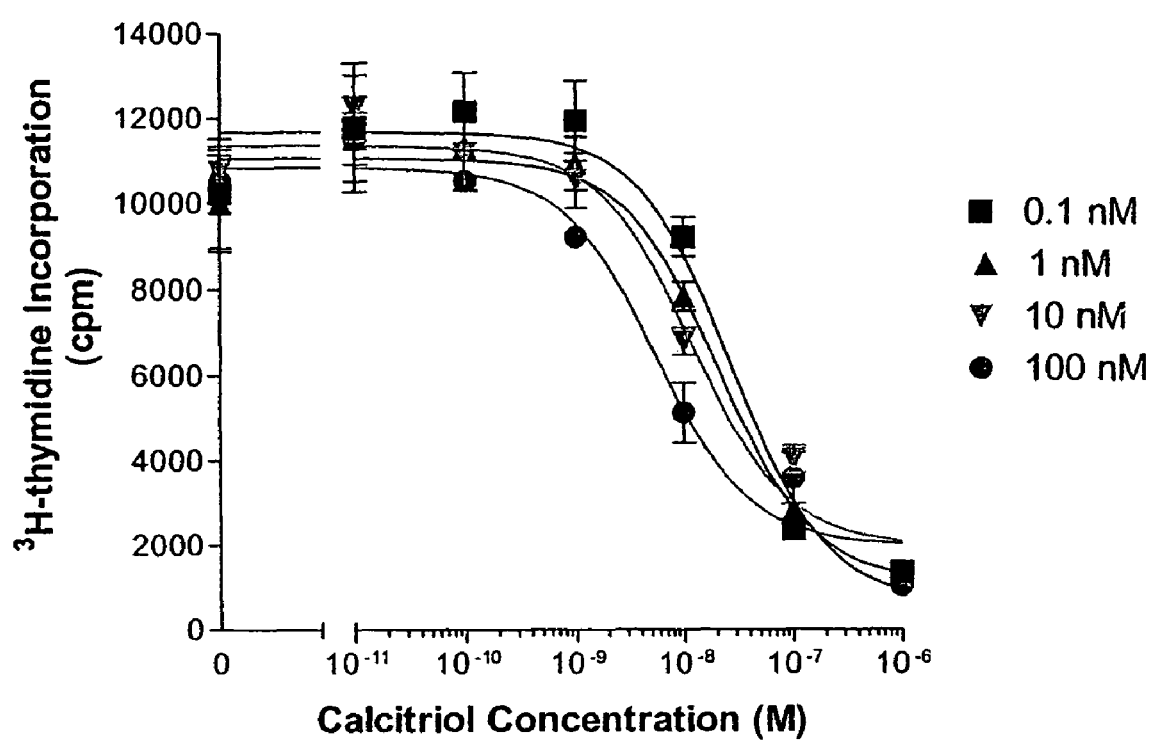
FIG. 11 is a graph showing that compound I(l) and calcitriol act to inhibit the proliferation of SCC-25 cells. SCC-25 cells were treated with specified concentrations of calcitriol and compound I(l) for three days. Cells were then incubated with [³H]-thymidine for 6 h at 37° C. in a humidified atmosphere containing 5% $CO_2$. Dose response curves for 0.1 nM I(l) (■), 1 nM I(l) (▲), 10 nM I(l) (▼) and 100 nM I(l) (♦) are shown.
Figure 12:
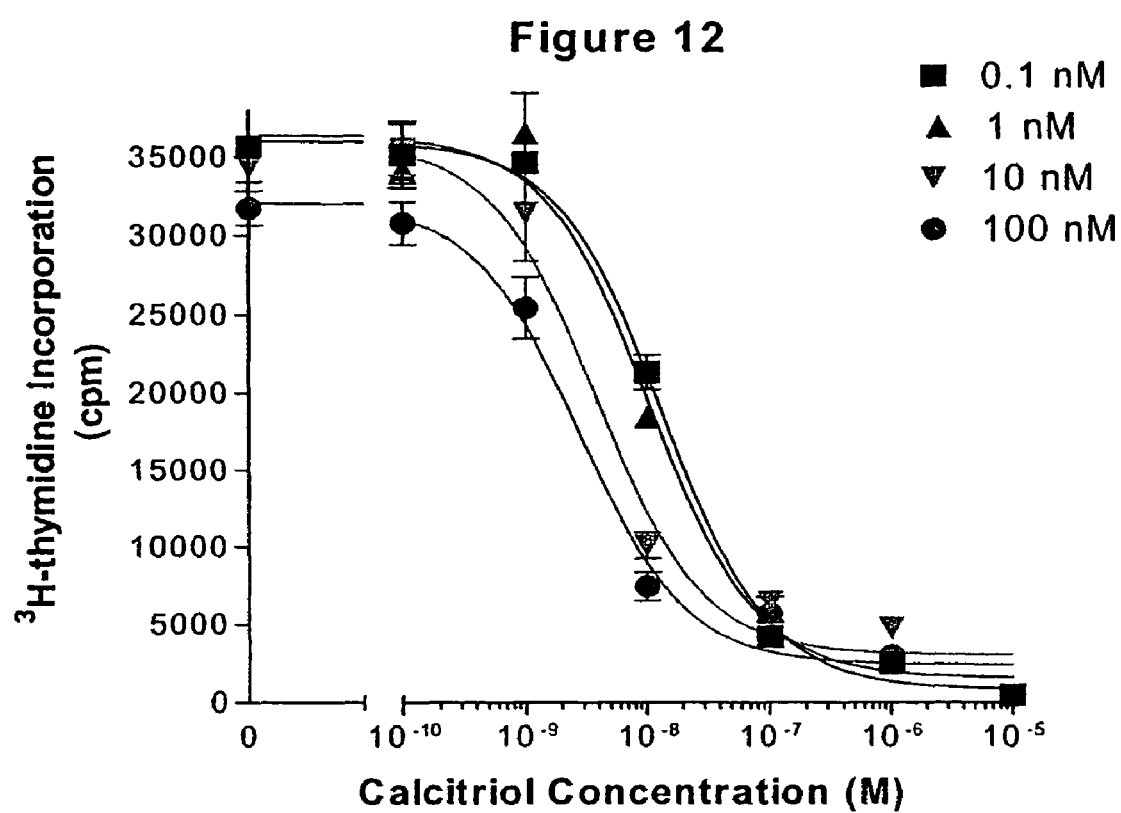
FIG. 12 is a graph showing that compound I(i) and calcitriol act to inhibit the proliferation of SCC-25 cells. SCC-25 cells were treated with specified concentrations of calcitriol and compound I(i) for three days. Cells were then incubated with [³H]-thymidine for 6 h at 37° C. in a humidified atmosphere containing 5% $CO_2$. Dose response curves for 0.1 nM I(i) (■), 1 nM I(i) (▲), 10 nM I(i) (▼) and 100 nM I(i) (♦) are shown.
Figure 13:
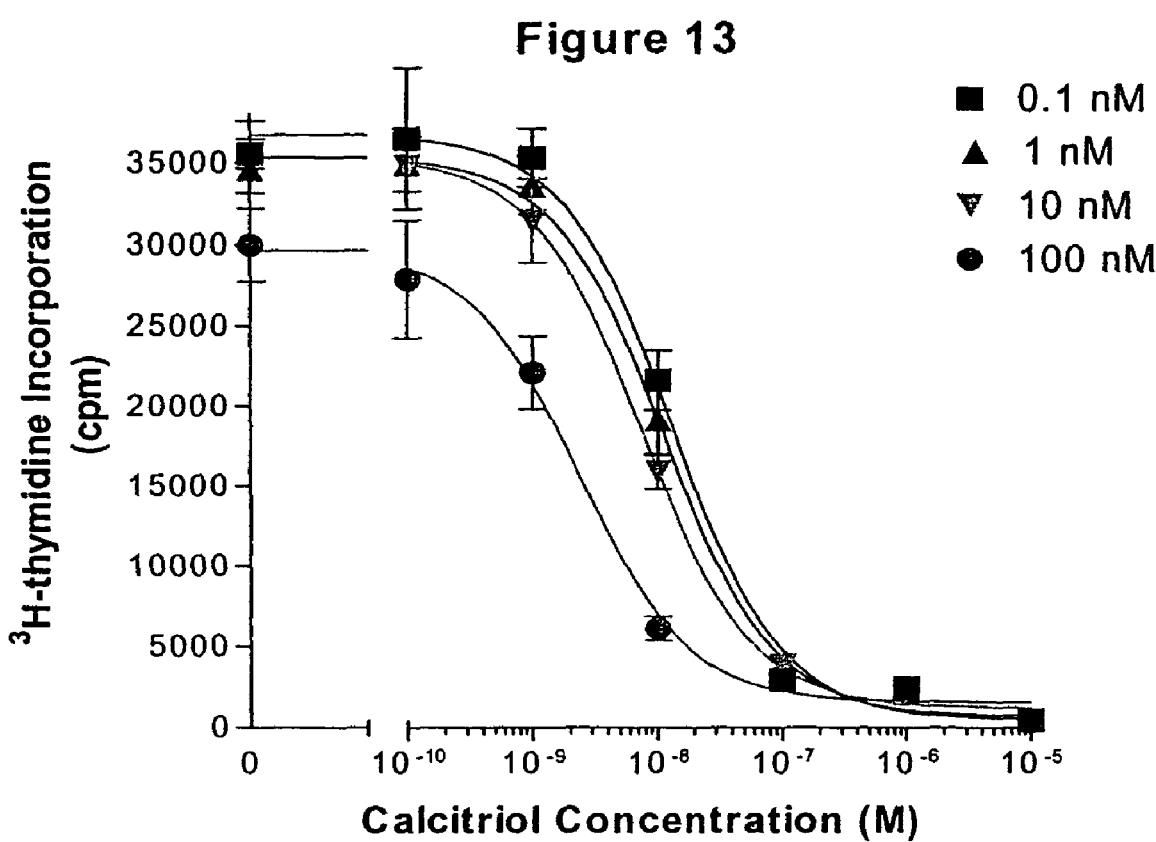
FIG. 13 is a graph showing that compound I(o) and calcitriol act to inhibit the proliferation of SCC-25 cells. SCC-25 cells were treated with specified concentrations of calcitriol and compound I(o) for three days. Cells were then incubated with [³H]-thymidine for 6 h at 37° C. in a humidified atmosphere containing 5% $CO_2$. Plates were harvested and radioactivity measured. Dose response curves for 0.1 nM I(o) (■), 1 nM I(o) (▲), 10 nM I(o) (▼) and 100 nM I(o) (♦) are shown.
Figure 14:
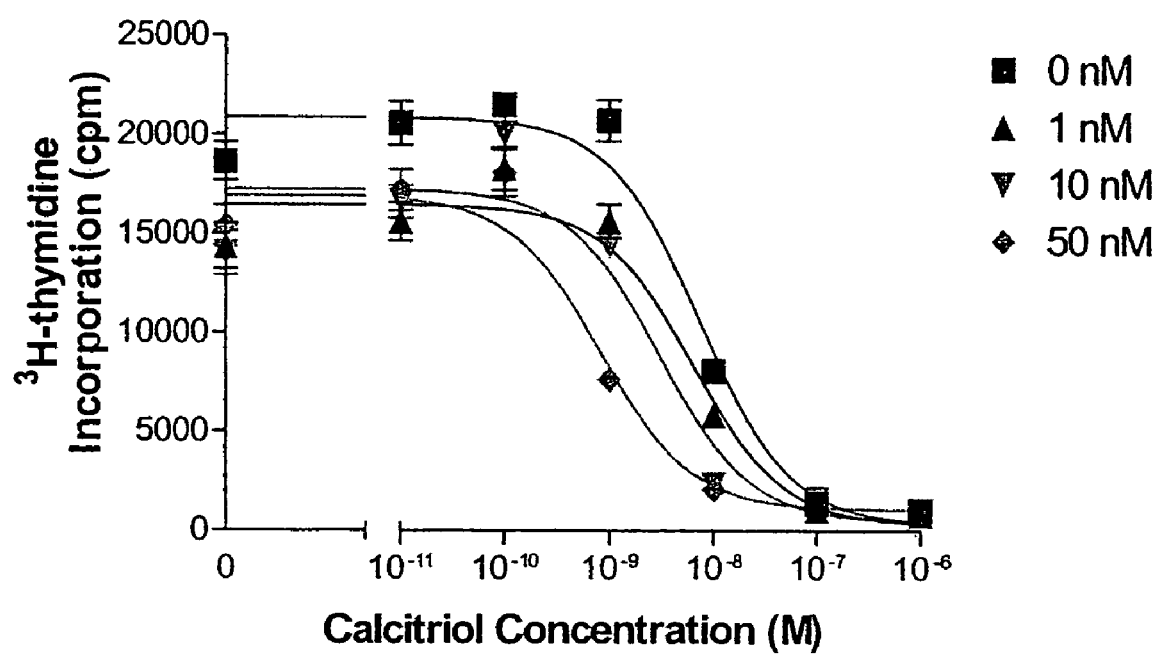
FIG. 14 is a graph showing that compound I(n) and calcitriol act to inhibit the proliferation of SCC-25 cells. SCC-25 cells were treated with specified concentrations of calcitriol and compound I(n) for three days. Cells were then incubated with [3H]-thymidine for 6 h at 37° C. in a humidified atmosphere containing 5% $CO_2$. Plates were harvested and radioactivity measured. Dose response curves for 0.1 nM I(n) (■), 1 nM I(g) (▲), 10 nM I(n) (▼) and 50 nM I(n) (♦) are shown.

Results for compounds I(g), I(e), I(c), I(a), I(j), I(l), I(i), I(o) and I(n) are shown in FIGS. 6-14, respectfully.

Example 27

Human Epidermal Keratinocyte Prolferation Assay (HEK) Assay (i) Material and Reagents
Normal HEK cells (Cambrex, Walkersville, Md.)
Bullet kit KGM-Ca media (Cambrex, Walkersville, Md.)
Reagent pack (Cambrex, Walkersville, Md.)
Calcium chloride (Cambrex, Walkersville, Md.)
25 cm² tissue culture flasks
96-well tissue culture plates
[$^3$H]-thymidine (Perkin Elmer, Boston, Mass.)
calcitriol (1 mM) reconstituted in isopropanol (Sigma, St. Louis, Mo.)
96-well filter plates
scintillation fluid
scintillation counter
Tomtec cell harvester (Tomtec, Hamden, Conn.)
(ii) Reagent Preparation
1. HEK Cell Media
Supplemented KGM media with additional reagents provided in the bullet kit as per supplier's instructions.
Added calcium chloride to final concentration of 0.3 mM.
2. Calcitriol Dilutions
Stock: Calcitriol (1 mM)

| Concentration (final) | from previous step (μl) | KGM media (μl) | Isopropanol (μl) | Concentration (actual) |
|---|---|---|---|---|
| $10^{-6}$ M | 8 of stock | 992 | 12 | $8 \times 10^{-6}$ M |
| $10^{-7}$ M | 100 | 882 | 18 | $8 \times 10^{-7}$ M |
| $10^{-8}$ M | 100 | 882 | 18 | $8 \times 10^{-8}$ M |
| $10^{-9}$ M | 100 | 882 | 18 | $8 \times 10^{-9}$ M |
| $10^{-10}$ M | 100 | 882 | 18 | $8 \times 10^{-10}$ M |
| $10^{-11}$ M | 100 | 882 | 18 | $8 \times 10^{-11}$ M |

3. Substrate Dilutions
Stock: substrate (0.1 mM)

| Concentration (final) | from previous step (μl) | KGM media (μl) | Isopropanol (μl) | Concentration (actual) |
|---|---|---|---|---|
| $10^{-7}$ M | 8 of stock | 992 | 12 | $8 \times 10^{-6}$ M |
| $5 \times 10^{-8}$ M | 500 | 490 | 10 | $8 \times 10^{-7}$ M |
| $10^{-8}$ M | 200 | 784 | 16 | $8 \times 10^{-8}$ M |
| $10^{-9}$ M | 100 | 882 | 18 | $8 \times 10^{-9}$ M |
| $10^{-10}$ M | 100 | 882 | 18 | $8 \times 10^{-11}$ M |

Figure 15:
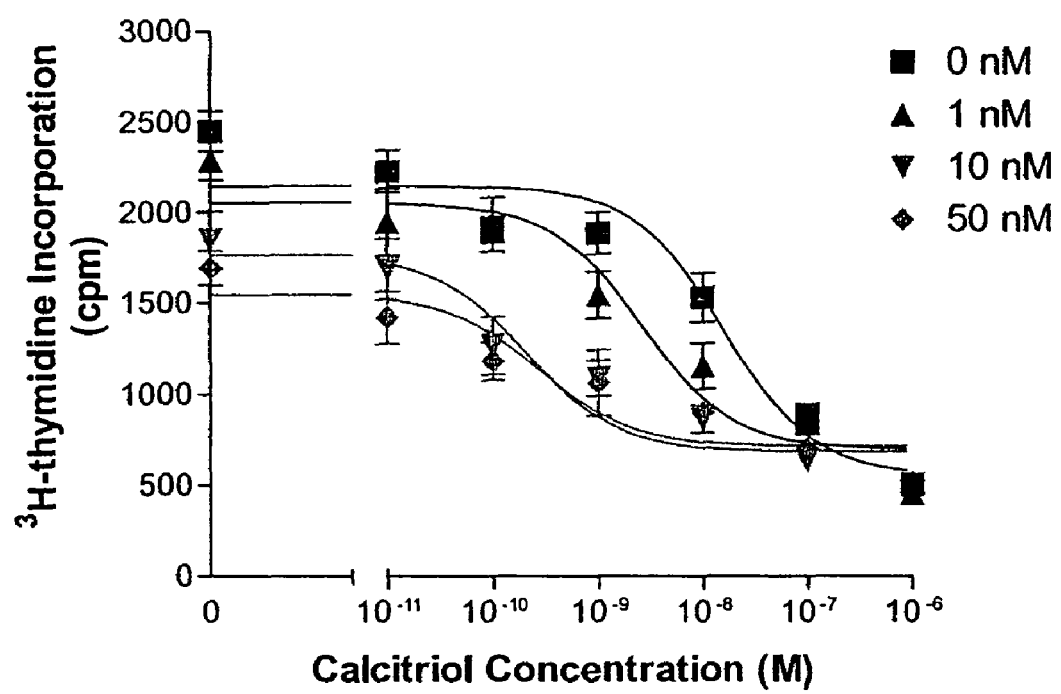
FIG. 15 is a graph showing that compound I(e) and calcitriol act to inhibit the proliferation of normal human epidermal keratinocytes (NHEK). NHEK were treated with specified concentrations of calcitriol and compound I(e) for three days. Cells were then incubated with [³H]-thymidine for 18 h at 37° C. in a humidified atmosphere containing 5% $CO_2$. Plates were harvested and radioactivity measured. Dose response curves in the absence of I(e) (■), 1 nM I(e) (▲), 10 nM I(e) (▼) and 50 nM I(e) (♦) are shown.
Figure 16:
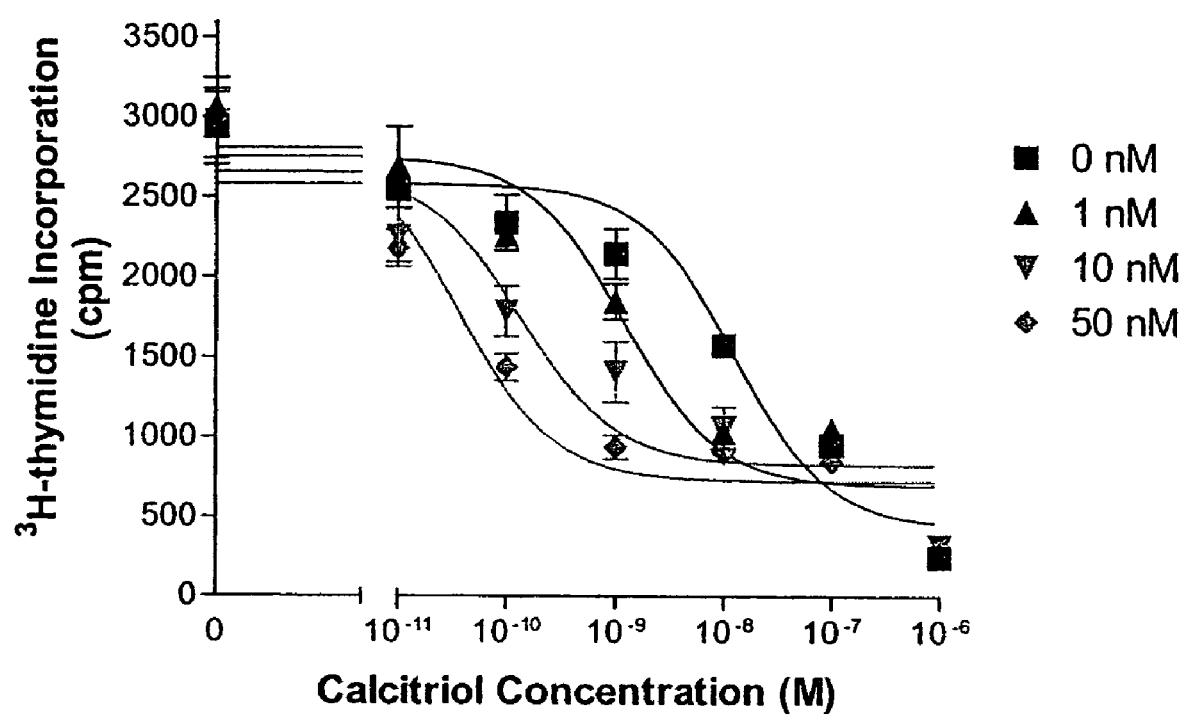
FIG. 16 is a graph showing that compound I(a) and calcitriol act to inhibit the proliferation of normal human epidermal keratinocytes (NHEK). NHEK were treated with specified concentrations of calcitriol and compound I(a) for three days. Cells were then incubated with [³H]-thymidine for 18 h at 37° C. in a humidified atmosphere containing 5% $CO_2$. Plates were harvested and radioactivity measured. Dose response curves in the absence of I(a) (■), 1 nM I(a) (▲), 10 nM I(a) (▼) and 50 nM I(a) (♦) are shown.
Figure 17:
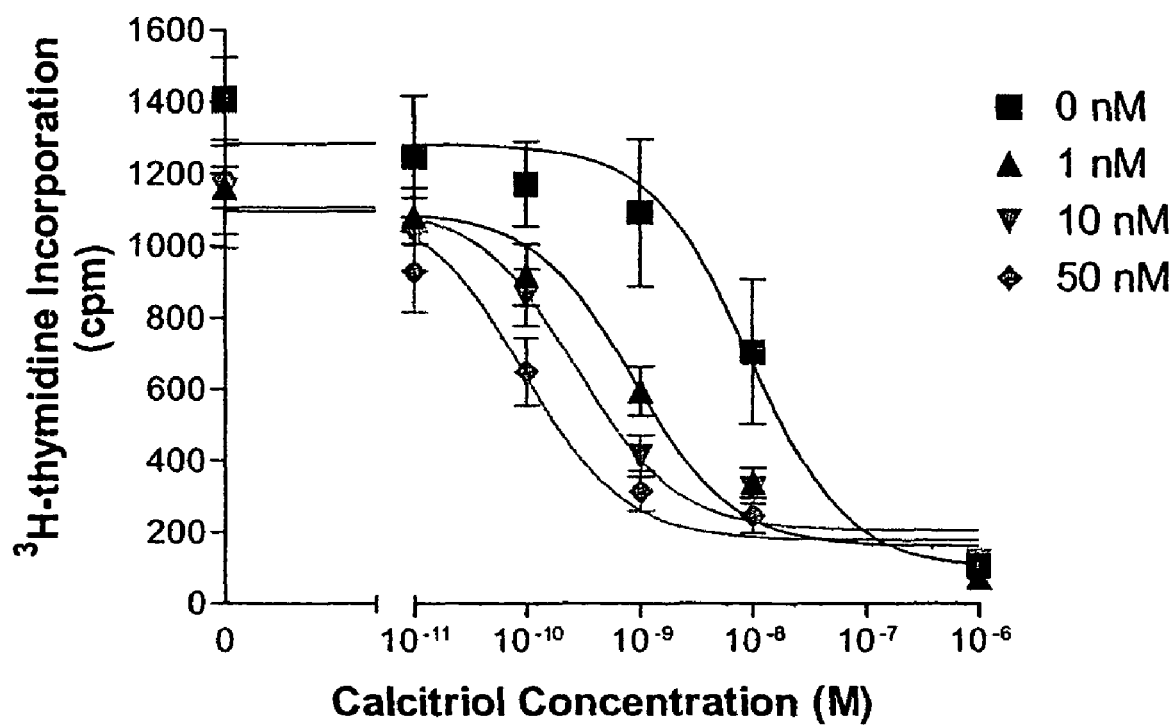
FIG. 17 is a graph showing that compound I(i) and calcitriol act to inhibit the proliferation of normal human epidermal keratinocytes (NHEK). NHEK were treated with specified concentrations of calcitriol and compound I(i) for three days. Cells were then incubated with [³H]-thymidine for 18 h at 37° C. in a humidified atmosphere containing 5% $CO_2$. Plates were harvested and radioactivity measured. Dose response curves in the absence of I(i) (■), 1 nM I(i) (▲), 10 nM I(i) (▼) and 50 nM I(i) (♦) are shown.
Figure 18:
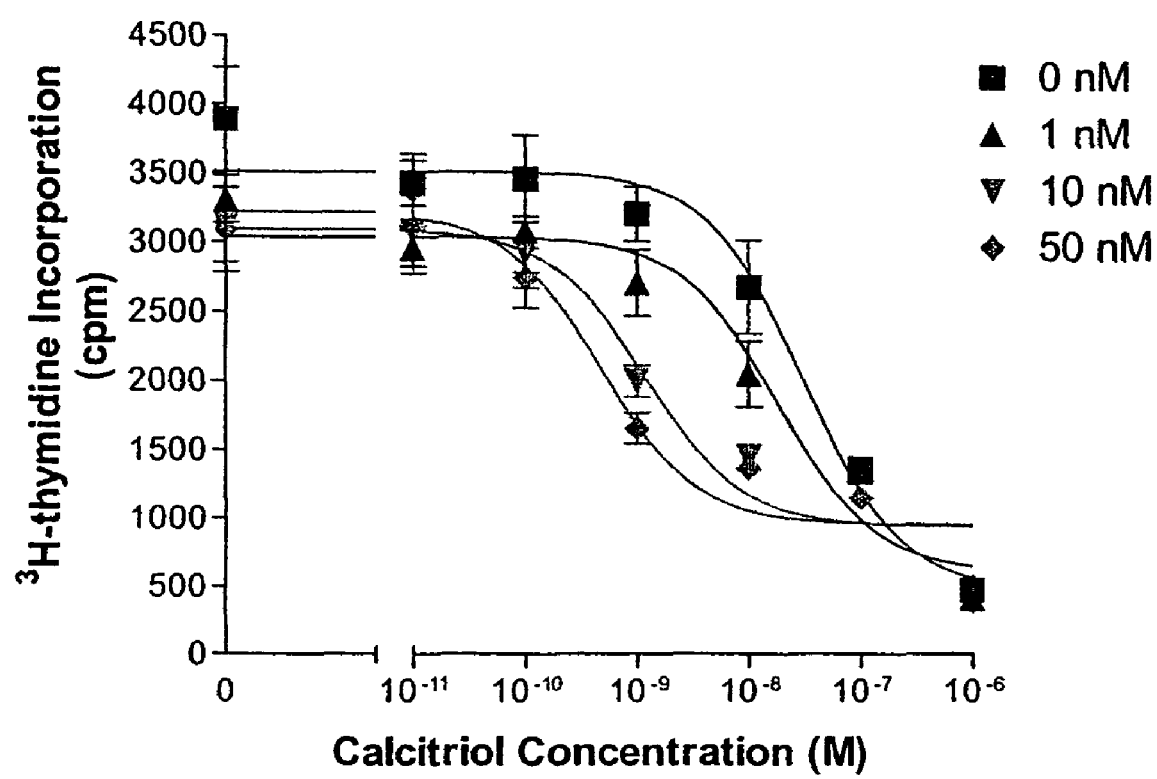
FIG. 18 is a graph showing that compound I(o) and calcitriol act to inhibit the proliferation of normal human epidermal keratinocytes (NHEK). NHEK were treated with specified concentrations of calcitriol and compound CTA112 for three days. Cells were then incubated with [³H]-thymidine for 18 h at 37° C. in a humidified atmosphere containing 5% $CO_2$. Plates were harvested and radioactivity measured. Dose response curves in the absence of I(o) (■), 1 nM I(o) (▲), 10 nM I(o) (▼) and 50 nM I(o) (♦) are shown.
Figure 19:
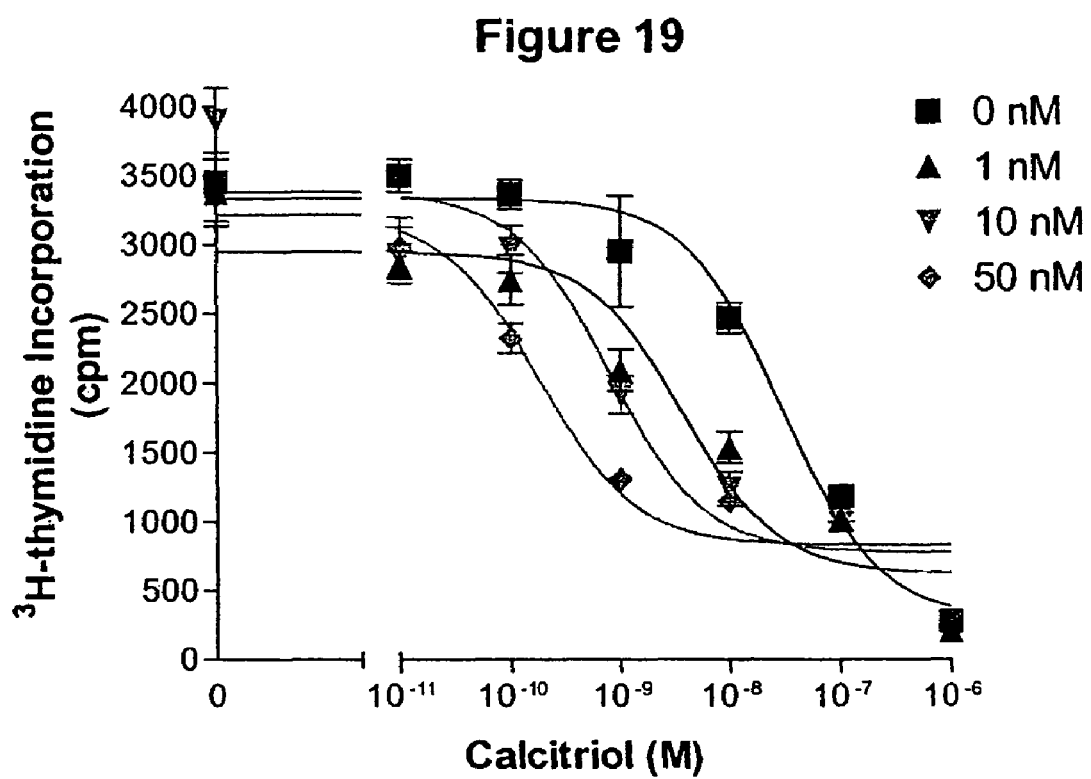
FIG. 19 is a graph showing that compound I(n) and calcitriol act to inhibit the proliferation of normal human epidermal keratinocytes (NHEK). NHEK were treated with specified concentrations of calcitriol and compound CTA113 for three days. Cells were then incubated with [³H]-thymidine for 18 h at 37° C. in a humidified atmosphere containing 5% $CO_2$. Plates were harvested and radioactivity measured. Dose response curves in the absence of I(n) (■), 1 nM I(n) (▲), 10 nM I(n) (▼) and 50 nM I(n) (♦) are shown.

(iii) Procedure:
1. Cell Culture
Thawed one vial of HEK cells containing at least 500 K, and divided into 5 25 cm² flasks with 5 ml HEK cell media. 24 h later, removed media and replenished with 5 ml fresh media. Changed media again 48 h later.
2. Preparation of Cell Suspension
On the day of the assay, washed the monolayer of HEK cells once with 1×PBS buffer (provided in reagent pack) and then trypsinized for 5 min at 37° C. Added trypsin neutralizing solution (provided in reagent pack). Collected cells into tube, centrifuged cells (500×g, 5 min) and resuspended in HEK cell media. Counted cells and adjusted density to 150,000 cells/ml. Diluted cells further 1:30 with HEK cell media.
2. Cell Plating
Added 150 μl of cell suspension to appropriately labelled wells of a 96-well plate. Incubated plate for 48 h at 37° C. in a humidified atmosphere containing 5% $CO_2$ for adherence of cells to wells.
3. Compound Addition
Added 25 μL of calcitriol ($10^{-6}$ to $10^{-11}$ M, final) and added 25 μl of substrate ($10^{-7}$ to $10^{-10}$ M, final) and incubated for 32 hours at 37° C. in a humidified atmosphere containing 5% $CO_2$.
4. Cell Harvesting and Counting
Added 0.2 μCi/well of [$^3$H]-thymidine in 20 μl of HEK cell media to each well. Incubated plates for 18 h at 37° C. in a humidified atmosphere containing 5% $CO_2$. Aspirated media and washed with 1×PBS. Trypsinize-cells for 30 min at 37° C. in a humidified atmosphere containing 5% $CO_2$. Harvested cells onto filter plates using Tomtec cell harvester as per manufacturer's instructions. Added 25 μl scintillation fluid per well. Measured radioactivity using a scintillation counter. All values were normalized for background.
5. Results:
Graphs showing results for compounds I(e), I(a), I(i), I(o) and I(n) are shown in FIGS. 15-19 respectfully

Example 28

Proposed Topical Composition Containing a Compound of the Invention

Dissolve a compound of the invention (1 mg) in 1 g of almond oil. To this solution add mineral oil (40 g) and self emulsifying beeswax (20 g). Heat the mixture to liquefy, and add hot water (40 mL) and stir the mixture well to provide a cream containing approximately 10 μg of a compound of the invention per gram of cream.

Example 29

Proposed Cream Containing 50 μg of a Compound of the Invention/g

| | |
|---|---|
| Compound of the invention | 50 mg |
| Cetomacrogol 1000 | 25 g |
| Cetostearyl alcohol | 75 g |
| Chloroallylhexaminium chloride | 0.5 g |
| Glycerol | 30 g |
| Disodium hydrogenphosphate | 2 g |
| Sodium dihydrogenphosphate | 0.1 g |
| Liquid paraffin | 60 g |
| Polyoxyethylene stearylether | 12 g |
| White petrolatum | 160 g |
| Purified water up to | 1000 g |

Dissolve a compound of the invention in a solution of glycerol, disodium hydrogenphosphate, sodium dihydrogenphosphate and polyoxyethylene stearylether dissolved in water. Mix with the melted cetomacrogol 1000, liquid paraffin, cetostearyl alcohol and white petrolatum. Homogenize the emulsion and cool. Dissolve chloroallylhexaminium chloride in part of the water and mix until homogeneous with the emulsion. Fill the cream in aluminium tubes.

Example 30

Proposed Cream Containing 100 μg of a Compound of the Invention/g

| | |
|---|---|
| Compound of the invention | 100 mg |
| Cetomacrogol 1000 | 30 g |
| Cetostearyl alcohol | 60 g |
| Chloroallylhexaminium chloride | 0.5 g |
| Propylenglycol | 30 g |
| Disodium hydrogenphosphate | 2 g |
| Sodium dihydrogenphosphate | 0.1 g |
| Liquid paraffin | 50 g |
| White petrolatum | 170 g |
| Purified water up to | 1000 g |

Melt cetomacrogol 1000, cetostearyl alcohol, liquid paraffin and white petrolatum at 75° C. Dissolve propylenglycol in water at 75° C. and mix the solution with the fatty phase. Homogenize the emulsion and cool to 30° C. Mill the compound of the invention to particle size below 5 μm and suspend in an aqueous solution of disodium hydrogenphosphate, sodium dihydrogenphosphate and chloroallylhexaminium chloride. Add the suspension to the emulsion and fill the cream in tubes.

Example 31

Proposed Lotion Containing 50 μg of a Compound of the Invention/g

| | |
|---|---|
| Compound of the invention | 50 mg |
| Absolute alcohol | 400 g |
| Hydroxypropylcellulose | 1 g |
| Menthol | 1 g |
| Sodium citrate | 1 g |
| Propylenglycol | 40 g |
| Purified water up to | 1000 ml |

Dissolve hydroxypropylcellulose, sodium citrate and propylenglycol in water. Mix with a solution of a compound of the invention and menthol in absolute alcohol. Fill the lotion in polyethylen plastic bottles.

Example 32

Proposed Capsules Containing a Compound of the Invention

A compound of the invention is suspended in arachis oil to a final concentration of 5 μg/ml oil. Mix together, with heating, 10 parts by weight of gelatine, 5 parts by weight of glycerine, 0.08 parts by weight potassium sorbate, and 14 parts by weight distilled water and form into soft gelatine capsules. Then fill each capsule with 100 μl of compound in oil suspension, such that each capsule contains 0.5 μg of the compound.

TABLE 1

Summary of Results from Examples 21-24

| Cpd # | CYP24 $IC_{50}$ (nM) (HPK1A-ras cells) | CYP24 $IC_{50}$ (nM) (V79-CYP24 cells) | CYP27A1 $IC_{50}$ (nM) | VDR Binding (nM) |
|---|---|---|---|---|
| I(a) | 5 | 4 | >1000 | >2000 |
| I(c) | 33 | 20 | >1000 | >2000 |
| I(e) | 66 | 29 | >1000 | >2000 |
| I(g) | 20 | 26 | >1000 | >2000 |
| I(i) | | 8.5 | | >2000 |
| I(j) | | 27 | | >2000 |
| I(k) | | 300 | | >2000 |
| I(l) | | 42 | | >2000 |
| I(m) | | 120 | | >2000 |
| I(n) | | 23 | | |
| I(o) | | 20 | | |
| I(p) | | 42 | | |
| I(q) | | 78 | | |
| I(s) | | 580 | | |
| ketoconazole | 300 | 300 | | |

The invention claimed is:

1. A method for treating diseases which benefit from an inhibition of the catabolism of 1α,25-dihydroxy vitamin $D_3$, or analogs thereof, said disease selected from the group consisting of breast cancer, lung cancer, prostate cancer, colon cancer, colorectal cancer, kidney cancer, head and neck cancer, pancreatic cancer, Kaposi's sarcoma, leukemia, psoriasis, hyperparathyroidism, secondary hyperparathyroidism and osteoporosis, comprising administering to a cell or animal in need thereof, an effective amount of a compound selected from a compound of Formula I, and pharmaceutically acceptable salts and prodrugs thereof:

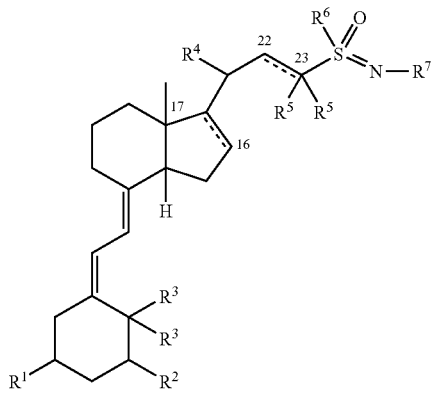

wherein
$R^1$ is selected from the group consisting of OH, $OC_{1-4}$alkyl, and halo;
$R^2$ is selected from the group consisting of H, OH, $OC_{1-4}$alkyl, and halo;
each $R^3$ are either both H or together form $=CH_2$;
$R^4$ is $C_{1-4}$alkyl;
----- represents a single or a double bond;
each $R^5$ can be the same or different and is selected from the group consisting of hydrogen, halo and $C_{1-4}$alkyl or each $R^5$ can be taken together to form a $C_{3-6}$cycloalkyl ring;
$R^6$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo;

$R^7$ is selected from the group consisting of H, $C_{1-6}$alkyl and $C(O)R^8$; and $R^8$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo, provided that when there is a double bond between C22 and C23, there is only one $R^5$ group attached to C23 and $R^5$ is selected from the group consisting of hydrogen, halo and $C_{1-4}$alkyl, wherein the prodrug is a phenyl ester, aliphatic ($C_8$-$C_{24}$) ester, acyloxymethyl ester, carbamate or amino acid ester formed from an available hydroxy, thiol, amino or carboxy group of a compound of Formula I.

2. The method according to claim 1, wherein the disease is selected from the group consisting of psoriasis, hyperparathyroidism, secondary hyperparathyroidism and osteoporosis.

3. The method according to claim 1, wherein the disease is selected from breast cancer, lung cancer, prostate cancer, colon cancer, colorectal cancer, kidney cancer, head and neck cancer, pancreatic cancer, Kaposi's sarcoma and leukemia.

4. The method according to claim 1, wherein the compound of formula I has the following relative stereochemistry:

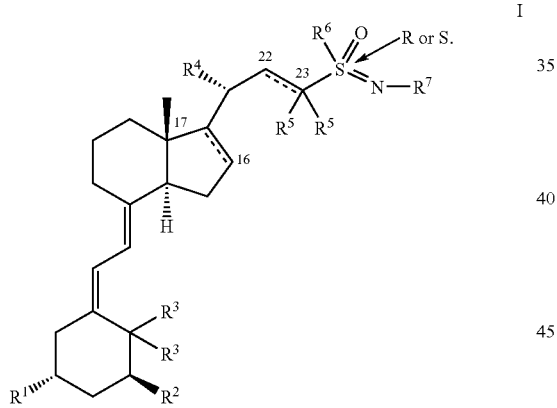

I

5. The method according to claim 1, wherein the compound of formula I is selected from the group consisting of:

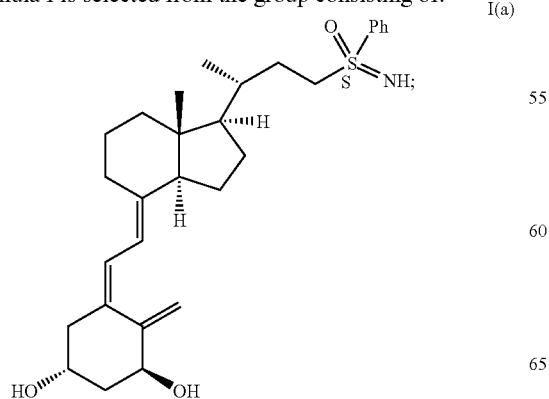

I(a)

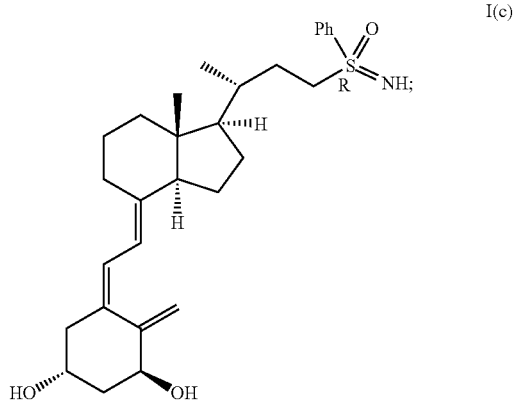

I(c)

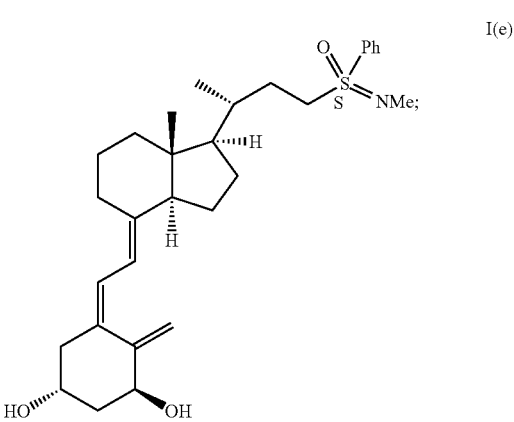

I(e)

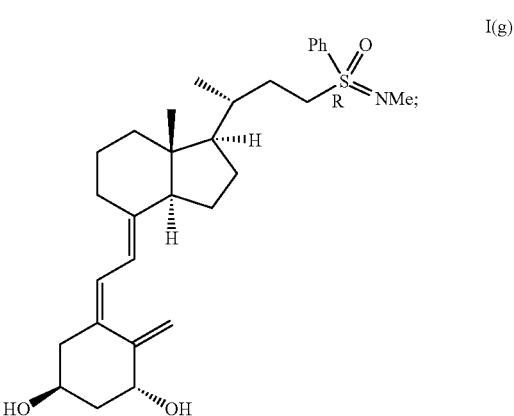

I(g)

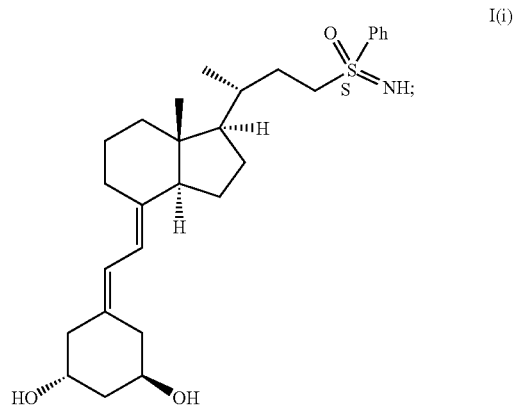

I(i)

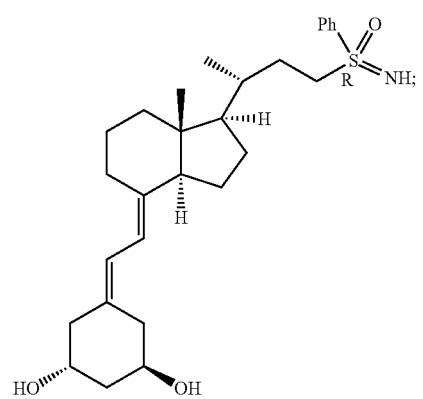
I(j)
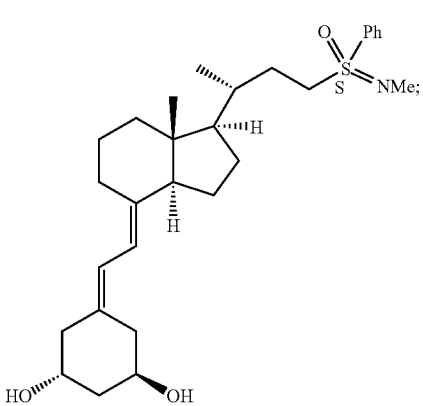
I(k)
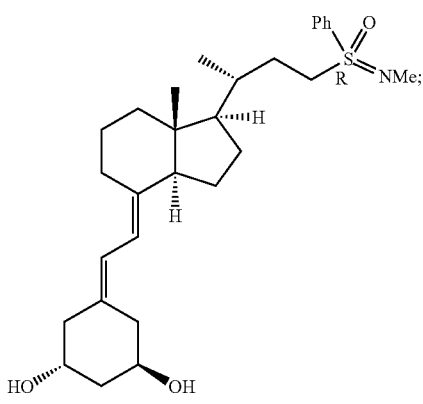
I(l)
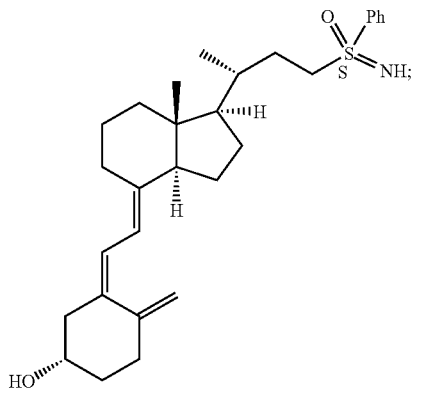
I(m)
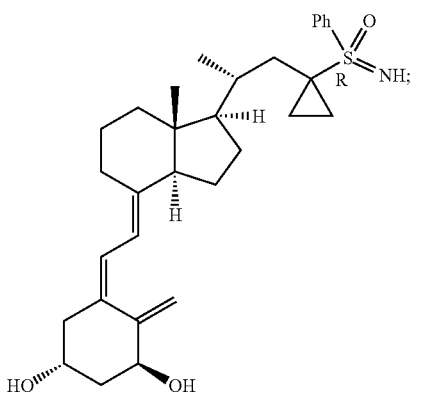
I(n)
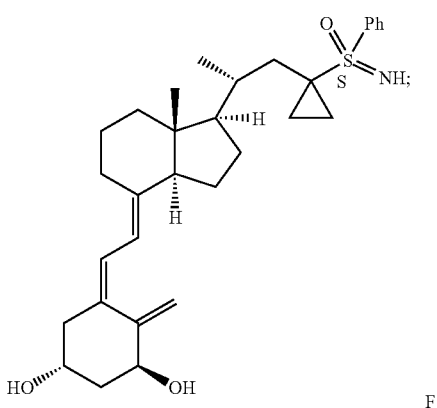
I(o)
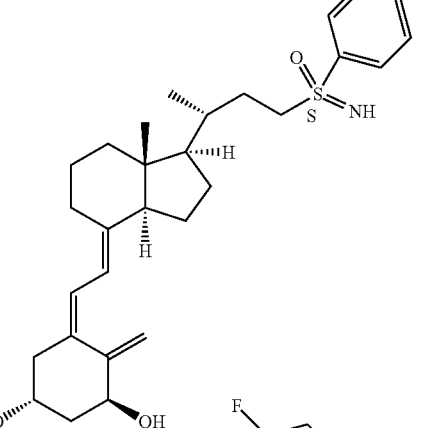
I(p)
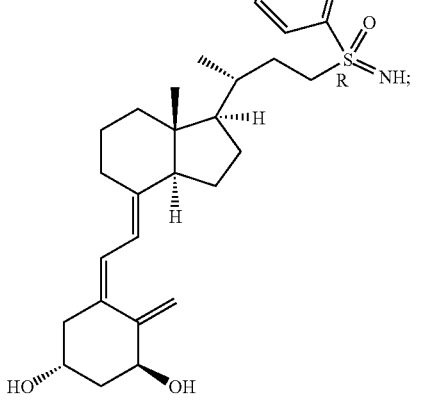
I(q)

I(r)
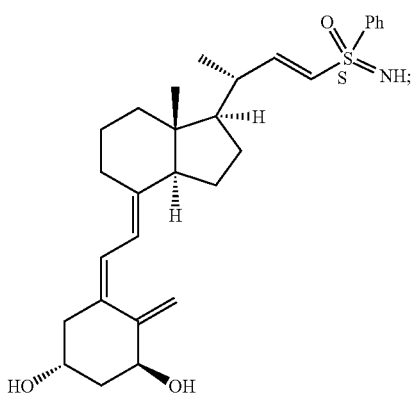

I(s)
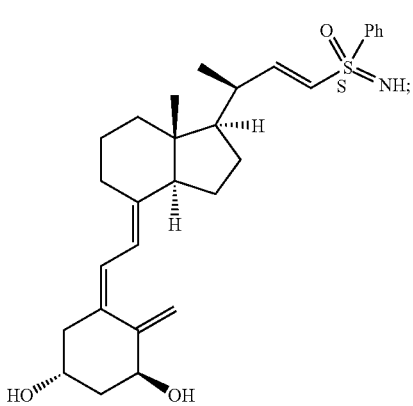

I(t)
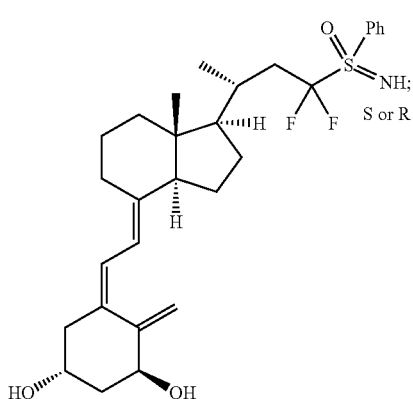

I(u)
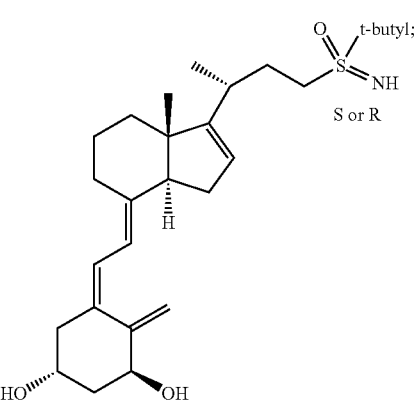

I(v)
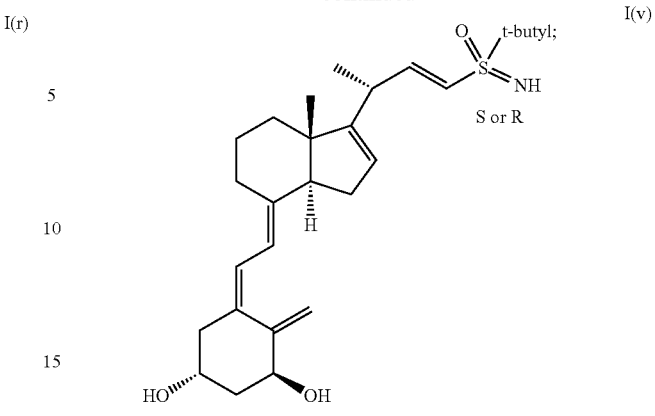

and pharmaceutically acceptable salts and prodrugs thereof.

6. The method according to claim 5, wherein the compound of Formula I is selected from the group consisting of I(a); I(c); I(e); I(g); I(i); I(j); I(l); I(m); I(n); I(o); I(p), I(q) and pharmaceutically acceptable salts and prodrugs thereof.

7. The method according to claim 6, wherein the compound of Formula I is selected from the group consisting of I(a), I(c), I(e), I(g), I(i), I(j), I(l), I(n) I(o), I(p) and pharmaceutically acceptable salts and prodrugs thereof.

8. A method for increasing the efficacy of a vitamin D receptor agonist comprising co-administering, to an animal or cell in need thereof, an effective amount of a vitamin D receptor agonist and an effective amount of a compound selected from a compound of Formula I, and pharmaceutically acceptable salts and prodrugs thereof:

I
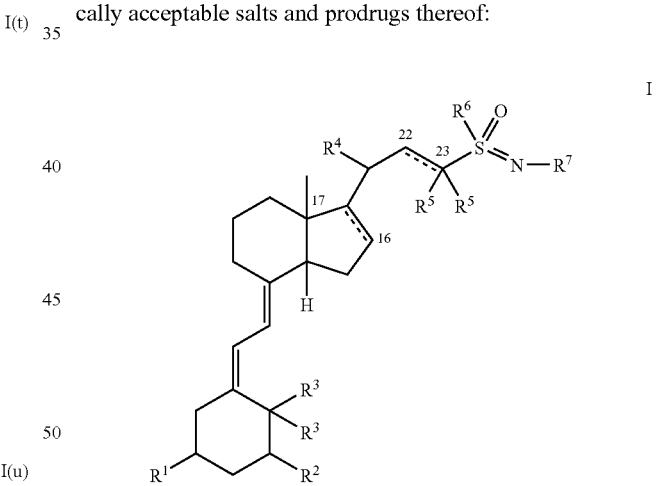

wherein
$R^1$ is selected from the group consisting of OH, $OC_{1-4}$alkyl, and halo;
$R^2$ is selected from the group consisting of H, OH, $OC_{1-4}$alkyl, and halo;
each $R^3$ are either both H or together form $=CH_2$;
$R^4$ is $C_{1-4}$alkyl;
----- represents a single or a double bond;
each $R^5$ can be the same or different and is selected from the group consisting of hydrogen, halo and $C_{1-4}$alkyl or each $R^5$ can be taken together to form a $C_{3-6}$cycloalkyl ring;
$R^6$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo;

$R^7$ is selected from the group consisting of H, $C_{1-6}$alkyl and $C(O)R^8$; and $R^8$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo, provided that when there is a double bond between C22 and C23, there is only one $R^5$ group attached to C23 and $R^5$ is selected from the group consisting of hydrogen, halo and $C_{1-4}$alkyl, wherein the prodrug is a phenyl ester, aliphatic ($C_8$-$C_{24}$) ester, acyloxymethyl ester, carbamate or amino acid ester formed from an available hydroxy, thiol, amino or carboxy group of a compound of Formula I.

9. The method according to claim 8, wherein the vitamin D receptor agonist is 1α,25-dihydroxy vitamin $D_3$ (calcitriol), or an analog thereof.

10. A method for treating a disease selected from the group consisting of breast cancer, lung cancer, prostate cancer, colon cancer, colorectal cancer, kidney cancer, head and neck cancer, pancreatic cancer, Kaposi's sarcoma, leukemia, psoriasis, hyperparathyroidism, secondary hyperparathyroidism and osteoporosis, comprising: co-administering, to an animal or cell in need thereof, an effective amount of a vitamin D receptor agonist and an effective amount of a compound selected from a compound of Formula I and pharmaceutically acceptable salts and prodrugs thereof:

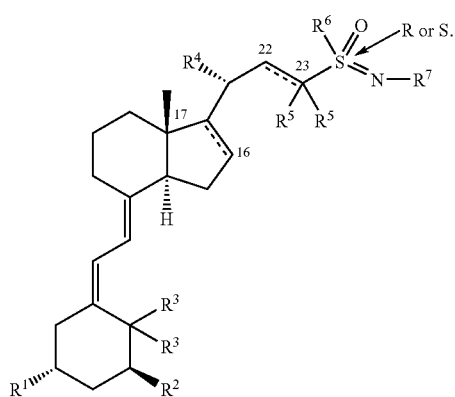

I wherein $R^1$ is selected from the group consisting of OH, $OC_{1-4}$alkyl, and halo;

$R^2$ is selected from the group consisting of H, OH, $OC_{1-4}$alkyl, and halo;

each $R^3$ are either both H or together form =$CH_2$;

$R^4$ is $C_{1-4}$alkyl;

----- represents a single or a double bond;

each $R^5$ can be the same or different and is selected from the group consisting of hydrogen, halo and $C_{1-4}$alkyl or each $R^5$ can be taken together to form a $C_{3-6}$cycloalkyl ring;

$R^6$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo;

$R^7$ is selected from the group consisting of H, $C_{1-6}$alkyl and $C(O)R^8$; and $R^8$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$-alkyl, $CF_3$, $NO_2$ and halo, provided that when there is a double bond between C22 and C23, there is only one $R^5$ group attached to C23 and $R^5$ is selected from the group consisting of hydrogen, halo and $C_{1-4}$alkyl, wherein the prodrug is a phenyl ester, aliphatic ($C_8$-$C_{24}$) ester, acyloxymethyl ester, carbamate or amino acid ester formed from an available hydroxy, thiol, amino or carboxy group of a compound of Formula I.

11. The method according to claim 10, wherein the disease is selected from the group consisting of psoriasis, hyperparathyroidism, secondary hyperparathyroidism and osteoporosis.

12. The method according to claim 10, wherein the disease is selected from the group consisting of breast cancer, lung cancer, prostate cancer, colon cancer, colorectal cancer, kidney cancer, head and neck cancer, pancreatic cancer, Kaposi's sarcoma and leukemia.

13. The method according to claim 8, wherein the compound of formula I has the following relative stereochemistry:

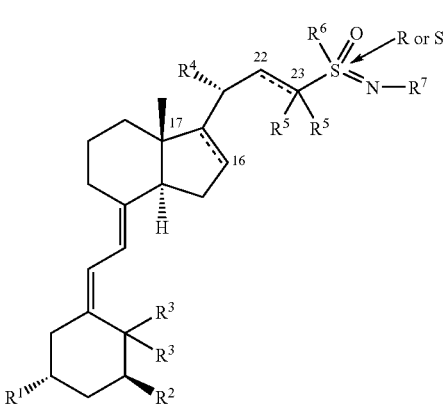

I

14. The method according to claim 8, wherein the compound of formula I is selected from the group consisting of:

I(a)
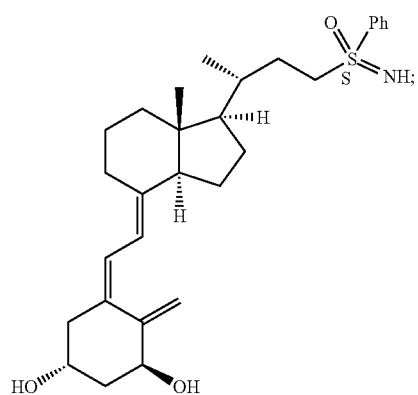
I(c)
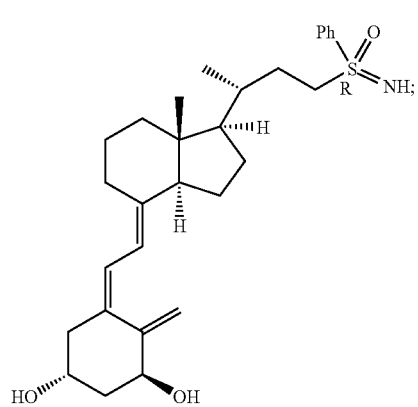
I(e)
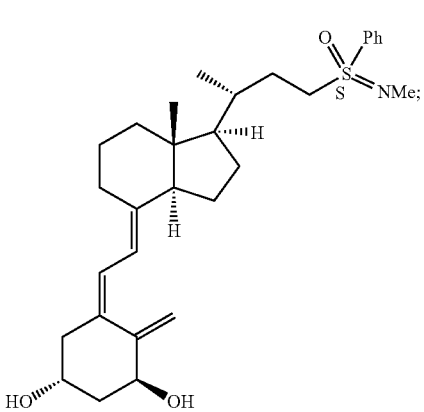
I(g)
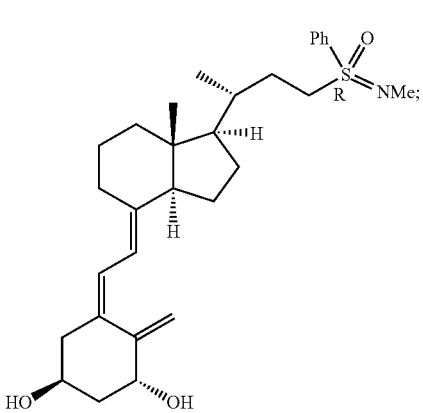
-continued
I(i)
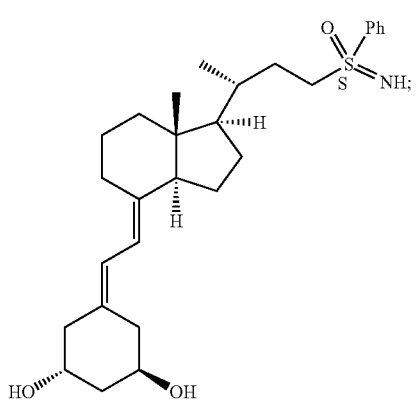
I(j)
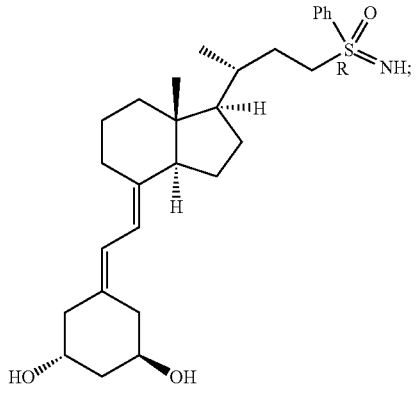
I(k)
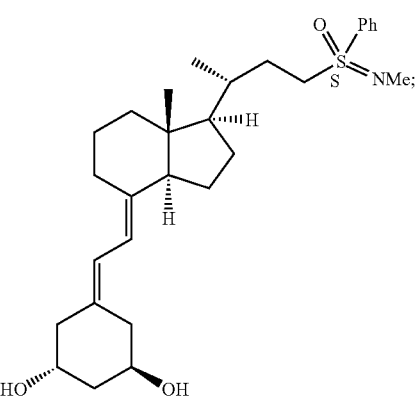
I(l)
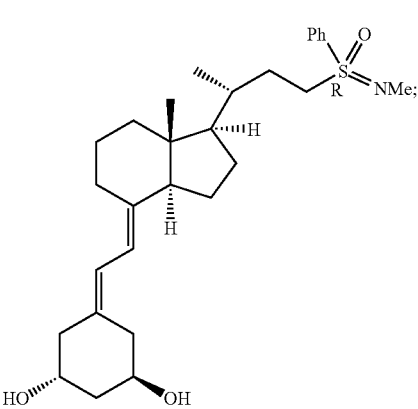

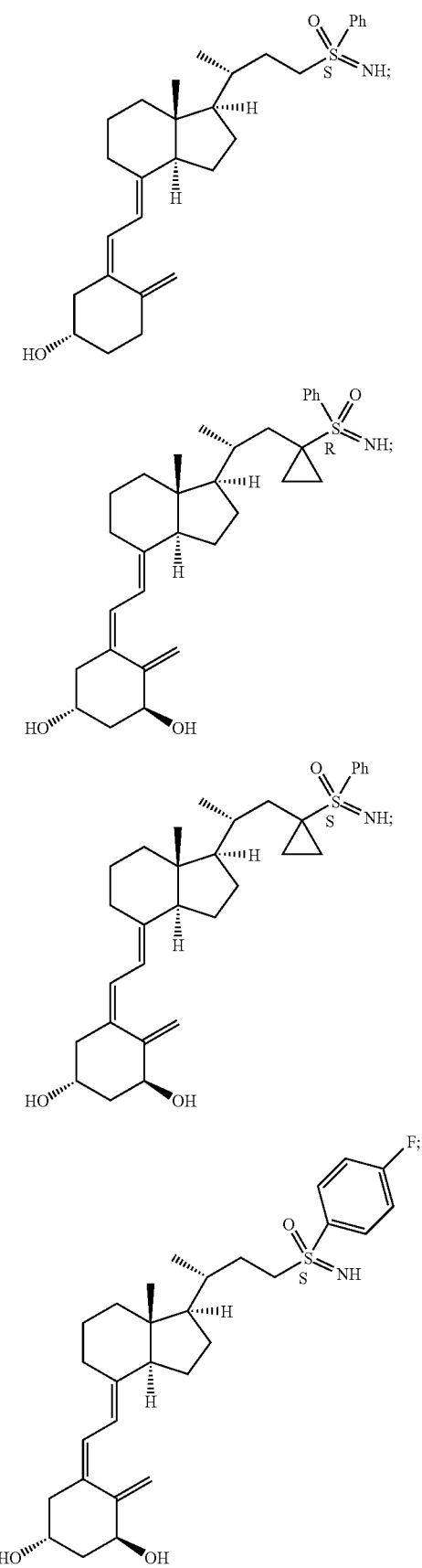
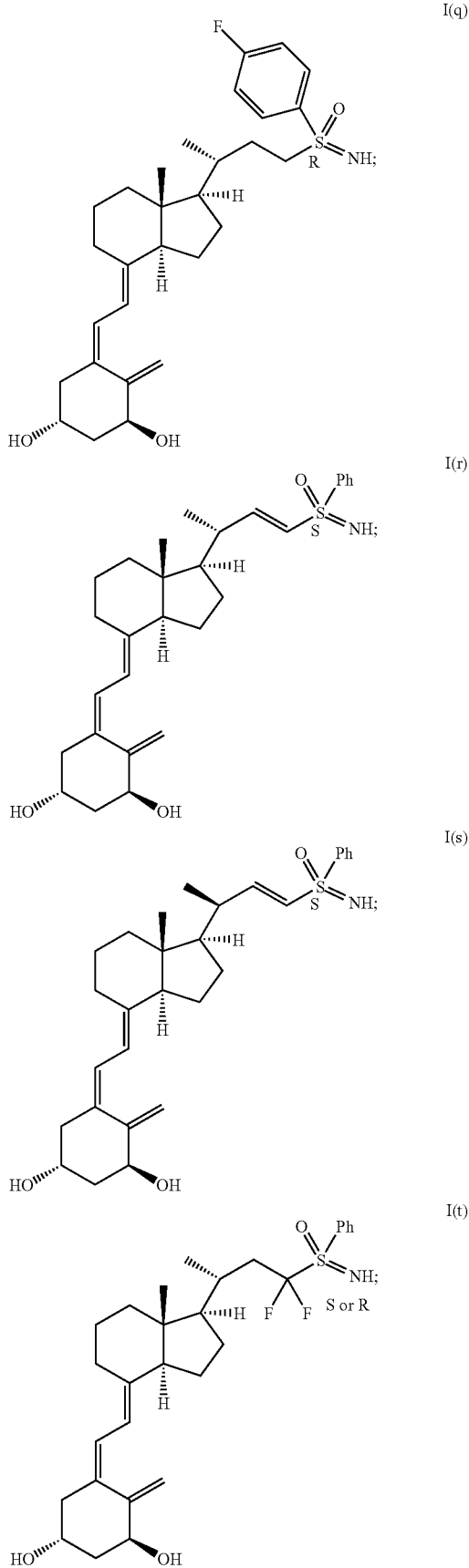

-continued

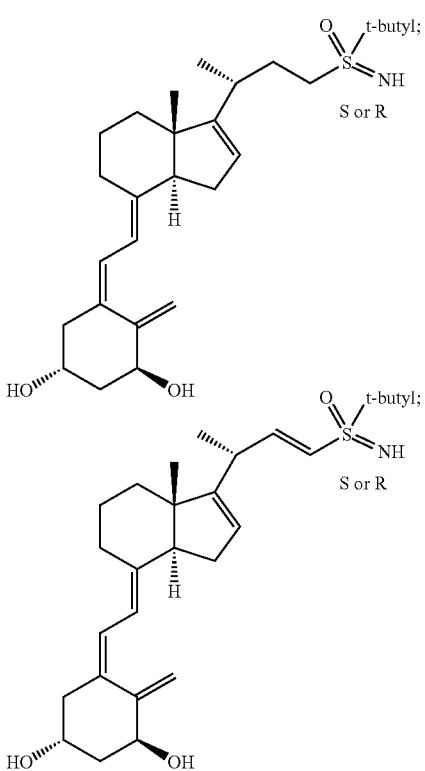

and pharmaceutically acceptable salts and prodrugs thereof.

15. The method according to claim 14, wherein the compound of Formula I is selected from the group consisting of I(a); I(c); I(e); I(g); I(i); I(j); I(l); I(m); I(n); I(o); I(p), I(q) and pharmaceutically acceptable salts and prodrugs thereof.

16. The method according to claim 15, wherein the compound of Formula I is selected from the group consisting of I(a), I(c), I(e), I(g), I(i), I(j), I(l), I(n) I(o), I(p) and pharmaceutically acceptable salts and prodrugs thereof.

17. A method of treating a disease selected from the group consisting of breast cancer, lung cancer, prostate cancer colon cancer, colorectal cancer, kidney cancer, head and neck cancer, pancreatic cancer, Kaposi's sarcoma, leukemia, psoriasis, hyperparathyroidism, secondary hyperparathyroidism and osteoporosis, comprising administering to an animal or cell in need thereof and in combination with one or more therapies or therapeutics to treat said disease, a compound selected from a compound of Formula I, and pharmaceutically acceptable salts and prodrugs thereof:

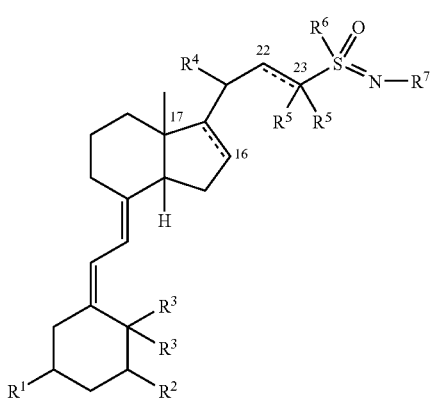

wherein
$R^1$ is selected from the group consisting of OH, $OC_{1-4}$alkyl, and halo;
$R^2$ is selected from the group consisting of H, OH, $OC_{1-4}$alkyl, and halo;
each $R^3$ are either both H or together form $=CH_2$;
$R^4$ is $C_{1-4}$alkyl;
----- represents a single or a double bond;
each $R^5$ can be the same or different and is selected from the group consisting of hydrogen, halo and $C_{1-4}$alkyl or each $R^5$ can be taken together to form a $C_{3-6}$cycloalkyl ring;
$R^6$ is selected from the group consisting of $C_{1-6}$alkyl, $C_{3-6}$cycloalkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo;
$R^7$ is selected from the group consisting of H, $C_{1-6}$alkyl and $C(O)R^8$; and
$R^8$ is selected from the group consisting of $C_{1-6}$alkyl, $C_{3-6}$cycloalkyl, aryl-$C_{1-4}$alkyl, aryl and heteroaryl, wherein each of $C_{1-6}$alkyl, $C_{3-6}$cycloalkyl, aryl and heteroaryl are either unsubstituted or substituted with 1-5 substituents independently selected from the group consisting of $C_{1-4}$alkyl, $OC_{1-4}$alkyl, $CF_3$, $NO_2$ and halo,
provided that when there is a double bond between C22 and C23, there is only one $R^5$ group attached to C23 and $R^5$ is selected from the group consisting of hydrogen, halo and $C_{1-4}$alkyl, wherein the prodrug is a phenyl ester, aliphatic ($C_8$-$C_{24}$) ester, acyloxymethyl ester, carbamate or amino acid ester formed from an available hydroxy, thiol, amino or carboxy group of a compound of Formula I.

18. The method according to claim 17, wherein the one or more therapies or therapeutics to treat said breast cancer, lung cancer, prostate cancer, colon cancer, colorectal cancer, kidney cancer, head and neck cancer, pancreatic cancer, cancer are selected from the group consisting of surgery, radiation, chemotherapy and biotherapy.

19. The method according to claim 17, wherein psoriasis is treated.

20. The method according to claim 19, wherein the one or more therapies or therapeutics to treat psoriasis are selected from the group consisting of ultraviolet B radiation, chemotherapy and biotherapy.

21. The method according to claim 17, wherein the compound of formula I has the following relative stereochemistry:

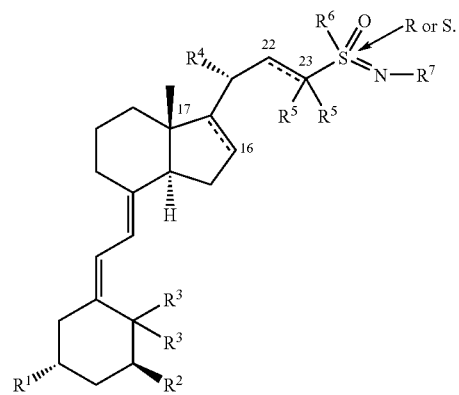

22. The method according to claim 17, wherein the compound of formula I is selected from the group consisting of:
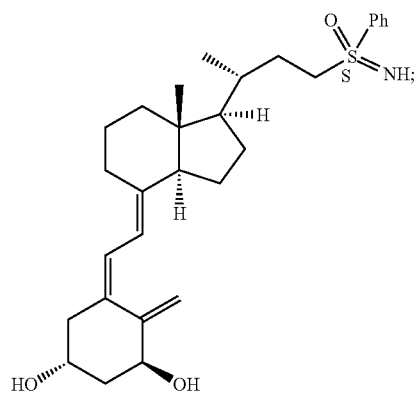
I(a)
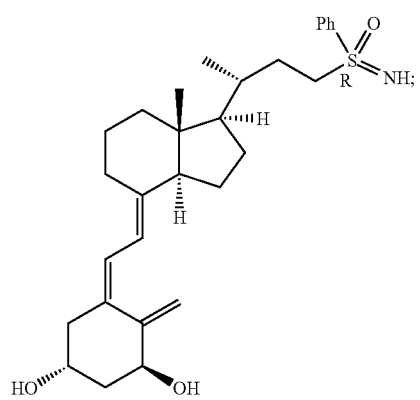
I(c)
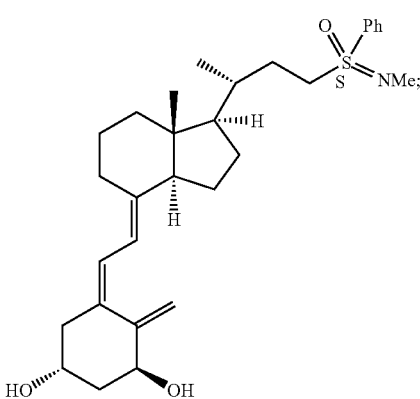
I(e)
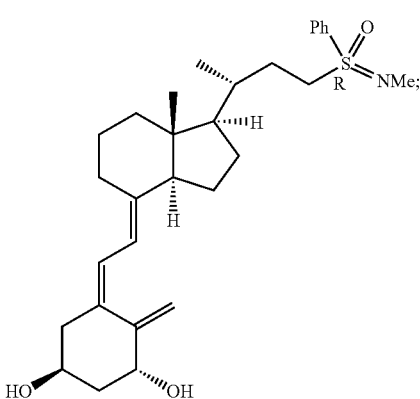
I(g)
-continued
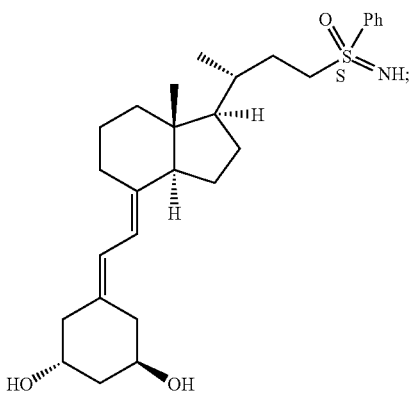
I(i)
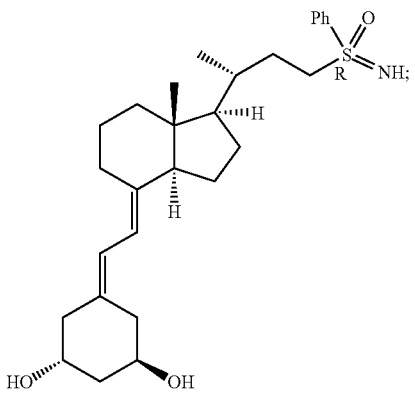
I(j)
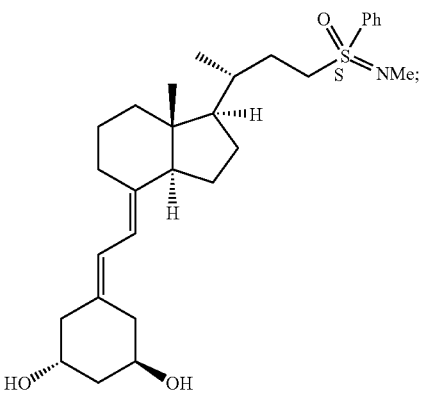
I(k)
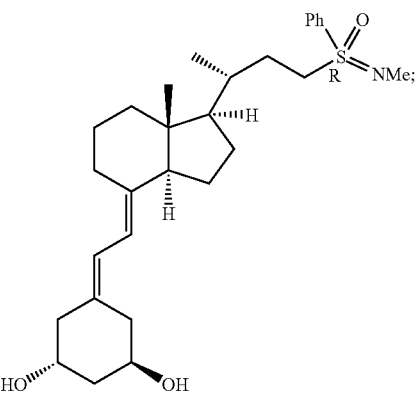
I(l)

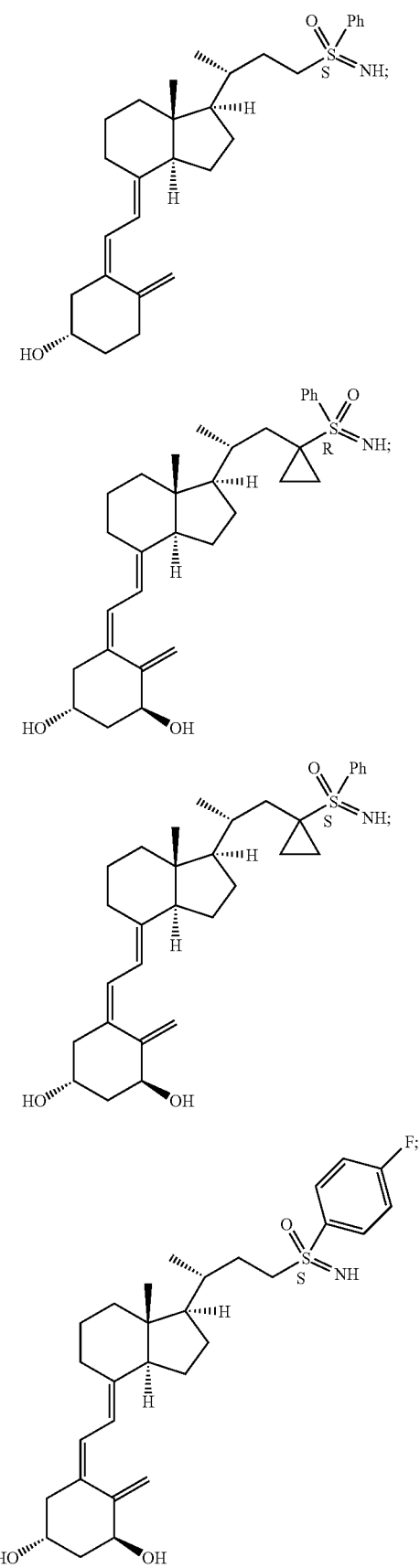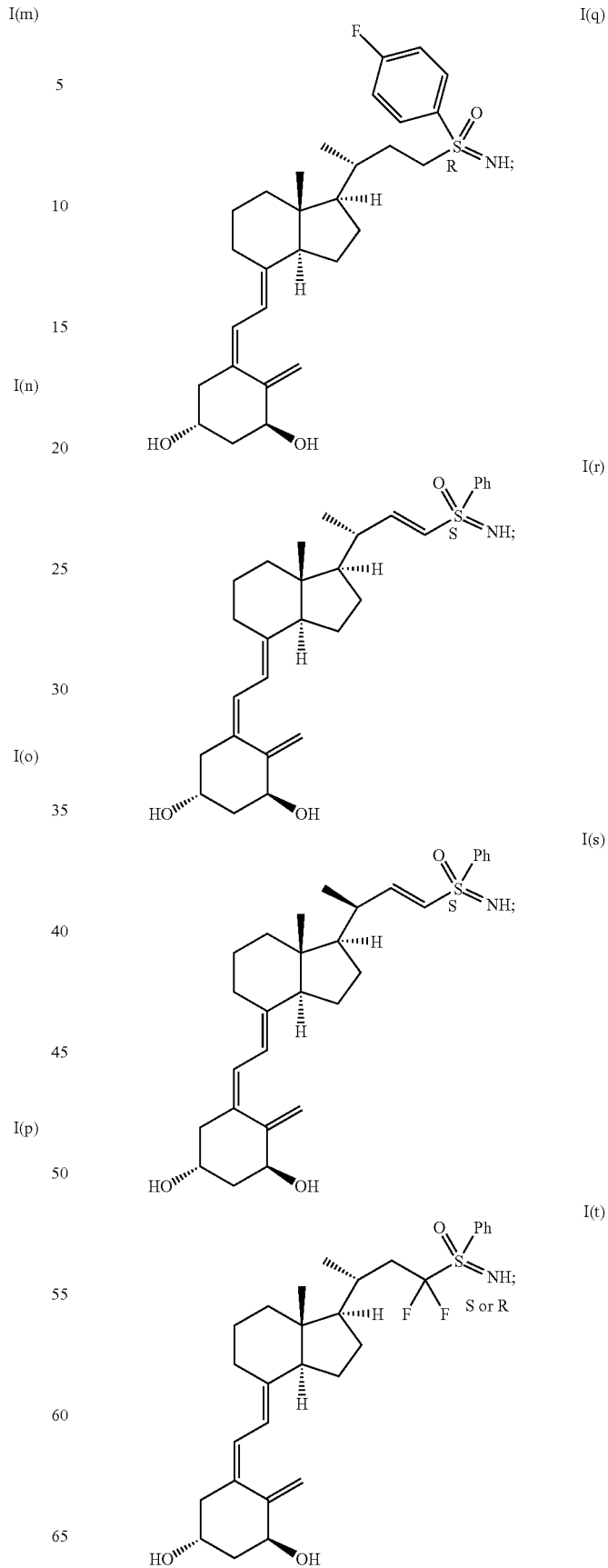

-continued

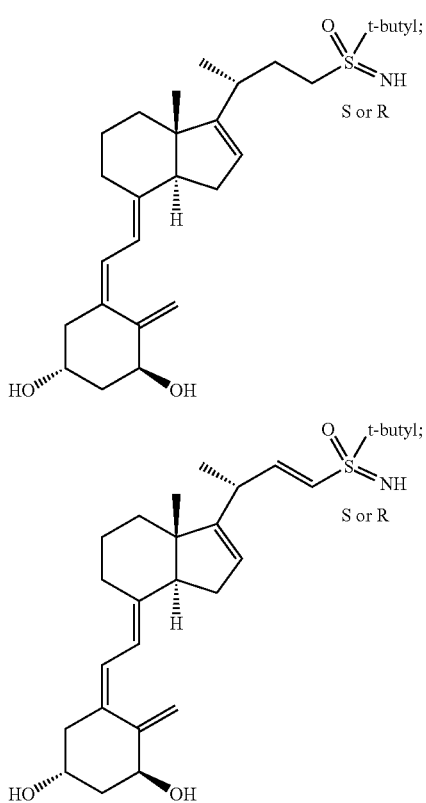

and pharmaceutically acceptable salts and prodrugs thereof.

23. The method according to claim 22, wherein the compound of Formula I is selected from the group consisting of I(a); I(c); I(e); I(g); I(i); I(j); I(l); I(m); I(n); I(o); I(p), I(q) and pharmaceutically acceptable salts and prodrugs thereof.

24. The method according to claim 23, wherein the compound of Formula I is selected from the group consisting of I(a), I(c), I(e), I(g), I(i), I(j), I(l), I(n) I(o), I(p) and pharmaceutically acceptable salts and prodrugs thereof.

25. The method according to claim 10, wherein the compound of formula I has the following relative stereochemistry:

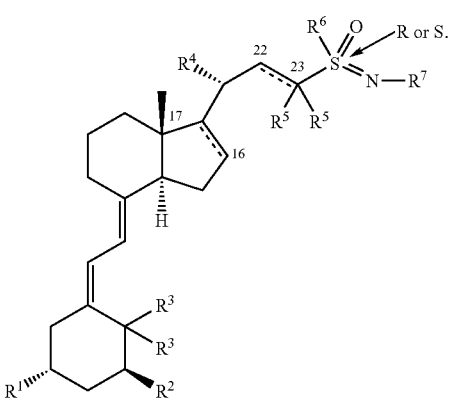

26. The method according to claim 10, wherein the compound of formula I is selected from the group consisting of:

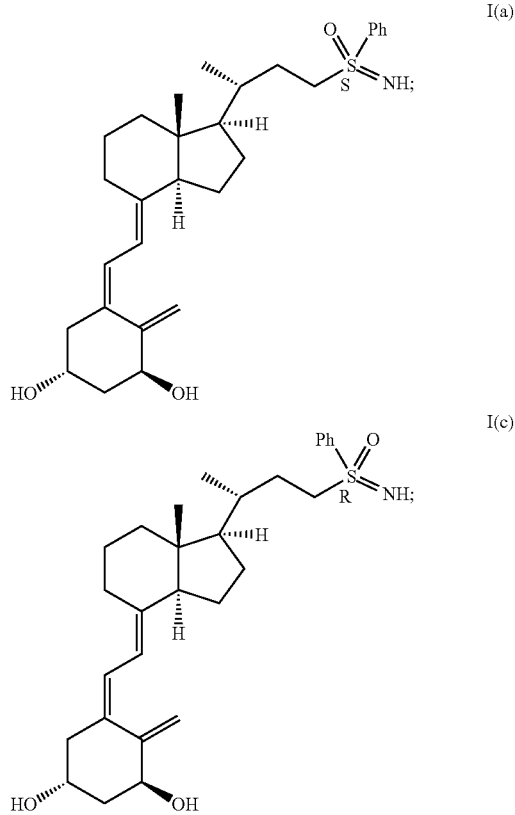

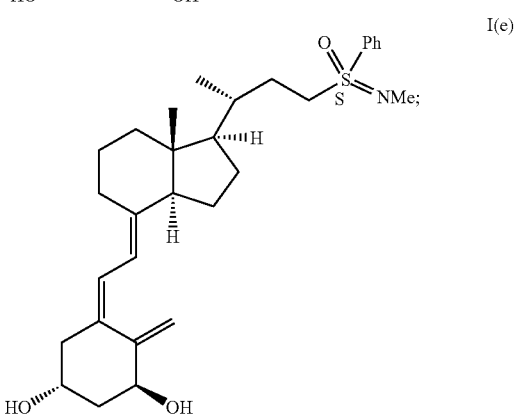

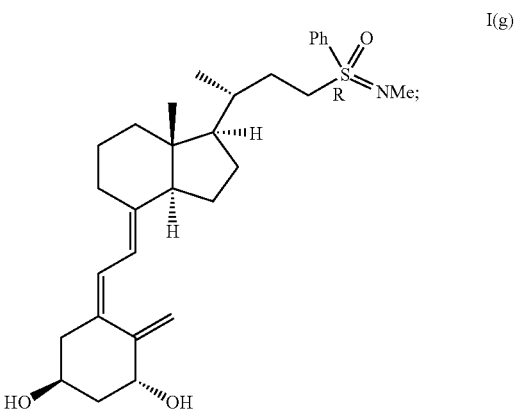

109
-continued
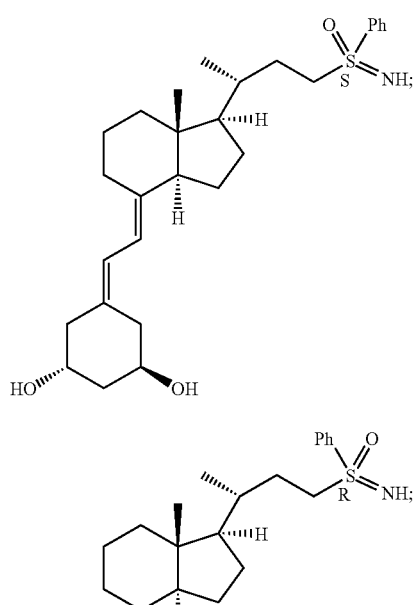
I(i)
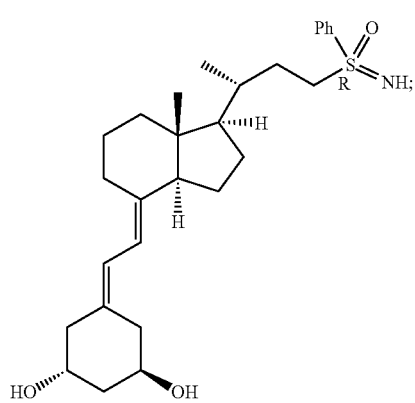
I(j)
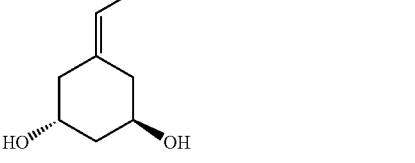
I(k)
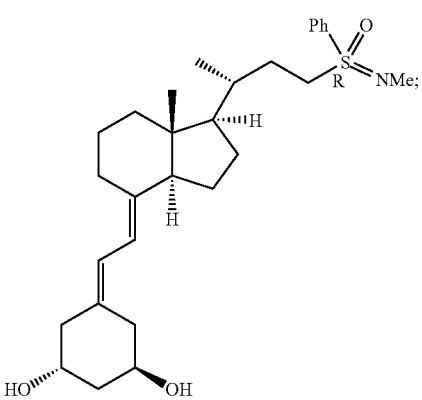
I(l)
110
-continued
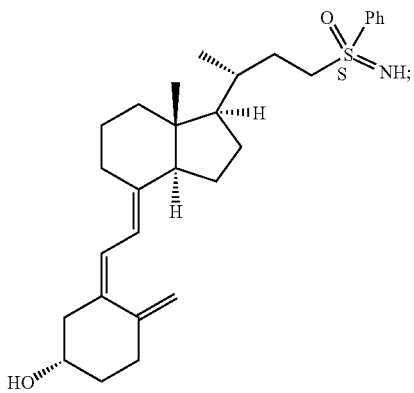
I(m)
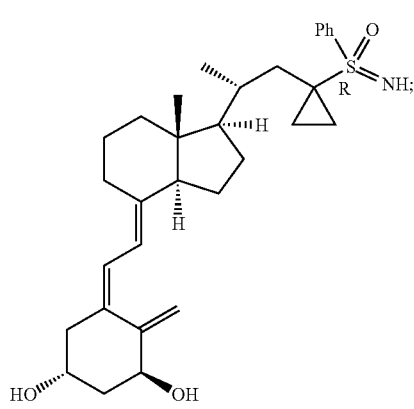
I(n)
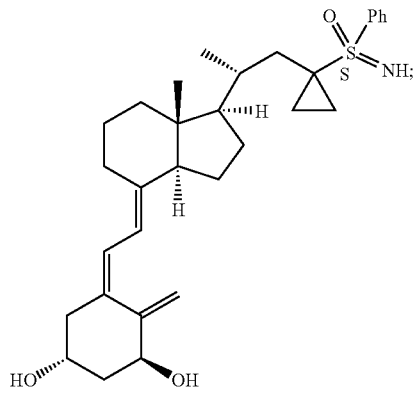
I(o)
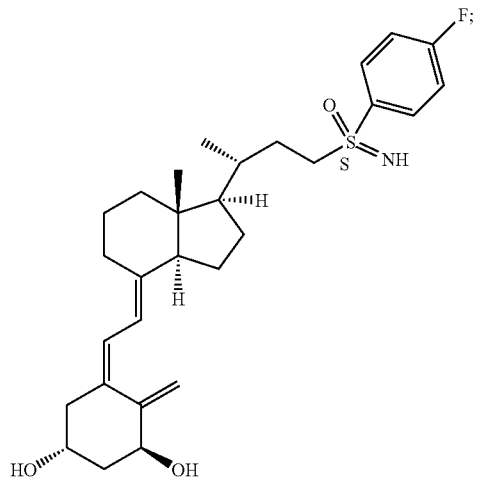
I(p)

111
-continued
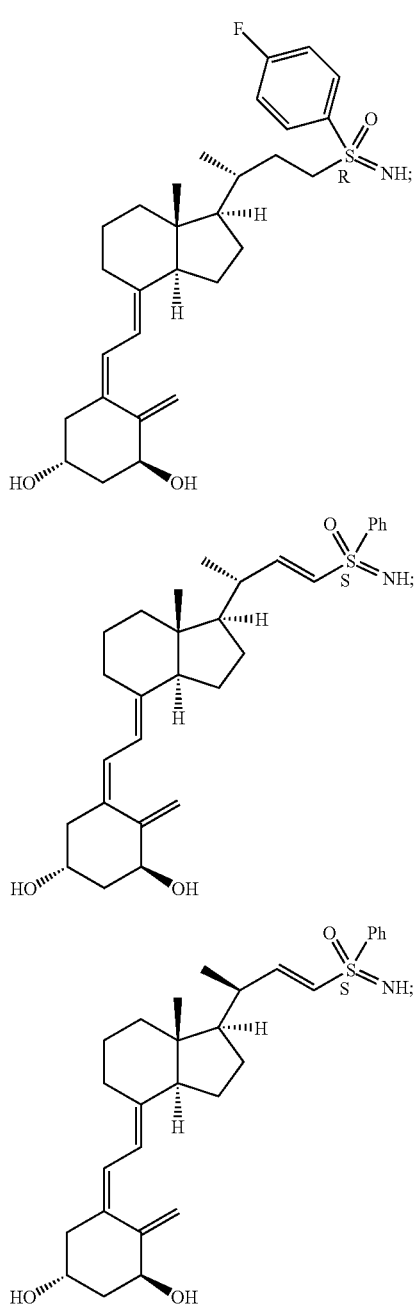
I(q)
I(r)
I(s)
112
-continued
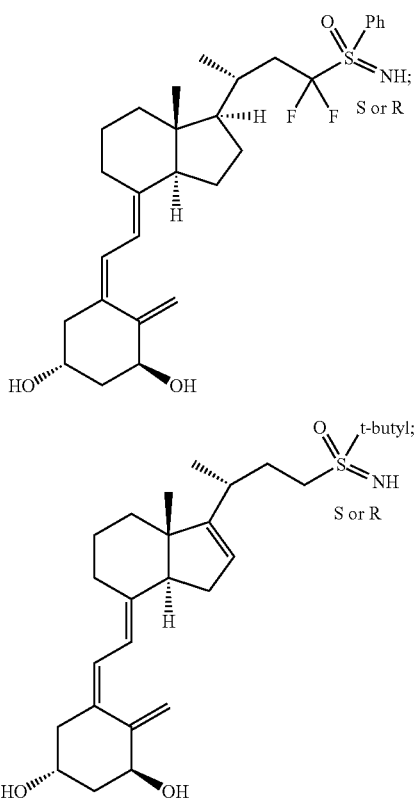
I(t)
I(u)
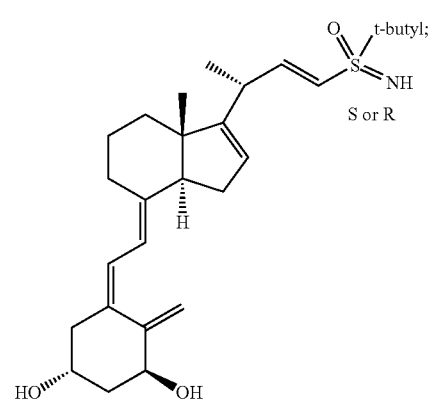
I(v)
and pharmaceutically acceptable salts and prodrugs thereof.
* * * * *